United States Patent
Cho et al.

(10) Patent No.: US 11,856,805 B2
(45) Date of Patent: Dec. 26, 2023

(54) ORGANOMETALLIC COMPOUND, ORGANIC LIGHT-EMITTING DEVICE INCLUDING THE SAME, AND DIAGNOSTIC COMPOSITION INCLUDING THE ORGANOMETALLIC COMPOUND

(71) Applicant: Samsung Electronics Co., Ltd., Suwon-si (KR)

(72) Inventors: Yongsuk Cho, Hwaseong-si (KR); Yoonhyun Kwak, Seoul (KR); Jongwon Choi, Yongin-si (KR); Hyun Koo, Seongnam-si (KR); Kyuhyun Im, Seongnam-si (KR); Dmitry Kravchuk, Hwaseong-si (KR); Seokhwan Hong, Seoul (KR)

(73) Assignee: SAMSUNG ELECTRONICS CO., LTD., Gyeonggi-Do (KR)

( * ) Notice: Subject to any disclaimer, the term of this patent is extended or adjusted under 35 U.S.C. 154(b) by 671 days.

(21) Appl. No.: 16/527,093

(22) Filed: Jul. 31, 2019

(65) Prior Publication Data

US 2020/0044166 A1 Feb. 6, 2020

(30) Foreign Application Priority Data

Jul. 31, 2018 (KR) .................. 10-2018-0089511
Jul. 29, 2019 (KR) .................. 10-2019-0091699

(51) Int. Cl.
*A61P 35/00* (2006.01)
*C07F 15/00* (2006.01)
(Continued)

(52) U.S. Cl.
CPC ....... *H10K 85/342* (2023.02); *C07F 15/0033* (2013.01); *C09K 11/06* (2013.01);
(Continued)

(58) Field of Classification Search
CPC ............. H01L 51/0085; H01L 51/5012; H01L 51/5016; H01L 51/5056; H01L 51/5072;
(Continued)

(56) References Cited

U.S. PATENT DOCUMENTS 6,465,115 B2 10/2002 Shi et al.
6,596,415 B2 7/2003 Shi et al.
(Continued)

FOREIGN PATENT DOCUMENTS

EP 1555269 A1 7/2005
EP 2821410 A2 1/2015
(Continued)

OTHER PUBLICATIONS

Extended European search report issued by the European Patent Office dated Dec. 3, 2019 in the examination of the European Patent Application No. 19189035.9, which corresponds to the U.S. Application above.
(Continued)

*Primary Examiner* — Sean M DeGuire
*Assistant Examiner* — Rachel Simbana
(74) *Attorney, Agent, or Firm* — CANTOR COLBURN LLP

(57) ABSTRACT

An organometallic compound represented by Formula 1:

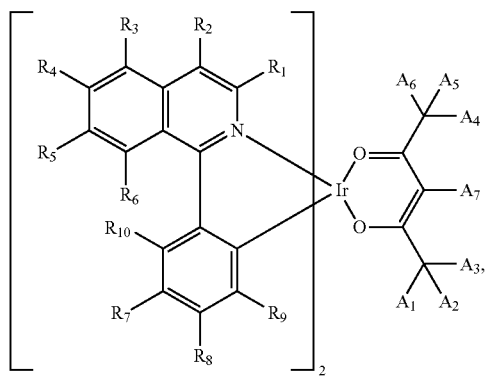

Formula 1 wherein, Formula 1, $R_1$ to $R_{10}$ and $A_1$ to $A_7$ are the same as described in the detailed description of the specification.

18 Claims, 1 Drawing Sheet

(51) Int. Cl.
| | |
|---|---|
| C09K 11/06 | (2006.01) |
| H10K 101/10 | (2023.01) |
| H10K 101/30 | (2023.01) |
| H10K 50/11 | (2023.01) |
| H10K 50/15 | (2023.01) |
| H10K 50/16 | (2023.01) |
| H10K 50/17 | (2023.01) |
| H10K 50/18 | (2023.01) |
| H10K 50/30 | (2023.01) |
| H10K 85/30 | (2023.01) |

(52) U.S. Cl.
CPC .......... C09K 2211/1029 (2013.01); C09K 2211/185 (2013.01); H10K 50/11 (2023.02); H10K 50/15 (2023.02); H10K 50/16 (2023.02); H10K 50/17 (2023.02); H10K 50/171 (2023.02); H10K 50/18 (2023.02); H10K 2101/10 (2023.02); H10K 2101/30 (2023.02)

(58) Field of Classification Search
CPC .......... H01L 51/5088; H01L 51/5092; H01L 51/5096; H01L 2251/552; C07F 15/0033; C09K 11/06; C09K 2211/1029; C09K 2211/185; H10K 85/341–348
See application file for complete search history.

(56) References Cited

U.S. PATENT DOCUMENTS

| | | | |
|---|---|---|---|
| 6,835,469 B2 | 12/2004 | Kwong et al. | |
| 7,265,224 B2 | 9/2007 | Park et al. | |
| 7,442,448 B2 | 10/2008 | Kim et al. | |
| 7,740,957 B2 | 6/2010 | Kim et al. | |
| 8,501,328 B2 | 8/2013 | Kim et al. | |
| 8,956,737 B2 | 2/2015 | Park et al. | |
| 2001/0019782 A1 | 9/2001 | Igarashi et al. | |
| 2002/0076576 A1* | 6/2002 | Li | H01L 51/0085 428/917 |
| 2007/0128468 A1 | 6/2007 | Kim et al. | |
| 2007/0278936 A1 | 12/2007 | Herron et al. | |
| 2008/0145526 A1* | 6/2008 | Mao | G01N 33/6839 546/10 |
| 2009/0085476 A1 | 4/2009 | Park et al. | |
| 2010/0000606 A1* | 1/2010 | Thompson | H01L 51/0085 257/E51.026 |
| 2010/0090591 A1 | 4/2010 | Alleyne et al. | |
| 2015/0001472 A1 | 1/2015 | Boudreault et al. | |
| 2017/0117492 A1 | 4/2017 | Kwong et al. | |
| 2019/0071461 A1 | 3/2019 | Boudreault et al. | |
| 2019/0157576 A1 | 5/2019 | Kwong et al. | |
| 2020/0031812 A1 | 1/2020 | Jung et al. | |
| 2022/0029112 A1 | 1/2022 | Kwak et al. | |
| 2022/0165969 A1 | 5/2022 | Kim et al. | |

FOREIGN PATENT DOCUMENTS

| | | |
|---|---|---|
| EP | 3549944 A1 | 10/2019 |
| JP | 20003782 A | 1/2000 |
| KR | 10-2004-0059304 A | 7/2004 |
| KR | 10-2005-0037479 A | 4/2005 |
| KR | 10-2006-0098859 A | 9/2006 |
| KR | 1020070030778 A | 3/2007 |
| KR | 10-2007-0105080 A | 10/2007 |
| KR | 10-2009-0032250 A | 4/2009 |
| KR | 10-2011-0077350 A | 7/2011 |
| KR | 10-2014-0041407 A | 4/2014 |
| KR | 10-2015-0003670 A | 1/2015 |
| KR | 1020180076332 A | 7/2018 |
| KR | 1020190115422 A | 10/2019 |
| KR | 1020200009834 A | 1/2020 |
| WO | 2018124697 A1 | 7/2018 |
| WO | WO-2018124697 A1 * | 7/2018 .......... C07F 15/0033 |

OTHER PUBLICATIONS

Adachi et al. "High-efficiency organic electrophosphorescent devices with tris)2-phenylpyridine) iridium doped into electron-transportintg materials", Appl. Phys. Lett., 2000, 77, 904.
Baldo et al. "Highly efficient phosphorescent emission from organic electroluminescent devices", Nature, 1998, 395, 151.
Baldo et al. "Very high-efficiency green organic light-emitting devices based on electrophosphorescence", Appl. Phys. Lett., 1999, 4, 75.
Kwong et al. "High operational stability of electrophosphorescent devices", Appl. Phys. Lett., 2000, 81, 162.
Lamansky et al. "Highly phosphorscent Bis-Cyclometalated Iridium Complexes: Synthesis, Photophysical Characterization, and Use in Organic Light Emitting Diodes", J. Am. Chem. Soc. 2001, 123, 4304-4312.
Lamansky et al. "Synthesis and Characterization of Phosphorescent Cyclometalated Iridium Complexes", Inorg. Chem, 2001, 40, 1704-1711.
English Abstract of KR 10-2007-0030778.
English Translation of Office Action dated Apr. 10, 2023, issued in corresponding KR Patent Application No. 10-2019-0091699, 5 pp.
Office Action dated Apr. 10, 2023, issued in corresponding KR Patent Application No. 10-2019-0091699, 5 pp.

* cited by examiner

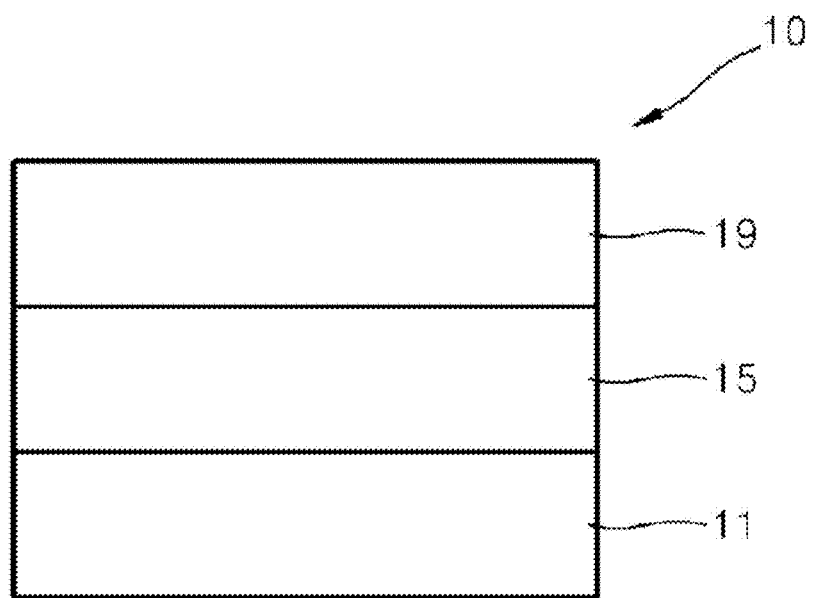

ORGANOMETALLIC COMPOUND, ORGANIC LIGHT-EMITTING DEVICE INCLUDING THE SAME, AND DIAGNOSTIC COMPOSITION INCLUDING THE ORGANOMETALLIC COMPOUND

CROSS-REFERENCE TO RELATED APPLICATION

This application claims priority to Korean Patent Applications Nos. 10-2018-0089511, filed on Jul. 31, 2018, and 10-2019-0091699, filed on Jul. 29, 2019, in the Korean Intellectual Property Office, and all the benefits accruing therefrom under 35 U.S.C. § 119, the content of which is incorporated herein in its entirety by reference.

BACKGROUND

1. Field

One or more embodiments relate to an organometallic compound, an organic light-emitting device including the same, and a diagnostic composition including the organometallic compound.

2. Description of the Related Art

Organic light-emitting devices (OLEDs) are self-emission devices, which have superior characteristics in terms of a viewing angle, response time, brightness, driving voltage, and response speed, and which produce full-color images.

In an example, an organic light-emitting device includes an anode, a cathode, and an organic layer disposed between the anode and the cathode, wherein the organic layer includes an emission layer. A hole transport region may be disposed between the anode and the emission layer, and an electron transport region may be disposed between the emission layer and the cathode. Holes provided from the anode may move toward the emission layer through the hole transport region, and electrons provided from the cathode may move toward the emission layer through the electron transport region. The holes and the electrons recombine in the emission layer to produce excitons. These excitons transit from an excited state to a ground state, thereby generating light.

Luminescent compounds may be used to monitor, sense, or detect a variety of biological materials including cells and proteins. An example of such luminescent compounds is a phosphorescent luminescent compound.

Various types of organic light emitting devices are known. However, there still remains a need in OLEDs having low driving voltage, high efficiency, high brightness, and long lifespan.

SUMMARY

Aspects of the present disclosure provide a novel organometallic compound, an organic light-emitting device including the same, and a diagnostic composition including the novel organometallic compound.

Additional aspects will be set forth in part in the description which follows and, in part, will be apparent from the description, or may be learned by practice of the presented embodiments.

An aspect of the present disclosure provides an organometallic compound represented by Formula 1:

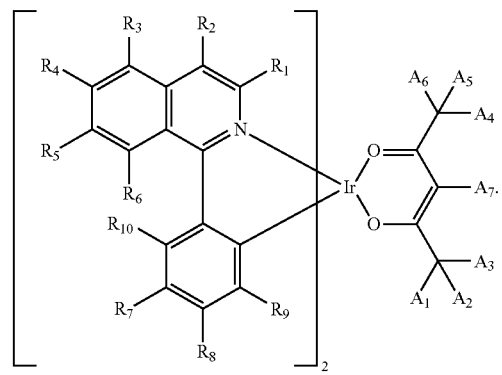

Formula 1

In Formula 1,
$R_1$ to $R_{10}$ and $A_7$ may each independently be hydrogen, deuterium, —F, —Cl, —Br, —I, —$SF_5$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_7$-$C_{60}$ arylalkyl group, a substituted or unsubstituted $C_1$-$C_{60}$ heteroaryl group, a substituted or unsubstituted $C_1$-$C_{60}$ heteroaryloxy group, a substituted or unsubstituted $C_1$-$C_{60}$ heteroarylthio group, a substituted or unsubstituted $C_2$-$C_{60}$ heteroarylalkyl group, a substituted or unsubstituted monovalent non-aromatic condensed polycyclic group, a substituted or unsubstituted monovalent non-aromatic condensed heteropolycyclic group, —$N(Q_1)(Q_2)$, —$Si(Q_3)(Q_4)(Q_5)$, —$Ge(Q_3)(Q_4)(Q_5)$, —$B(Q_6)(Q_7)$, —$P(=O)(Q_8)(Q_9)$, or —$P(Q_8)(Q_9)$,
at least one of $R_1$ to $R_{10}$ may each independently be a substituted or unsubstituted $C_2$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_7$-$C_{60}$ arylalkyl group, a substituted or unsubstituted $C_1$-$C_{60}$ heteroaryl group, a substituted or unsubstituted $C_1$-$C_{60}$ heteroaryloxy group, a substituted or unsubstituted $C_1$-$C_{60}$ heteroarylthio group, a substituted or unsubstituted $C_2$-$C_{60}$ heteroarylalkyl group, a substituted or unsubstituted monovalent non-aromatic condensed polycyclic group, a substituted or unsubstituted monovalent non-aromatic condensed heteropolycyclic group, $-N(Q_1)(Q_2)$, $-Si(Q_3)(Q_4)(Q_5)$, $-Ge(Q_3)(Q_4)(Q_5)$, $-B(Q_6)(Q_7)$, $-P(=O)(Q_8)(Q_9)$, or $-P(Q_8)(Q_9)$, $A_1$ to $A_6$ may each independently be a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_7$-$C_{60}$ arylalkyl group, a substituted or unsubstituted $C_1$-$C_{60}$ heteroaryl group, a substituted or unsubstituted $C_1$-$C_{60}$ heteroaryloxy group, a substituted or unsubstituted $C_1$-$C_{60}$ heteroarylthio group, a substituted or unsubstituted $C_2$-$C_{60}$ heteroarylalkyl group, a substituted or unsubstituted monovalent non-aromatic condensed polycyclic group, or a substituted or unsubstituted monovalent non-aromatic condensed heteropolycyclic group, two or more of $R_1$ to $R_{10}$ may optionally be linked to form a $C_5$-$C_{60}$ carbocyclic group unsubstituted or substituted with at least one $R_{1a}$ or a $C_1$-$C_{60}$ heterocyclic group unsubstituted or substituted at least one $R_{1a}$, two or more of $A_1$ to $A_6$ may optionally be linked to form a $C_5$-$C_{60}$ carbocyclic group unsubstituted or substituted with at least one $R_{1a}$ or a $C_1$-$C_{10}$ heterocyclic group unsubstituted or substituted with at least one $R_{1a}$, $R_{1a}$ is understood by referring to the detailed description of $R_7$, a substituent(s) of the substituted $C_1$-$C_{10}$ alkyl group, the substituted $C_2$-$C_{60}$ alkenyl group, the substituted $C_2$-$C_{60}$ alkynyl group, the substituted $C_1$-$C_{10}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_7$-$C_{60}$ arylalkyl group, the substituted $C_1$-$C_{10}$ heteroaryl group, the substituted $C_1$-$C_{10}$ heteroaryloxy group, the substituted $C_1$-$C_{10}$ heteroarylthio group, the substituted $C_2$-$C_{60}$ heteroarylalkyl group, the substituted monovalent non-aromatic condensed polycyclic group, and the substituted monovalent non-aromatic condensed heteropolycyclic group may each independently be:

deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_2$-$C_{60}$ alkenyl group, a $C_2$-$C_{60}$ alkynyl group, or a $C_1$-$C_{60}$ alkoxy group;

a $C_1$-$C_{60}$ alkyl group, a $C_2$-$C_{60}$ alkenyl group, a $C_2$-$C_{60}$ alkynyl group, or a $C_1$-$C_{60}$ alkoxy group, each substituted with deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ arylalkyl group, a $C_1$-$C_{60}$ heteroaryl group, a $C_1$-$C_{60}$ heteroaryloxy group, a $C_1$-$C_{60}$ heteroarylthio group, a $C_2$-$C_{60}$ heteroarylalkyl group, a monovalent non-aromatic condensed polycyclic group, a monovalent non-aromatic condensed heteropolycyclic group, $-N(Q_{11})(Q_{12})$, $-Si(Q_{13})(Q_{14})(Q_{15})$, $-Ge(Q_{13})(Q_{14})(Q_{15})$, $-B(Q_{16})(Q_{17})$, $-P(=O)(Q_{18})(Q_{19})$, $-P(Q_{18})(Q_{19})$, or any combination thereof;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ arylalkyl group, a $C_1$-$C_{60}$ heteroaryl group, a $C_1$-$C_{60}$ heteroaryloxy group, a $C_1$-$C_{60}$ heteroarylthio group, a $C_2$-$C_{60}$ heteroarylalkyl group, a monovalent non-aromatic condensed polycyclic group, or a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ arylalkyl group, a $C_1$-$C_{60}$ heteroaryl group, a $C_1$-$C_{60}$ heteroaryloxy group, a $C_1$-$C_{60}$ heteroarylthio group, a $C_2$-$C_{60}$ heteroarylalkyl group, a monovalent non-aromatic condensed polycyclic group, or a monovalent non-aromatic condensed heteropolycyclic group, each substituted with deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ arylalkyl group, a $C_1$-$C_{60}$ heteroaryl group, a $C_1$-$C_{60}$ heteroaryloxy group, a $C_1$-$C_{60}$ heteroarylthio group, a $C_2$-$C_{60}$ heteroarylalkyl group, a monovalent non-aromatic condensed polycyclic group, a monovalent non-aromatic condensed heteropolycyclic group, $-N(Q_{21})(Q_{22})$, $-Si(Q_{23})(Q_{24})(Q_{25})$, $-Ge(Q_{23})(Q_{24})(Q_{25})$, $-B(Q_{26})(Q_{27})$, $-P(=O)(Q_{28})(Q_{29})$, $-P(Q_{28})(Q_{29})$, or any combination thereof;

$-N(Q_{31})(Q_{32})$, $-Si(Q_{33})(Q_{34})(Q_{35})$, $-Ge(Q_{33})(Q_{34})(Q_{35})$, $-B(Q_{36})(Q_{37})$, $-P(=O)(Q_{38})(Q_{39})$, or $-P(Q_{38})(Q_{39})$; or any combination thereof, and $Q_1$ to $Q_9$, $Q_{11}$ to $Q_{19}$, $Q_{21}$ to $Q_{29}$, and $Q_{31}$ to $Q_{39}$ may each independently be hydrogen; deuterium; —F; —Cl; —Br; —I; a hydroxyl group; a cyano group; a nitro group; an amino group; an amidino group; a hydrazine group; a hydrazone group; a carboxylic acid group or a salt thereof; a sulfonic acid group or a salt thereof; a phosphoric acid group or a salt thereof; a $C_1$-$C_{60}$ alkyl group; a $C_2$-$C_{60}$ alkenyl group; a $C_2$-$C_{60}$ alkynyl group; a $C_1$-$C_{60}$ alkoxy group; a $C_3$-$C_{10}$ cycloalkyl group; a $C_1$-$C_{10}$ heterocycloalkyl group; a $C_3$-$C_{10}$ cycloalkenyl group; a $C_1$-$C_{10}$ heterocycloalkenyl group; a $C_6$-$C_{60}$ aryl group; a $C_6$-$C_{60}$ aryl group substituted with a $C_1$-$C_{60}$ alkyl group, a $C_6$-$C_{60}$ aryl group, or any combination thereof; a $C_6$-$C_{60}$ aryloxy group; a $C_6$-$C_{60}$ arylthio group; a $C_7$-$C_{60}$ arylalkyl group; a $C_1$-$C_{60}$ heteroaryl group; a $C_1$-$C_{60}$ heteroaryloxy group; a $C_1$-$C_{60}$ heteroarylthio group; a $C_2$-$C_{60}$ heteroarylalkyl group; a monovalent non-aromatic condensed polycyclic group, or a monovalent non-aromatic condensed heteropolycyclic group.

Another aspect of the present disclosure provides an organic light-emitting device including:

a first electrode, a second electrode, and an organic layer disposed between the first electrode and the second electrode, wherein the organic layer includes an emission layer, and wherein the organic layer includes at least one organometallic compound represented by Formula 1.

Another aspect of the present disclosure provides a diagnostic composition including at least one organometallic compound represented by Formula 1.

BRIEF DESCRIPTION OF THE DRAWING

These and/or other aspects will become apparent and more readily appreciated from the following description of the embodiments, taken in conjunction with the FIGURE which is a schematic view of an organic light-emitting device according to an embodiment.

DETAILED DESCRIPTION

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the FIGURES, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the FIGURES, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

It will be understood that when an element is referred to as being "on" another element, it can be directly in contact with the other element or intervening elements may be present therebetween. In contrast, when an element is referred to as being "directly on" another element, there are no intervening elements present.

It will be understood that, although the terms first, second, third etc. may be used herein to describe various elements, components, regions, layers, and/or sections, these elements, components, regions, layers, and/or sections should not be limited by these terms. These terms are only used to distinguish one element, component, region, layer, or section from another element, component, region, layer, or section. Thus, a first element, component, region, layer, or section discussed below could be termed a second element, component, region, layer, or section without departing from the teachings of the present embodiments.

The terminology used herein is for the purpose of describing particular embodiments only and is not intended to be limiting. As used herein, the singular forms "a," "an," and "the" are intended to include the plural forms as well, unless the context clearly indicates otherwise.

The term "or" means "and/or." It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art to which this general inventive concept belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

"About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" can mean within one or more standard deviations, or within ±30%, 20%, 10%, 5% of the stated value.

An aspect of the present disclosure provides an organometallic compound represented by Formula 1 below:

Formula 1

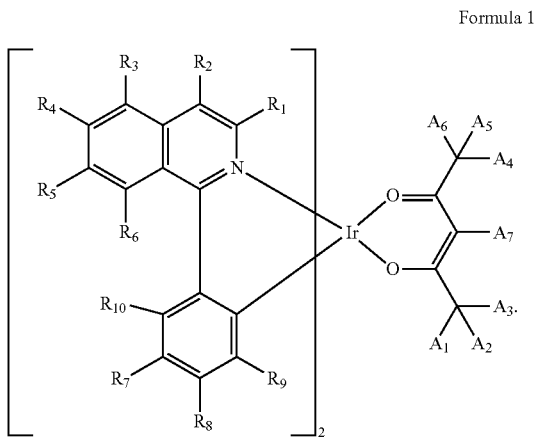

In Formula 1,
R$_1$ to R$_{10}$ and A$_7$ may each independently be hydrogen, deuterium, —F, —Cl, —Br, —I, —SF$_5$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted C$_1$-C$_{60}$ alkyl group, a substituted or unsubstituted C$_2$-C$_{60}$ alkenyl group, a substituted or unsubstituted C$_2$-C$_{60}$ alkynyl group, a substituted or unsubstituted C$_1$-C$_{60}$ alkoxy group, a substituted or unsubstituted C$_3$-C$_{10}$ cycloalkyl group, a substituted or unsubstituted heterocycloalkyl group, a substituted or unsubstituted C$_3$-C$_{10}$ cycloalkenyl group, a substituted or unsubstituted heterocycloalkenyl group, a substituted or unsubstituted C$_6$-C$_{60}$ aryl group, a substituted or unsubstituted C$_6$-C$_{60}$ aryloxy group, a substituted or unsubstituted C$_6$-C$_{60}$ arylthio group, a substituted or unsubstituted C$_7$-C$_{60}$ arylalkyl group, a substituted or unsubstituted C$_1$-C$_{60}$ heteroaryl group, a substituted or unsubstituted C$_1$-C$_{60}$ heteroaryloxy group, a substituted or unsubstituted C$_1$-C$_{60}$ heteroarylthio group, a substituted or unsubstituted C$_2$-C$_{60}$ heteroarylalkyl group, a substituted or unsubstituted monovalent non-aromatic condensed polycyclic group, a substituted or unsubstituted monovalent non-aromatic condensed heteropolycyclic group, —N(Q$_1$)(Q$_2$), —Si(Q$_3$)(Q$_4$)(Q$_5$), —Ge(Q$_3$)(Q$_4$)(Q$_5$), —B(Q$_6$)(Q$_7$), —P(=O)(Q$_8$)(C)$_9$), or —P(Q$_8$)(Q$_9$), at least one of R$_1$ to R$_{10}$ (for example, at least one of R$_1$ to R$_6$) may each independently be a substituted or unsubstituted C$_2$-C$_{60}$ alkyl group, a substituted or unsubstituted C$_2$-C$_{60}$ alkenyl group, a substituted or unsubstituted C$_2$-C$_{60}$ alkynyl group, a substituted or unsubstituted C$_1$-C$_{60}$ alkoxy group, a substituted or unsubstituted C$_3$-C$_{10}$ cycloalkyl group, a substituted or unsubstituted C$_1$-C$_{10}$ heterocycloalkyl group, a substituted or unsubstituted C$_3$-C$_{10}$ cycloalkenyl group, a substituted or unsubstituted C$_1$-C$_{10}$ heterocycloalkenyl group, a substituted or unsubstituted C$_6$-C$_{60}$ aryl group, a substituted or unsubstituted C$_6$-C$_{60}$ aryloxy group, a substituted or unsubstituted C$_6$-C$_{60}$ arylthio group, a substituted or unsubstituted C$_7$-C$_{60}$ arylalkyl group, a substituted or unsubstituted C$_1$-C$_{60}$ heteroaryl group, a substituted or unsubstituted C$_1$-C$_{60}$ heteroaryloxy group, a substituted or unsubstituted C$_1$-C$_{60}$ heteroarylthio group, a substituted or unsubstituted C$_2$-C$_{60}$ heteroarylalkyl group, a substituted or unsubstituted monovalent non-aromatic condensed polycyclic group, a substituted or unsubstituted monovalent non-aromatic condensed heteropolycyclic group, —N(Q$_1$)(Q$_2$), —Si(Q$_3$)(Q$_4$)(Q$_5$), —Ge(Q$_3$)(Q$_4$)(Q$_5$), —B(Q$_6$)(Q$_7$), —P(=O)(Q$_8$)(Q$_9$), or —P(Q$_8$)(Q$_9$), and A$_1$ to A$_6$ may each independently be a substituted or unsubstituted C$_1$-C$_{60}$ alkyl group, a substituted or unsubstituted C$_2$-C$_{60}$ alkenyl group, a substituted or unsubstituted C$_2$-C$_{60}$ alkynyl group, a substituted or unsubstituted C$_1$-C$_{60}$ alkoxy group, a substituted or unsubstituted C$_3$-C$_{10}$ cycloalkyl group, a substituted or unsubstituted C$_1$-C$_{10}$ heterocycloalkyl group, a substituted or unsubstituted C$_3$-C$_{10}$ cycloalkenyl group, a substituted or unsubstituted C$_1$-C$_{10}$ heterocycloalkenyl group, a substituted or unsubstituted C$_6$-C$_{60}$ aryl group, a substituted or unsubstituted C$_6$-C$_{60}$ aryloxy group, a substituted or unsubstituted C$_6$-C$_{60}$ arylthio group, a substituted or unsubstituted C$_7$-C$_{60}$ arylalkyl group, a substituted or unsubstituted C$_1$-C$_{60}$ heteroaryl group, a substituted or unsubstituted C$_1$-C$_{60}$ heteroaryloxy group, a substituted or unsubstituted C$_1$-C$_{60}$ heteroarylthio group, a substituted or unsubstituted C$_2$-C$_{60}$ heteroarylalkyl group, a substituted or unsubstituted monovalent non-aromatic condensed polycyclic group, or a substituted or unsubstituted monovalent non-aromatic condensed heteropolycyclic group.

Q$_1$ to Q$_9$ are the same as described herein.

In an embodiment, Formula 1,

R$_1$ to R$_{10}$ and A$_7$ may each independently be hydrogen, deuterium, a cyano group, a substituted or unsubstituted C$_1$-C$_{60}$ alkyl group, or a substituted or unsubstituted C$_3$-C$_{10}$ cycloalkyl group and/or at least one of R$_1$ to R$_{10}$ (for example, at least one of R$_1$ to R$_6$) may each independently be a substituted or unsubstituted C$_2$-C$_{60}$ alkyl group, or a substituted or unsubstituted C$_3$-C$_{10}$ cycloalkyl group, and/or A$_1$ to A$_6$ may each independently be a substituted or unsubstituted C$_1$-C$_{60}$ alkyl group or a substituted or unsubstituted C$_3$-C$_{10}$ cycloalkyl group.

In one or more embodiments, R$_1$ to R$_{10}$ and A$_7$ in Formula 1 may each independently be:

hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, —SF$_5$, C$_1$-C$_{20}$ alkyl group, or a C$_1$-C$_{20}$ alkoxy group;

a C$_1$-C$_{20}$ alkyl group or a C$_1$-C$_{20}$ alkoxy group, each substituted with deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a C$_1$-C$_{10}$ alkyl group, a C$_1$-C$_{20}$ alkoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a bicyclo[1.1.1]pentyl group, a bicyclo[2.1.1]hexyl group, a bicyclo[2.2.1]heptyl group, a bicyclo[2.2.2]octyl group, a phenyl group, a (C$_1$-C$_{20}$ alkyl)phenyl group, a biphenyl group, a terphenyl group, a naphthyl group, a pyridinyl group, a pyrimidinyl group, or any combination thereof;

a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a bicyclo[1.1.1]pentyl group, a bicyclo[2.1.1]hexyl group, a bicyclo[2.2.1]heptyl group, a bicyclo[2.2.2]octyl group, a phenyl group, a ($C_1$-$C_{20}$ alkyl) phenyl group, a biphenyl group, a terphenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, or an imidazopyrimidinyl group, each unsubstituted or substituted with deuterium, —F, —Cl, —Br, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{20}$ alkoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a bicyclo[1.1.1]pentyl group, a bicyclo[2.1.1]hexyl group, a bicyclo[2.2.1]heptyl group, a bicyclo[2.2.2]octyl group, a phenyl group, a ($C_1$-$C_{20}$ alkyl)phenyl group, a biphenyl group, a terphenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, an imidazopyrimidinyl group, or any combination thereof;

—N($Q_1$)($Q_2$), —Si($Q_3$)($Q_4$)($Q_5$), —B($Q_6$)($Q_7$), or —P(=O)($Q_9$)($Q_9$), or any combination thereof.

$Q_1$ to $Q_9$ are the same as described herein.

In one or more embodiments, $R_1$ to $R_{10}$ and $A_7$ in Formula 1 may each independently be:

hydrogen, deuterium, —F, a cyano group, a methyl group, an ethyl group, an n-propyl group, an isopropyl group, an n-butyl group, a sec-butyl group, an isobutyl group, a tert-butyl group, an n-pentyl group, a tert-pentyl group, a neopentyl group, an isopentyl group, a sec-pentyl group, a 3-pentyl group, a sec-isopentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an isononyl group, a sec-nonyl group, a tert-nonyl group, an n-decyl group, an isodecyl group, a sec-decyl group, a tert-decyl group, a methoxy group, an ethoxy group, a propoxy group, a butoxy group, a pentoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a bicyclo[1.1.1]pentyl group, a bicyclo[2.1.1]hexyl group, a bicyclo[2.2.1]heptyl group, a bicyclo[2.2.2]octyl group, a phenyl group, a biphenyl group, a terphenyl group, a naphthyl group, a pyridinyl group, a pyrimidinyl group, a carbazolyl group, a fluorenyl group, a dibenzosilolyl group, a dibenzofuranyl group, a dibenzothiophenyl group, or —Si($Q_3$)($Q_4$)($Q_5$);

a methyl group, an ethyl group, an n-propyl group, an isopropyl group, an n-butyl group, a sec-butyl group, an isobutyl group, a tert-butyl group, an n-pentyl group, a tert-pentyl group, a neopentyl group, an isopentyl group, a sec-pentyl group, a 3-pentyl group, a sec-isopentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an isononyl group, a sec-nonyl group, a tert-nonyl group, an n-decyl group, an isodecyl group, a sec-decyl group, or a tert-decyl group, each substituted with deuterium, —F, a cyano group, or any combination thereof; or a methoxy group, an ethoxy group, a propoxy group, a butoxy group, a pentoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a bicyclo[1.1.1]pentyl group, a bicyclo[2.1.1]hexyl group, a bicyclo[2.2.1]heptyl group, a bicyclo[2.2.2]octyl group, a phenyl group, a biphenyl group, a terphenyl group, a naphthyl group, a pyridinyl group, a pyrimidinyl group, a carbazolyl group, a fluorenyl group, a dibenzosilolyl group, a dibenzofuranyl group, or a dibenzothiophenyl group, each substituted with deuterium, —F, a cyano group, a $C_1$-$C_{10}$ alkyl group, or any combination thereof.

$Q_3$ to $Q_5$ are the same as described herein.

In one or more embodiments, at least one of $R_1$ to $R_{10}$ (for example, at least one of $R_1$ to $R_6$/in an embodiment, $R_4$) in Formula 1 may each independently be:

a $C_2$-$C_{20}$ alkyl group or a $C_1$-$C_{20}$ alkoxy group, each unsubstituted or substituted with deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid group or a salt thereof, sulfonic acid group or a salt thereof, a phosphoric acid group or a salt thereof, a $C_1$-$C_{10}$ alkyl group, a $C_1$-$C_{20}$ alkoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a bicyclo[1.1.1]pentyl group, a bicyclo[2.1.1]hexyl group, a bicyclo[2.2.1]heptyl group, a bicyclo[2.2.2]octyl group, a phenyl group, a ($C_1$-$C_{20}$ alkyl)phenyl group, a biphenyl group, a terphenyl group, a naphthyl group, a pyridinyl group, a pyrimidinyl group, or any combination thereof;

a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a bicyclo[1.1.1]pentyl group, a bicyclo[2.1.1]hexyl group, a bicyclo[2.2.1]heptyl group, a bicyclo[2.2.2]octyl group, a phenyl group, a ($C_1$-$C_{20}$ alkyl)phenyl group, a biphenyl group, a terphenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, or an imidazopyrimidinyl group, each unsubstituted or substituted with deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{20}$ alkoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a bicyclo[1.1.1]pentyl group, a bicyclo[2.1.1]hexyl group, a bicyclo[2.2.1]heptyl group, a bicyclo[2.2.2]octyl group, a phenyl group, a ($C_1$-$C_{20}$ alkyl)phenyl group, a biphenyl group, a terphenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, an imidazopyrimidinyl group, or any combination thereof;

—N($Q_1$)($Q_2$), —Si($Q_3$)($Q_4$)($Q_5$), —B($Q_6$)($Q_7$), or —P(=O)($Q_8$)($Q_9$), or any combination thereof.

$Q_1$ to $Q_6$ are the same as described herein.

In one or more embodiments, at least one of $R_1$ to $R_{10}$ (for example, at least one of $R_1$ to $R_6$/in an embodiment, $R_4$) Formula 1 may each independently be:

an ethyl group, an n-propyl group, an isopropyl group, an n-butyl group, a sec-butyl group, an isobutyl group, a tert-butyl group, an n-pentyl group, a tert-pentyl group, a neopentyl group, an isopentyl group, a sec-pentyl group, a 3-pentyl group, a sec-isopentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an isononyl group, a sec-nonyl group, a tert-nonyl group, an n-decyl group, an isodecyl group, a sec-decyl group, a tert-decyl group, a methoxy group, an ethoxy group, a propoxy group, a butoxy group, a pentoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a bicyclo[1.1.1]pentyl group, a bicyclo[2.1.1]hexyl group, a bicyclo[2.2.1]heptyl group, a bicyclo[2.2.2]octyl group, a phenyl group, a biphenyl group, a terphenyl group, a naphthyl group, a pyridinyl group, a pyrimidinyl group, a carbazolyl group, a fluorenyl group, a dibenzosilolyl group, a dibenzofuranyl group, a dibenzothiophenyl group, or —Si($Q_3$)($Q_4$)($Q_5$);

an ethyl group, an n-propyl group, an isopropyl group, an n-butyl group, a sec-butyl group, an isobutyl group, a tert-butyl group, an n-pentyl group, a tert-pentyl group, a neopentyl group, an isopentyl group, a sec-pentyl group, a 3-pentyl group, a sec-isopentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an isononyl group, a sec-nonyl group, a tert-nonyl group, an n-decyl group, an isodecyl group, a sec-decyl group, or a tert-decyl group, each substituted with deuterium, —F, a cyano group, or any combination thereof; or a methoxy group, an ethoxy group, a propoxy group, a butoxy group, a pentoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a bicyclo[1.1.1]pentyl group, a bicyclo[2.1.1]hexyl group, a bicyclo[2.2.1]heptyl group, a bicyclo[2.2.2]octyl group, a phenyl group, a biphenyl group, a terphenyl group, a naphthyl group, a pyridinyl group, a pyrimidinyl group, a carbazolyl group, a fluorenyl group, a dibenzosilolyl group, a dibenzofuranyl group, or a dibenzothiophenyl group, each substituted with deuterium, —F, a cyano group, a $C_1$-$C_{10}$ alkyl group, or any combination thereof.

$Q_3$ to $Q_5$ are the same as described herein.

In one or more embodiments, $A_1$ to $A_6$ in Formula 1 may each independently be:

a $C_1$-$C_{20}$ alkyl group or a $C_1$-$C_{20}$ alkoxy group, each unsubstituted or substituted with deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{20}$ alkoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a bicyclo[1.1.1]pentyl group, a bicyclo[2.1.1]hexyl group, a bicyclo[2.2.1]heptyl group, a bicyclo[2.2.2]octyl group, a phenyl group, a ($C_1$-$C_{20}$ alkyl)phenyl group, a biphenyl group, a terphenyl group, a naphthyl group, a pyridinyl group, a pyrimidinyl group, or any combination thereof; or a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a bicyclo[1.1.1]pentyl group, a bicyclo[2.1.1]hexyl group, a bicyclo[2.2.1]heptyl group, a bicyclo[2.2.2]octyl group, a phenyl group, a ($C_1$-$C_{20}$ alkyl)phenyl group, a biphenyl group, a terphenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, or an imidazopyrimidinyl group, each unsubstituted or substituted with deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{20}$ alkoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a bicyclo[1.1.1]pentyl group, a bicyclo[2.1.1]hexyl group, a bicyclo[2.2.1]heptyl group, a bicyclo[2.2.2]octyl group, a phenyl group, a ($C_1$-$C_{20}$ alkyl)phenyl group, a biphenyl group, a terphenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, an imidazopyrimidinyl group, or any combination thereof.

In one or more embodiments, $A_1$ to $A_6$ in Formula 1 may each independently be:

a methyl group, an ethyl group, an n-propyl group, an isopropyl group, an n-butyl group, a sec-butyl group, an isobutyl group, a tert-butyl group, an n-pentyl group, a tert-pentyl group, a neopentyl group, an isopentyl group, a sec-pentyl group, a 3-pentyl group, a sec-isopentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an isononyl group, a sec-nonyl group, a tert-nonyl group, an n-decyl group, an isodecyl group, a sec-decyl group, a tert-decyl group, a methoxy group, an ethoxy group, a propoxy group, a butoxy group, a pentoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a bicyclo[1.1.1]pentyl group, a bicyclo[2.1.1]hexyl group, a bicyclo[2.2.1]heptyl group, a bicyclo[2.2.2]octyl group, a phenyl group, a biphenyl group, a terphenyl group, a naphthyl group, a pyridinyl group, a pyrimidinyl group, a carbazolyl group, a fluorenyl group, a dibenzosilolyl group, a dibenzofuranyl group or a dibenzothiophenyl group;

a methyl group, an ethyl group, an n-propyl group, an isopropyl group, an n-butyl group, a sec-butyl group, an isobutyl group, a tert-butyl group, an n-pentyl group, a tert-pentyl group, a neopentyl group, an isopentyl group, a sec-pentyl group, a 3-pentyl group, a sec-isopentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an isononyl group, a sec-nonyl group, a tert-nonyl group, an n-decyl group, an isodecyl group, a sec-decyl group, or a tert-decyl group, each substituted with deuterium, —F, a cyano group, or any combination thereof; or a methoxy group, an ethoxy group, a propoxy group, a butoxy group, a pentoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a bicyclo[1.1.1]pentyl group, a bicyclo[2.1.1]hexyl group, a bicyclo[2.2.1]heptyl group, a bicyclo[2.2.2]octyl group, a phenyl group, a biphenyl group, a terphenyl group, a naphthyl group, a pyridinyl group, a pyrimidinyl group, a carbazolyl group, a fluorenyl group, a dibenzosilolyl group, a dibenzofuranyl group, or a dibenzothiophenyl group, each substituted with deuterium, —F, a cyano group, a $C_1$-$C_{10}$ alkyl group, or any combination thereof.

$Q_3$ to $Q_5$ are the same as described herein.

For example, $Q_1$ to $Q_9$ may each independently be:
—$CH_3$, —$CD_3$, —$CD_2H$, —$CDH_2$, —$CH_2CH_3$, —$CH_2CD_3$, —$CH_2CD_2H$, —$CH_2CDH_2$, —$CHDCH_3$, —$CHDCD_2H$, —$CHDCDH_2$, —$CHDCD_3$, —$CD_2CD_3$, —$CD_2CD_2H$, or —$CD_2CDH_2$, or an n-propyl group, an isopropyl group, an n-butyl group, a sec-butyl group, an isobutyl group, a tert-butyl group, an n-pentyl group, a tert-pentyl group, a neopentyl group, an isopentyl group, a sec-pentyl group, a 3-pentyl group, a sec-isopentyl group, a phenyl group, a biphenyl group, or a naphthyl group, each unsubstituted or substituted with deuterium, a $C_1$-$C_{10}$ alkyl group, a phenyl group, or any combination thereof, but embodiments of the present disclosure are not limited thereto.

In one or more embodiments, in Formula 1, $R_1$ to $R_{10}$ and $A_7$ may each independently be hydrogen, deuterium, —F, a cyano group, a nitro group, —$SF_5$, —$CH_3$, —$CD_3$, —$CD_2H$, —$CDH_2$, —$CF_3$, —$CF_2H$, —$CFH_2$, a group represented by one of Formulae 9-1 to 9-66, a group represented by one of Formulae 9-1 to 9-66 in which at least one hydrogen is substituted with deuterium, a group represented by one of Formulae 10-1 to 10-249, a group represented by one of Formulae 10-1 to 10-249 in which at least one hydrogen is substituted with deuterium, —Si($Q_3$)($Q_4$)($Q_5$), or —Ge($Q_3$)($Q_4$)($Q_5$) (wherein $Q_3$ to $Q_5$ are the same as described herein), and/or at least one of $R_1$ to $R_{10}$ (for example, at least one of $R_1$ to $R_6$) may each independently be a group represented by one of Formulae 9-1 to 9-66, a group represented by one of Formulae 9-1 to 9-66 in which at least one hydrogen is substituted with deuterium, a group represented by one of Formulae 10-1 to 10-249, a group represented by one of Formulae 10-1 to 10-249 in which at least one hydrogen is substituted with deuterium, —Si($Q_3$)($Q_4$)($Q_5$), or —Ge($Q_3$)($Q_4$)($Q_5$) (wherein $Q_3$ to $Q_5$ are the same as described herein), and/or $A_1$ to $A_6$ may each independently be —$CH_3$, —$CD_3$, —$CD_2H$, —$CDH_2$, —$CF_3$, —$CF_2H$, —$CFH_2$, a group represented by one of Formulae 9-1 to 9-66, a group represented by one of Formulae 9-1 to 9-66 in which at least one hydrogen is substituted with deuterium, a group represented by one of Formulae 10-1 to 10-249, or a group represented by one of Formulae 10-1 to 10-249 in which at least one hydrogen is substituted with deuterium, but embodiments of the present disclosure are not limited thereto:

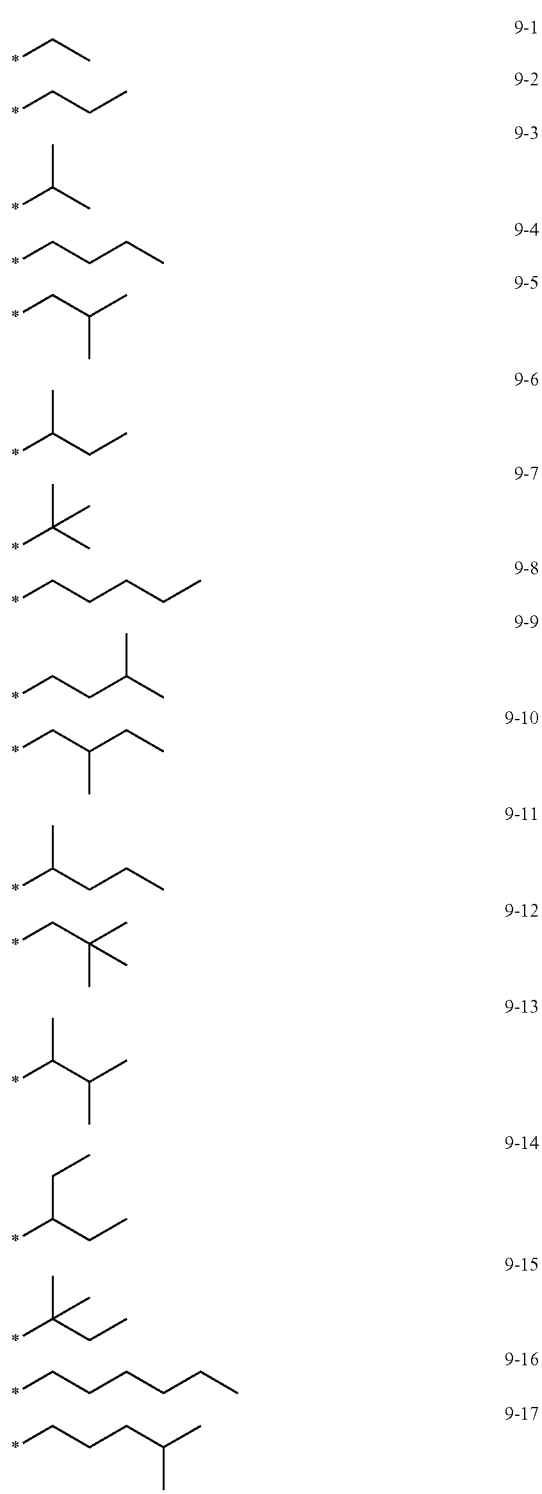

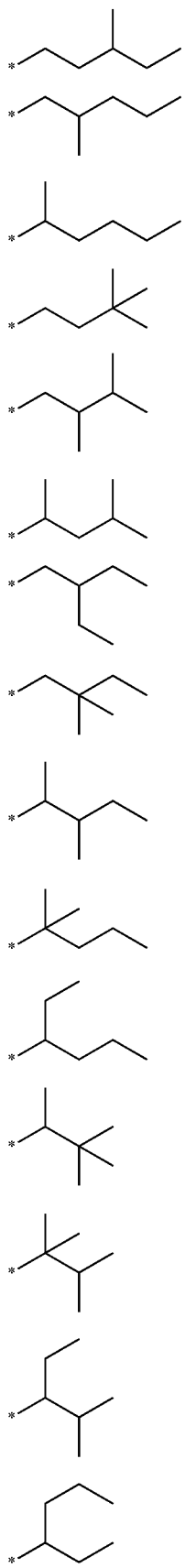
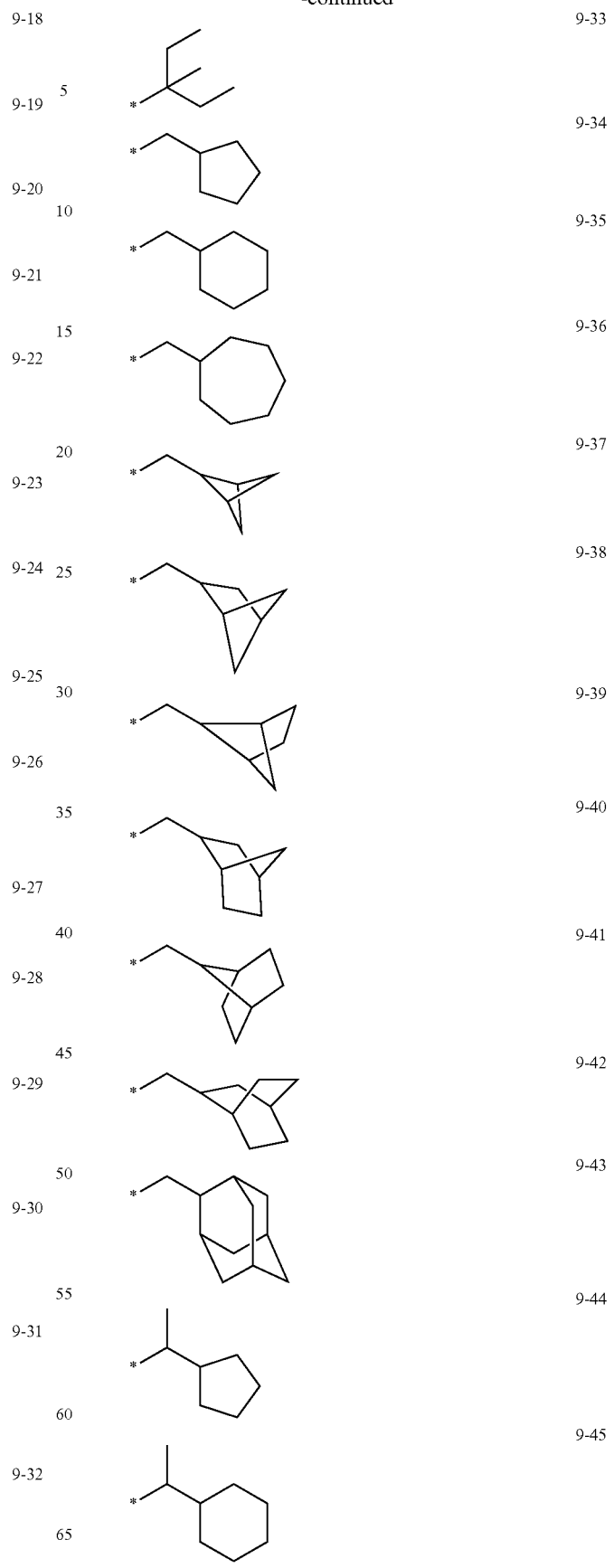

9-46 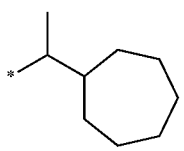
9-47 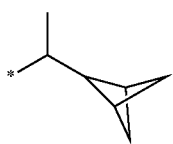
9-48 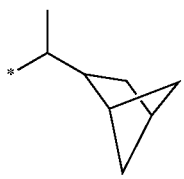
9-49 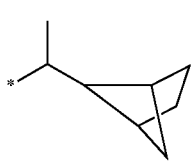
9-50 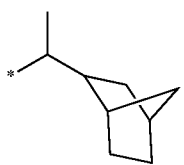
9-51 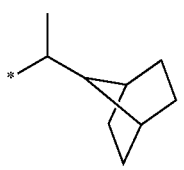
9-52 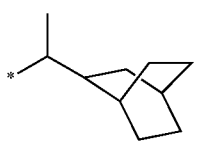
9-53 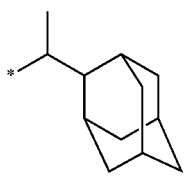
9-54 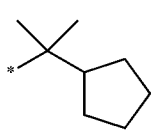
9-55 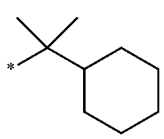
9-56 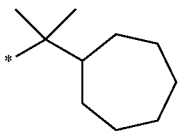
9-57 
9-58 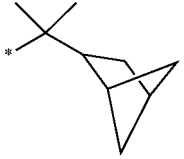
9-59 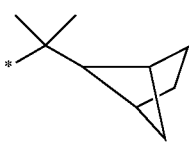
9-60 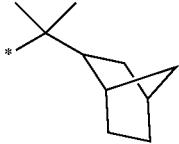
9-61 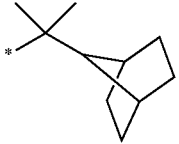
9-62 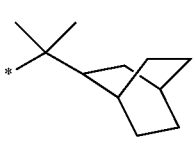
9-63 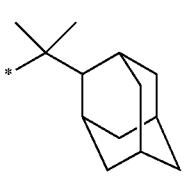
9-64 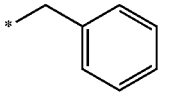
9-65 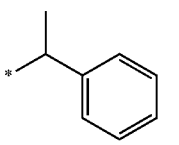
9-66 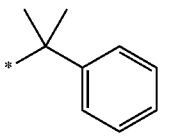

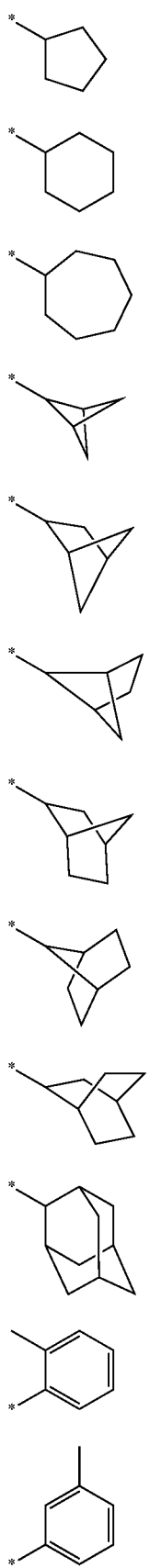
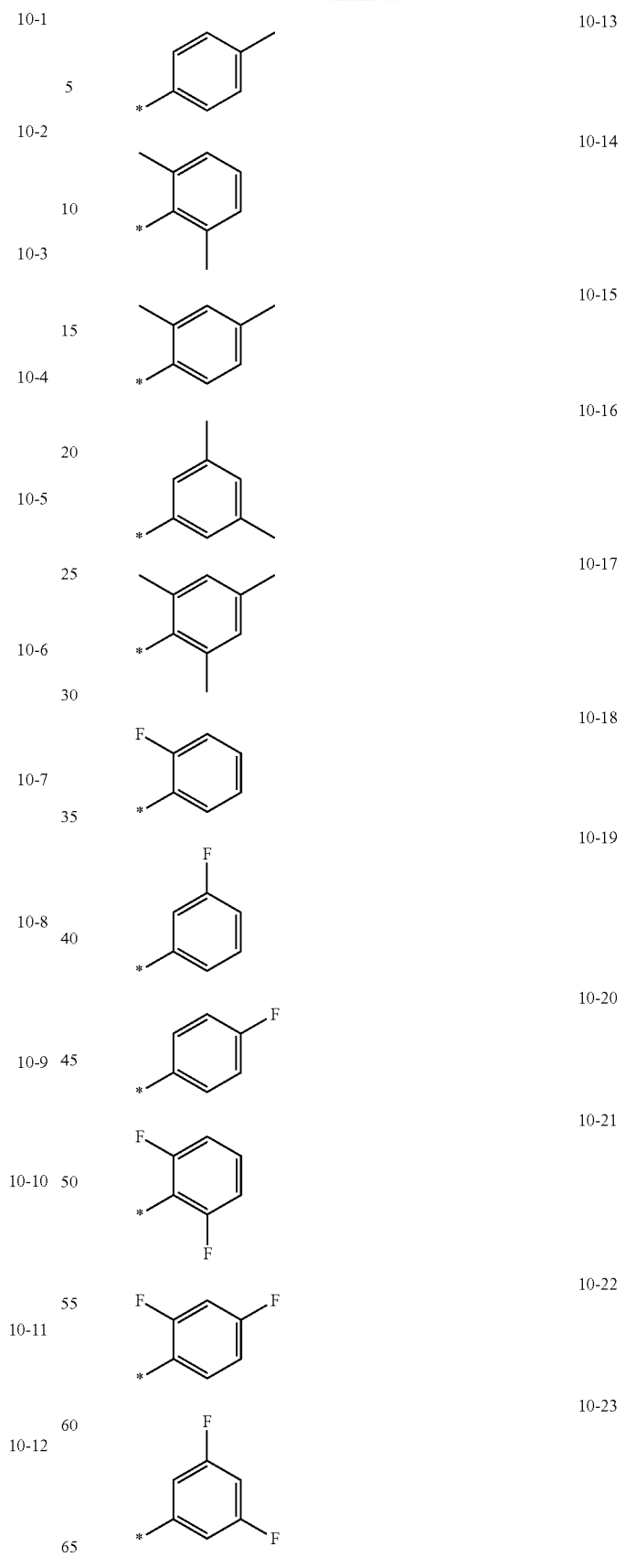

-continued
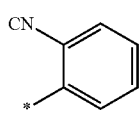 10-25
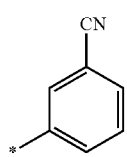 10-26
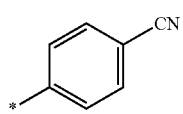 10-27
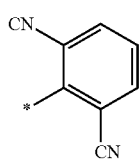 10-28
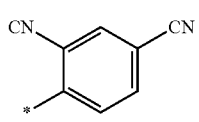 10-29
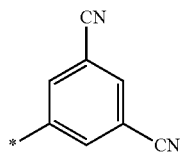 10-30
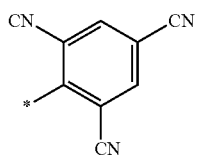 10-31
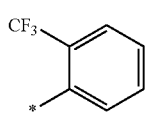 10-32
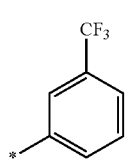 10-33
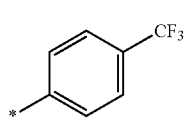 10-34
-continued
10-24 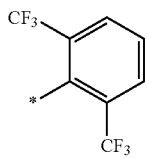
10-25 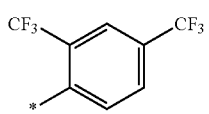
10-26 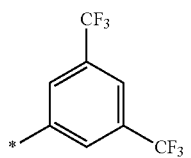
10-27 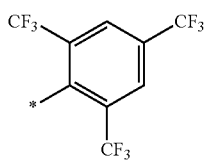
10-28 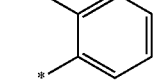
10-29 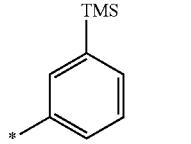
10-30 10-40
10-31 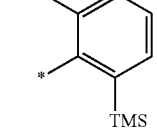
10-32 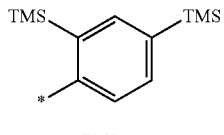
10-33 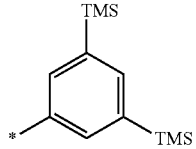
10-34 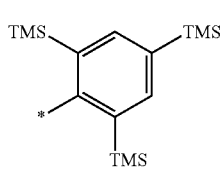
10-35
10-36
10-37
10-38
10-39
10-40
10-41
10-42
10-43
10-44
10-45

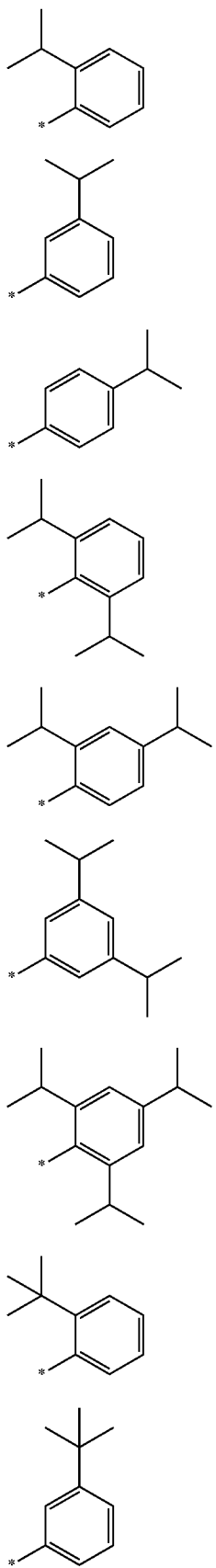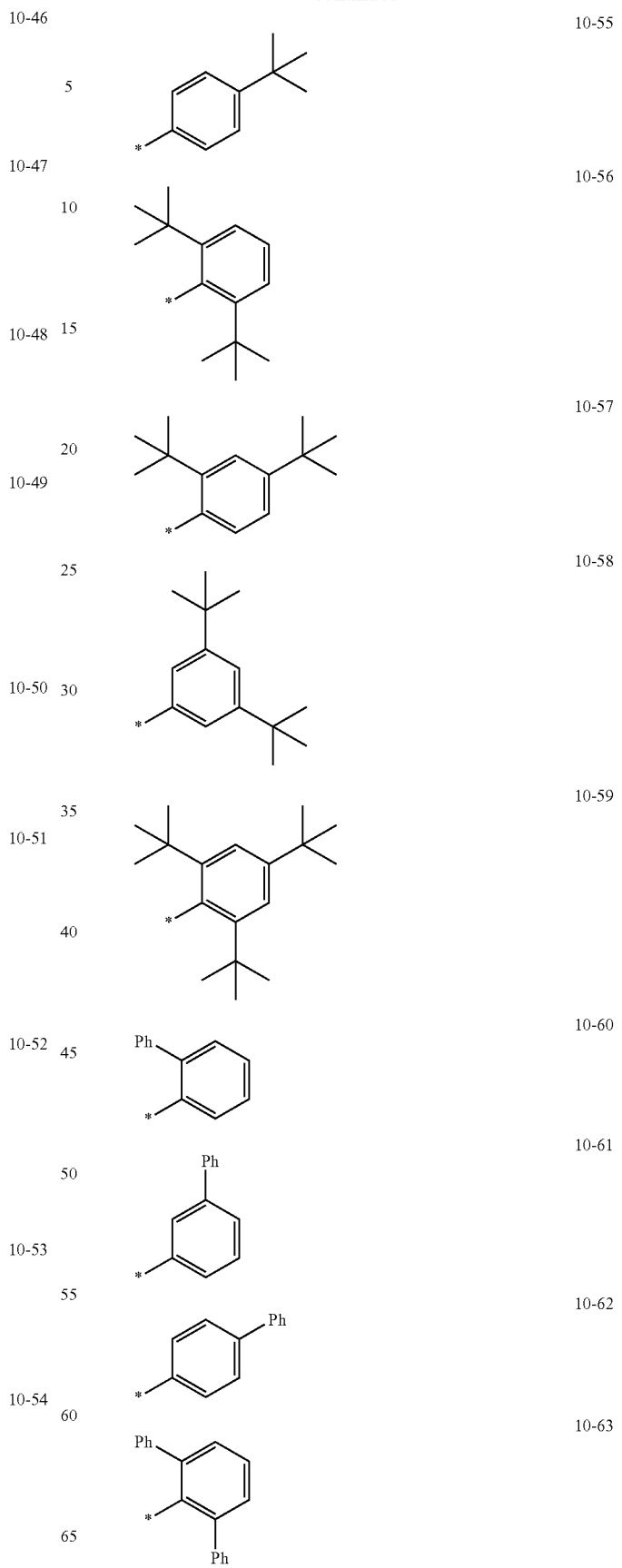

10-64 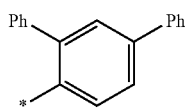
10-65 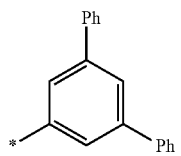
10-66 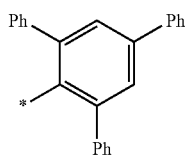
10-67 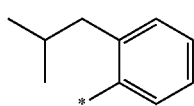
10-68 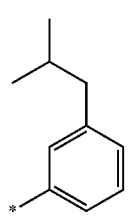
10-69 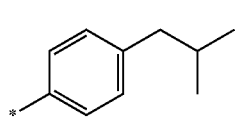
10-70 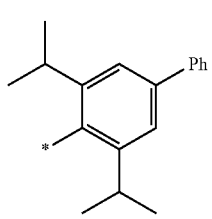
10-71 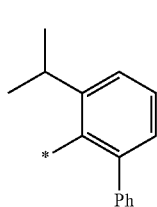
10-72 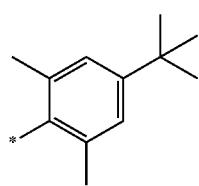
10-73 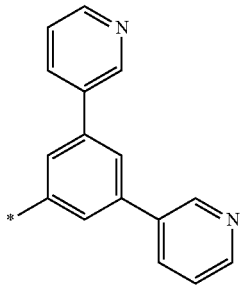
10-74 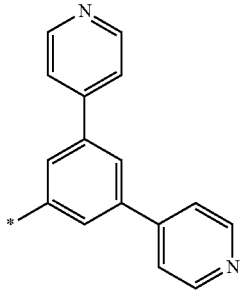
10-75 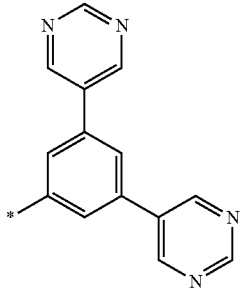
10-76 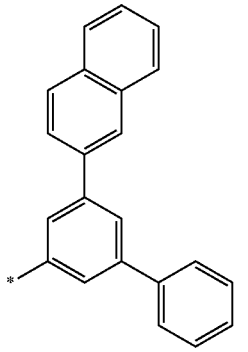
10-77 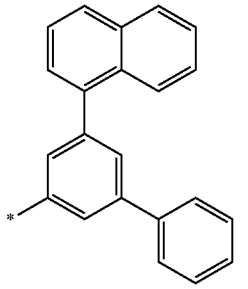

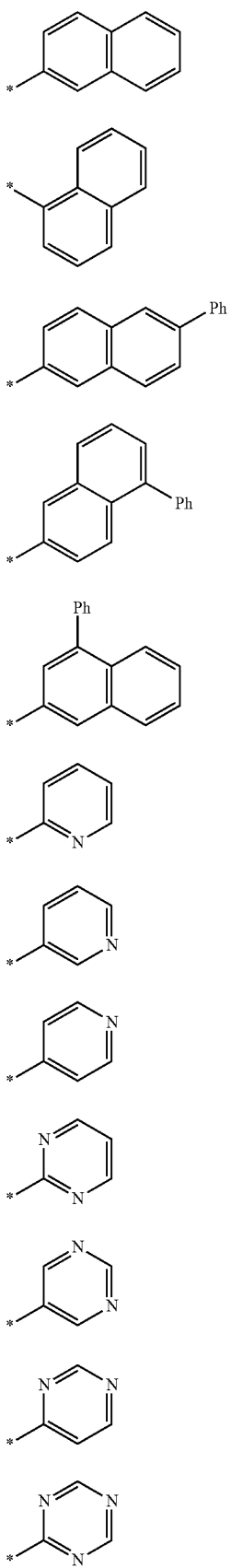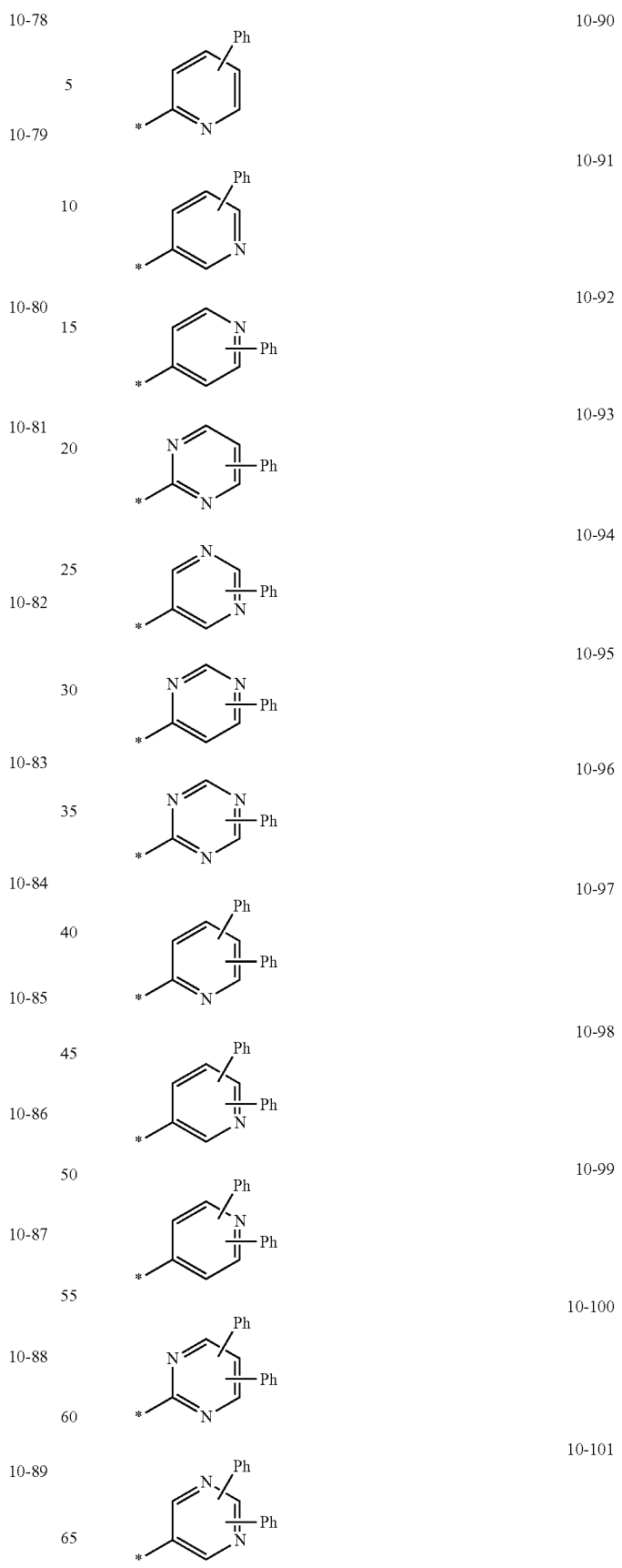

-continued
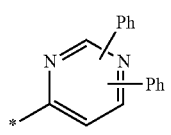
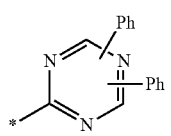
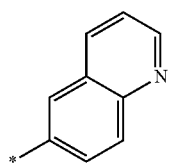
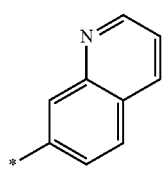
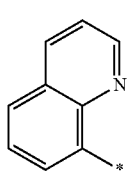
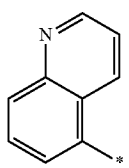
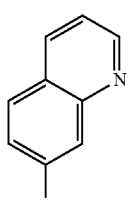
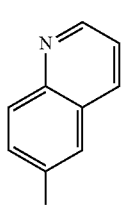
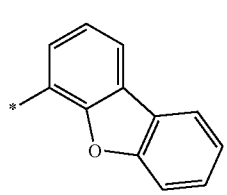
-continued
10-102
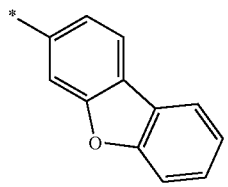
10-103
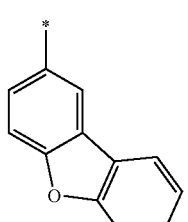
10-104
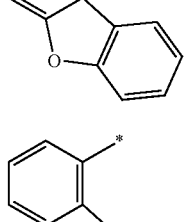
10-105
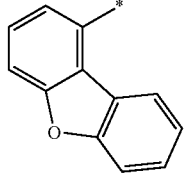
10-106
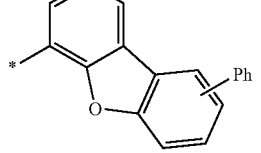
10-107
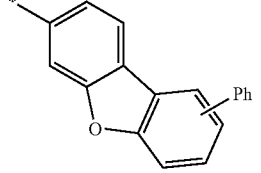
10-108
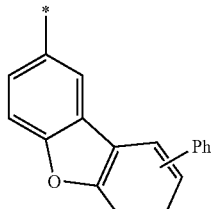
10-109
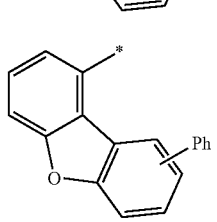
10-110
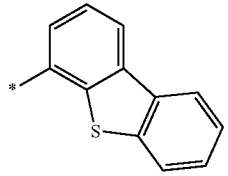
10-111
10-112
10-113
10-114
10-115
10-116
10-117
10-118

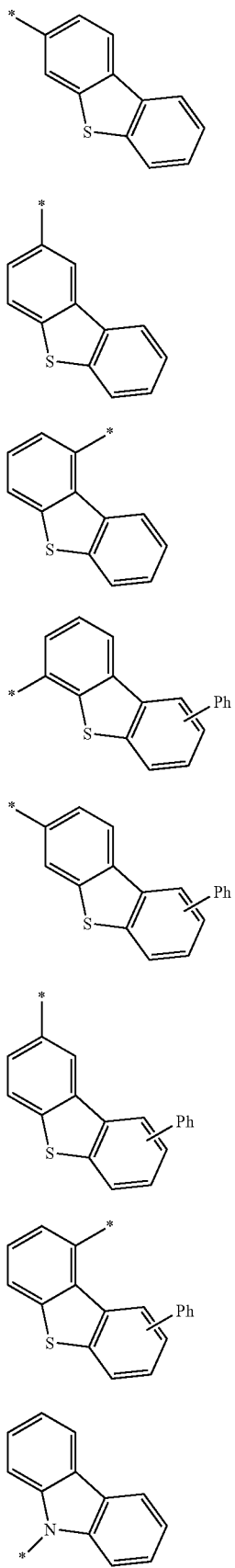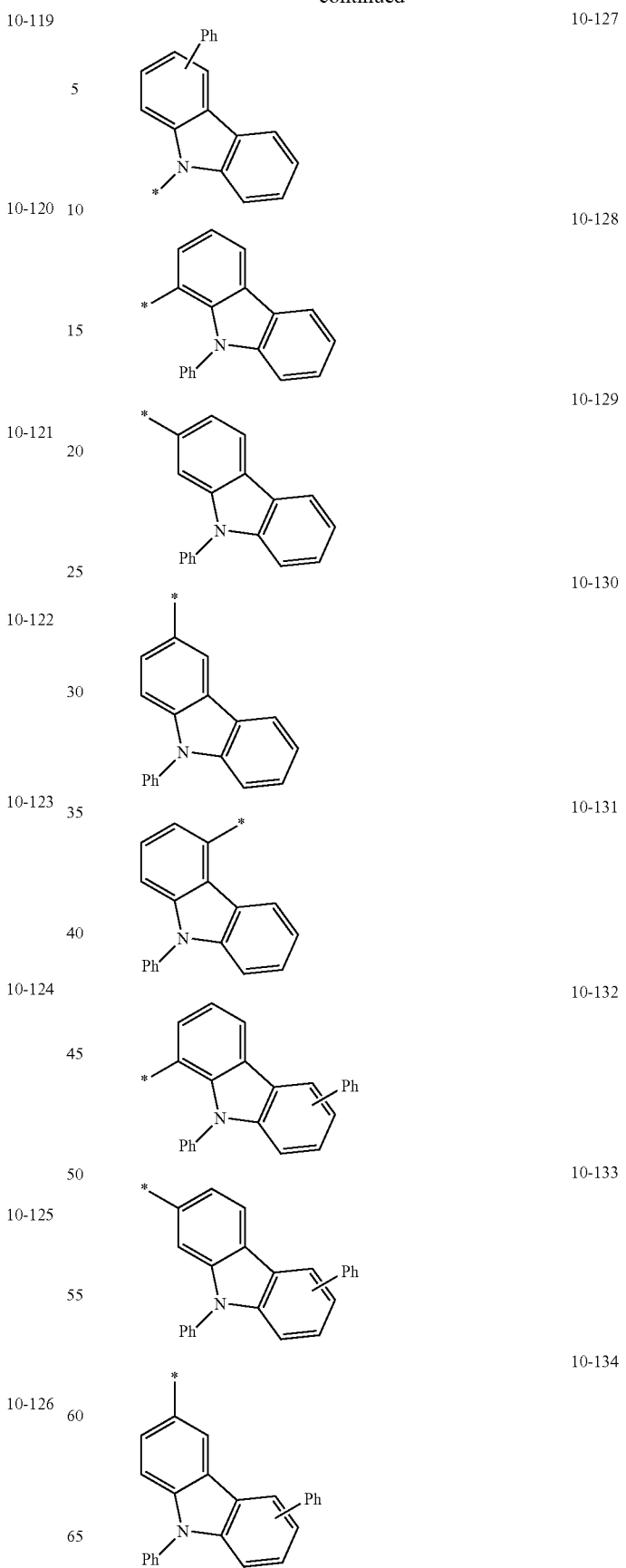

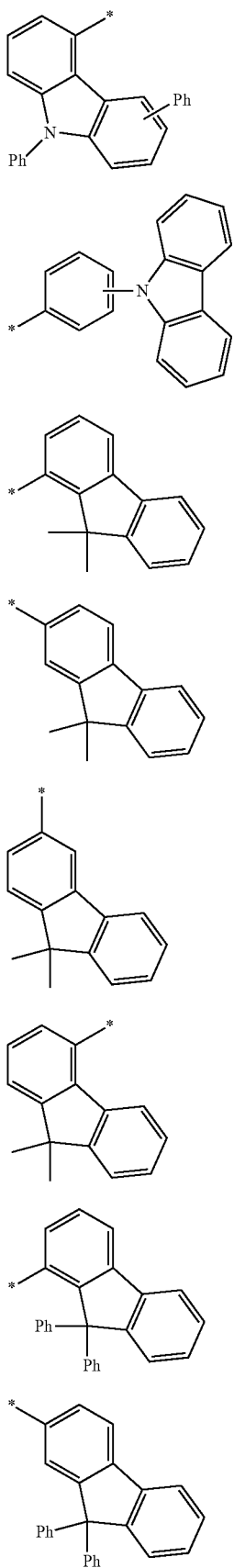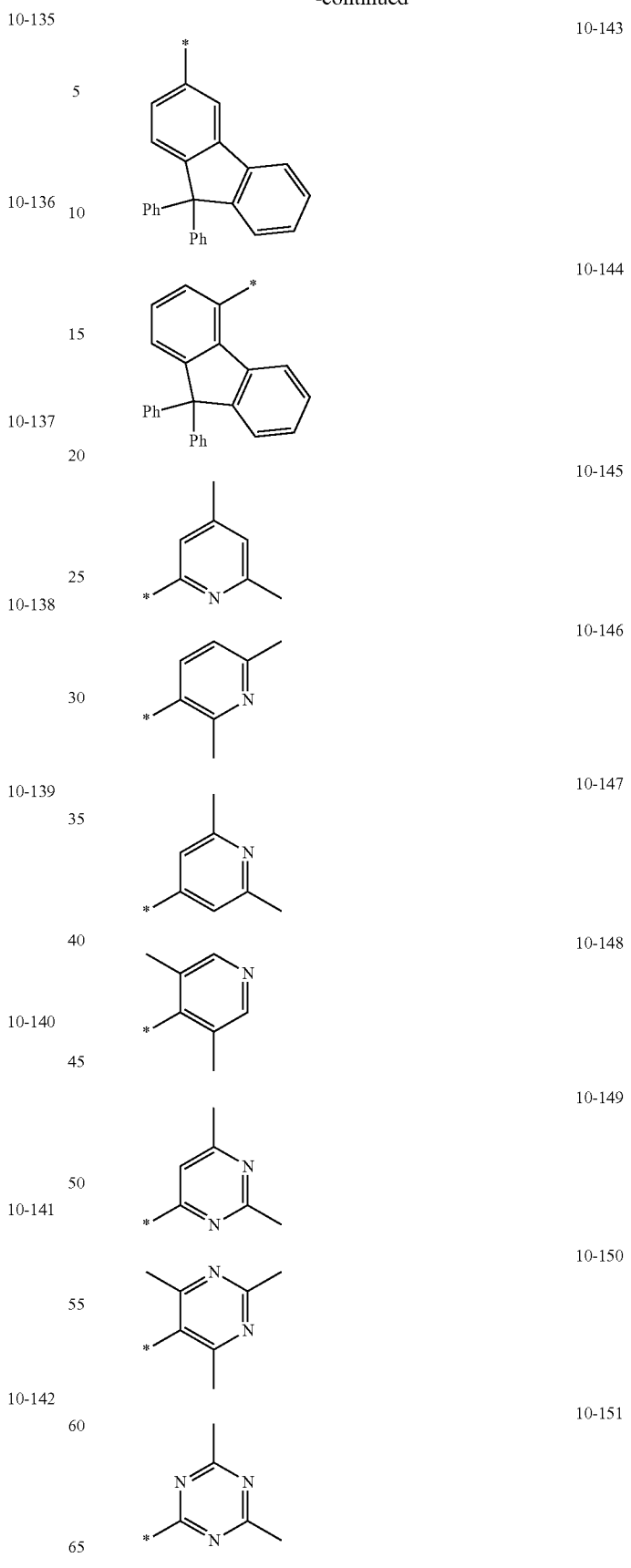

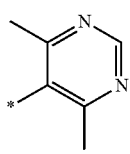
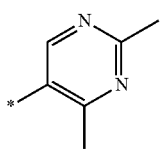
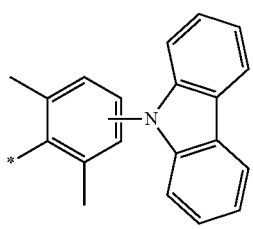
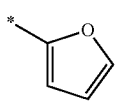
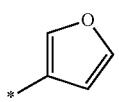
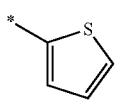
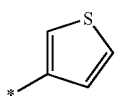
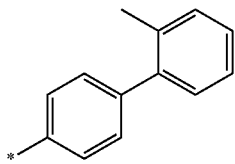
10-159
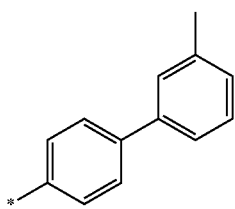
10-160
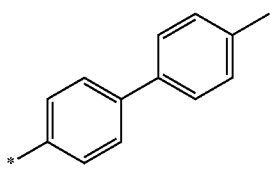
10-161
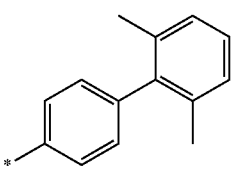
10-162
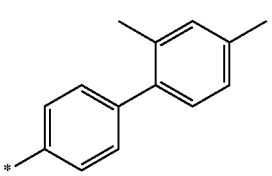
10-163
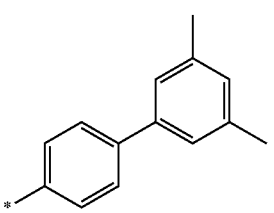
10-164
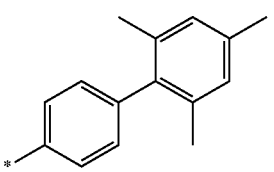
10-165
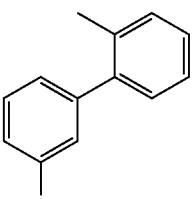
10-166
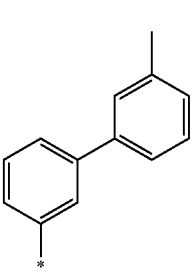
10-167
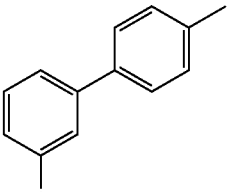
10-168
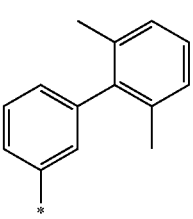
10-169

-continued
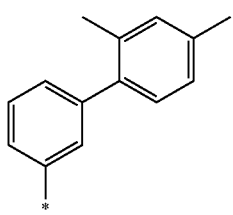
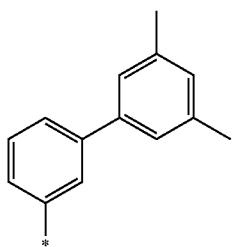
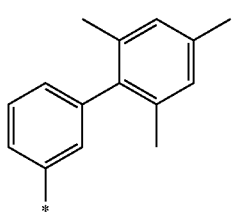
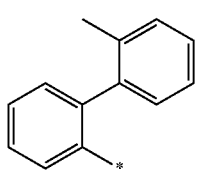
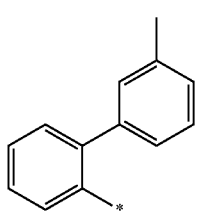
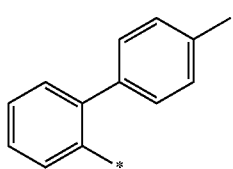
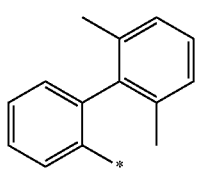
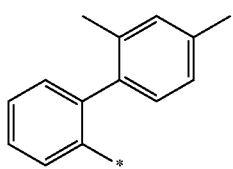
-continued
10-170
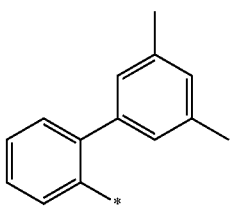
10-171
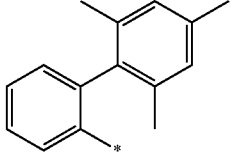
10-172
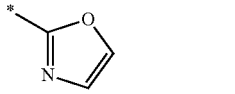
10-173
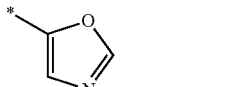
10-174
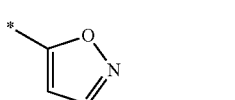
10-175
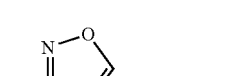
10-176
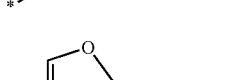
10-177
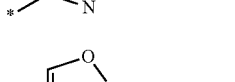
10-178
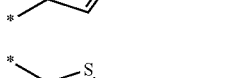
10-179
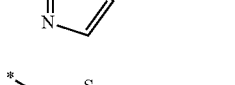
10-180
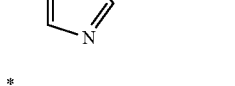
10-181
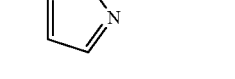
10-182
10-183
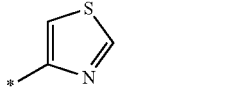
10-184
10-185
10-186
10-187
10-188
10-189
10-190

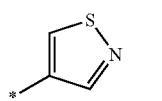
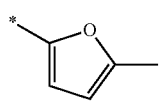
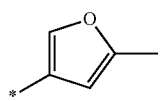
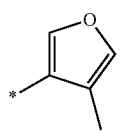
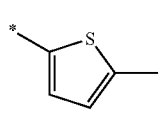
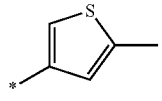
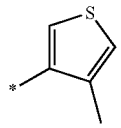
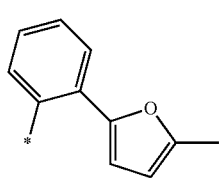
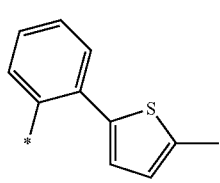
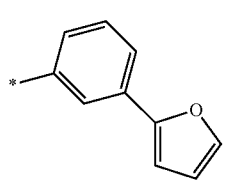
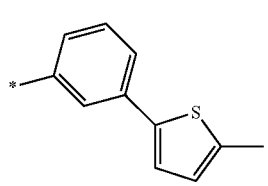
10-191
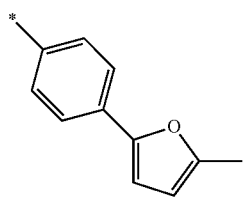
10-192
10-193
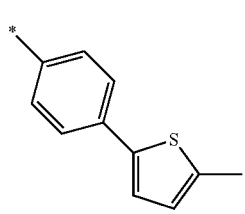
10-194
10-195
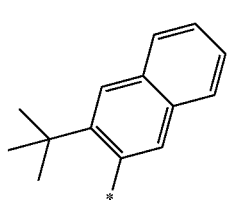
10-196
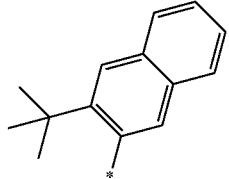
10-197
10-198
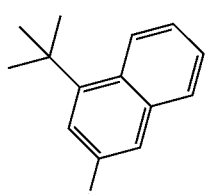
10-199
10-200
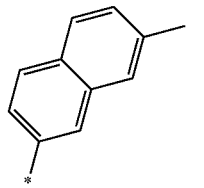
10-201
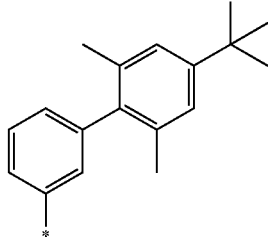
10-202
10-203
10-204
10-205
10-206
10-207
10-208

-continued
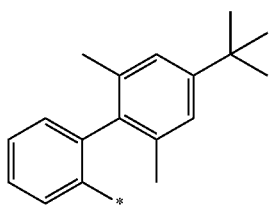
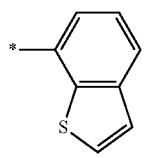
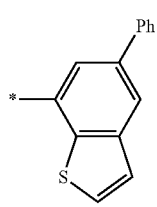
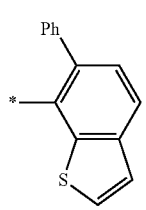
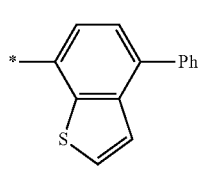
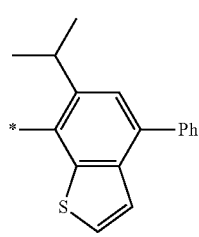
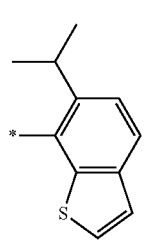
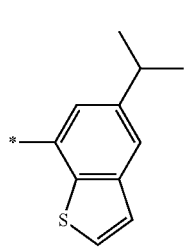
-continued
10-209
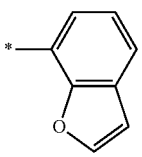
10-210
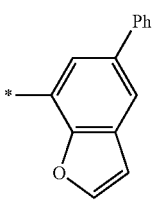
10-211
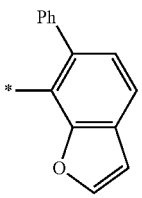
10-212
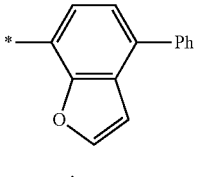
10-213
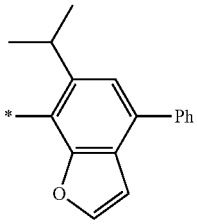
10-214
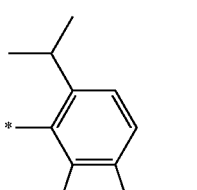
10-215
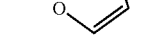
10-216
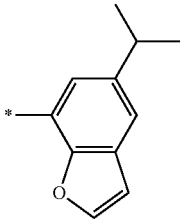
10-217
10-218
10-219
10-220
10-221
10-222
10-223
10-224

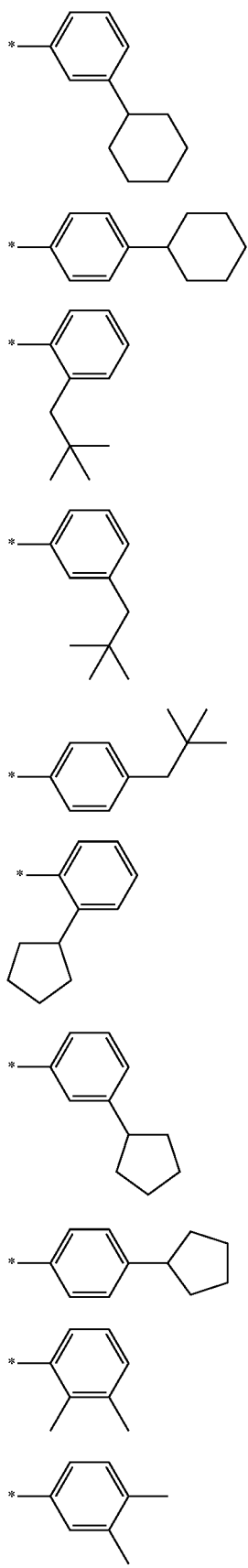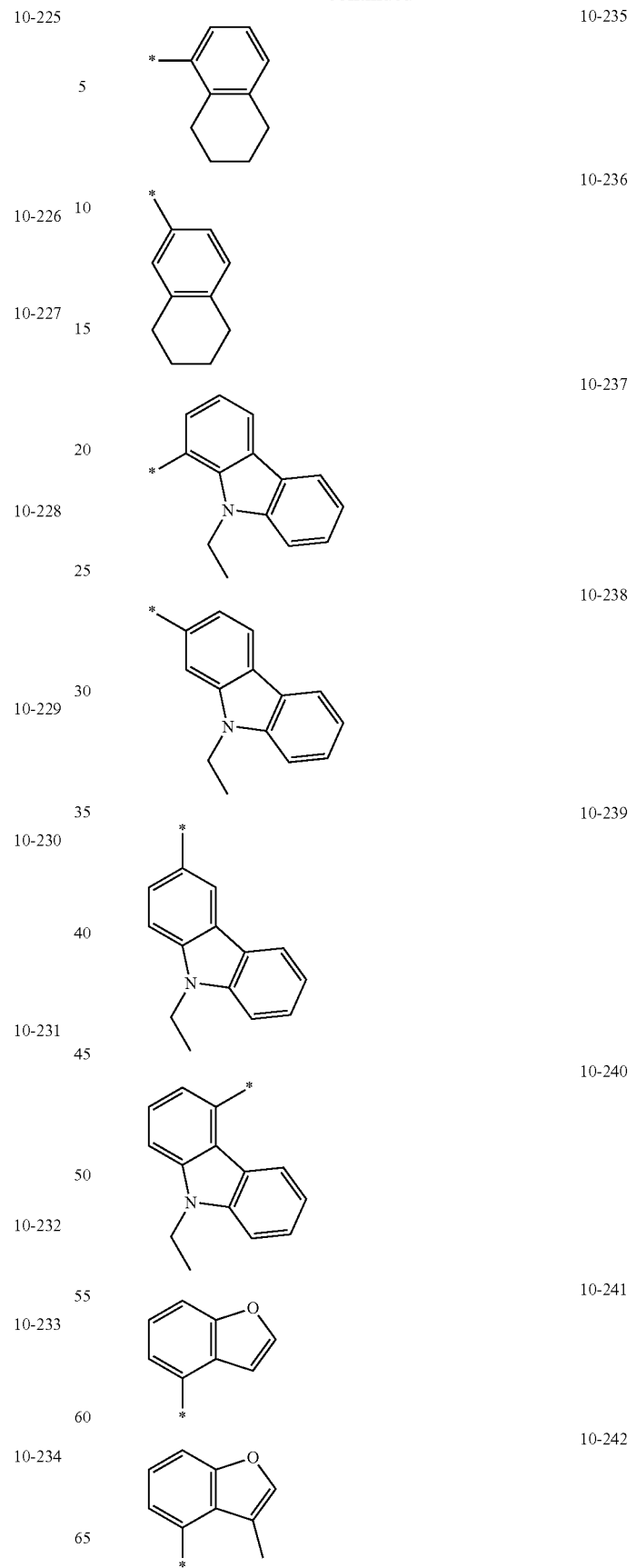

-continued
10-243 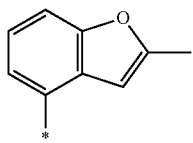
10-244 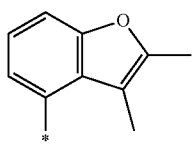
10-245 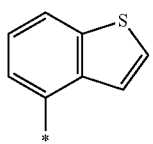
10-246 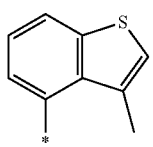
10-247 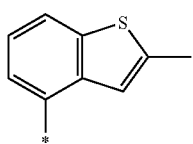
10-248 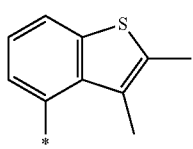
10-249 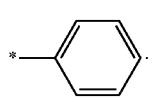
In Formulae 9-1 to 9-66 and 10-1 to 10-249, * indicates a binding site to a neighboring atom, Ph indicates a phenyl group, and TMS indicates a trimethylsilyl group.
The "group represented by one of Formulae 9-1 to 9-66 in which at least one hydrogen is substituted with deuterium" may be, for example, a group represented by one of Formulae 9-501 to 9-552:
9-501 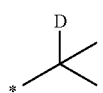
9-502 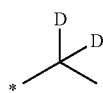
9-503 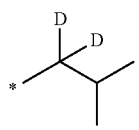
9-504 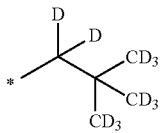
9-505 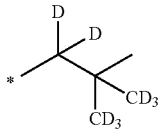
9-506 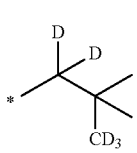
9-507 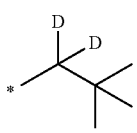
9-508 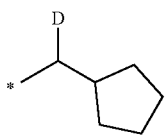
9-509 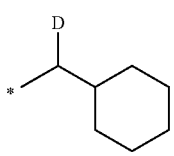
9-510 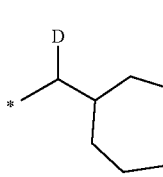
9-511 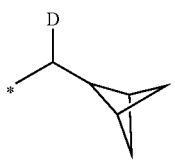
9-512 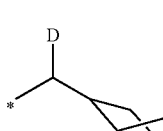
9-513 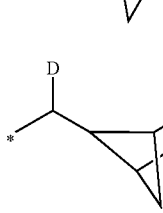

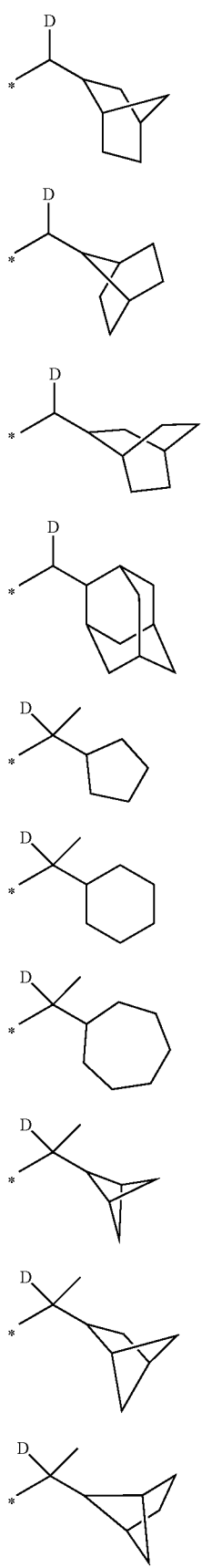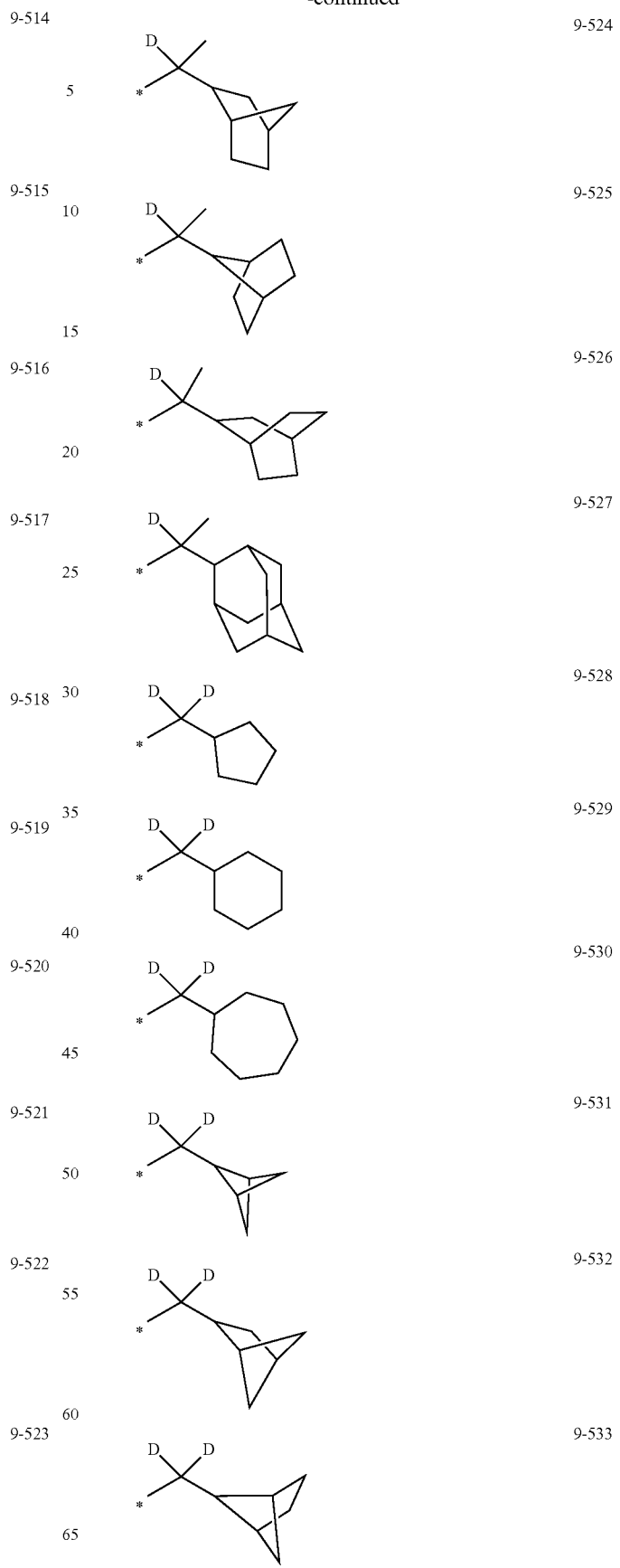

9-534 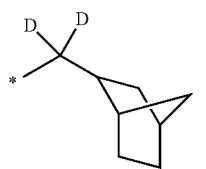
9-535 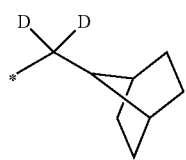
9-536 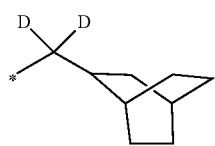
9-537 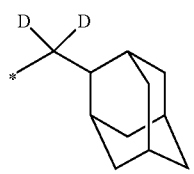
9-538 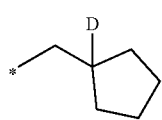
9-539 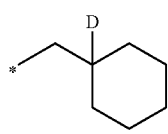
9-540 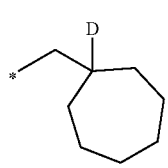
9-541 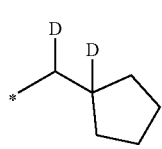
9-542 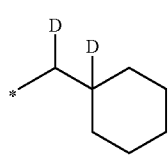
9-543 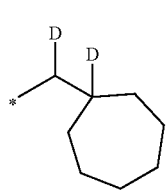
9-544 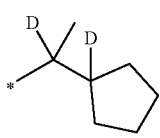
9-545 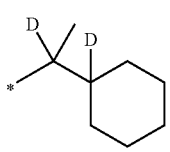
9-546 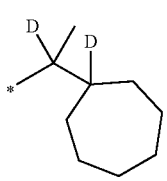
9-547 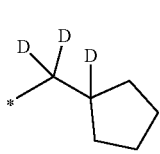
9-548 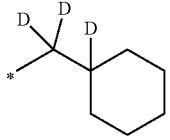
9-549 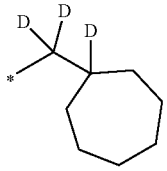
9-550 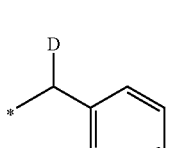
9-551 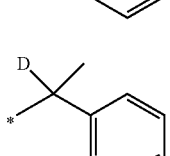
9-552 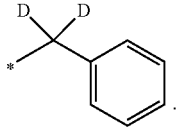
The "group represented by one of Formulae 10-1 to 10-249 in which at least one hydrogen is substituted with deuterium" may be, for example, a group represented by one of Formulae 10-501 to 10-510:

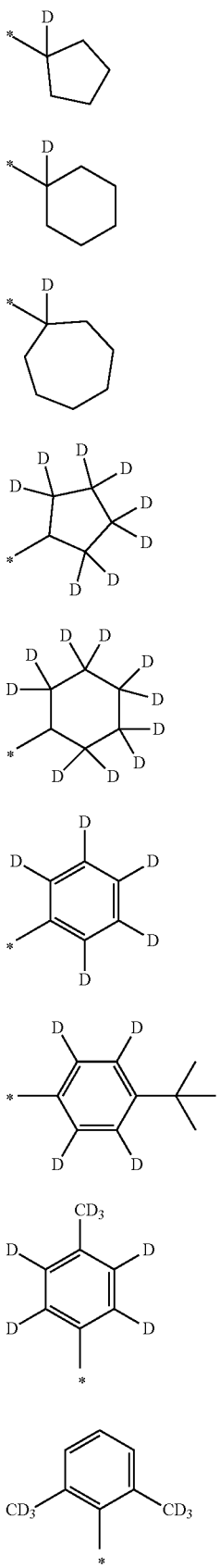

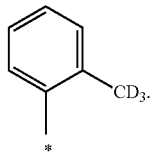

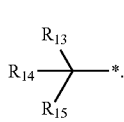

In one or more embodiments, at least one of $R_1$ to $R_{10}$ (for example, at least one of $R_1$ to $R_6$) in Formula 1 may be a group represented by Formula 2:

$$R_{14}\underset{R_{15}}{\overset{R_{13}}{-}}* \qquad \text{Formula 2}$$

The number of carbon atoms included in Formula 2 may be 4 or more (for example, 4 to 20, 4 to 15 or 4 to 10).

$R_{13}$ in Formula 2 may be hydrogen, deuterium, a $C_1$-$C_{20}$ alkyl group, deuterium-containing $C_1$-$C_{20}$ alkyl group, a $C_3$-$C_{10}$ cycloalkyl group, or a deuterium-containing $C_3$-$C_{10}$ cycloalkyl group.

$R_{14}$ and $R_{15}$ in Formula 2 may each independently be a $C_1$-$C_{20}$ alkyl group, deuterium-containing $C_1$-$C_{20}$ alkyl group, a $C_3$-$C_{10}$ cycloalkyl group, or a deuterium-containing $C_3$-$C_{10}$ cycloalkyl group.

* in Formula 2 indicates a binding site to a neighboring atom.

The terms "a deuterium-containing $C_1$-$C_{20}$ alkyl group" and "a deuterium-containing $C_3$-$C_{10}$ cycloalkyl group" as used herein each refer to a $C_1$-$C_{20}$ alkyl group substituted with at least one deuterium and a $C_3$-$C_{10}$ cycloalkyl group substituted with at least one deuterium, respectively. For example, a deuterium-containing methyl group may be —$CDH_2$, —$CD_2H$, and —$CD_3$.

Non-limiting examples of the "$C_1$-$C_{20}$ alkyl group" include a methyl group, an ethyl group, an n-propyl group, an isopropyl group, an n-butyl group, a sec-butyl group, an isobutyl group, a tert-butyl group, an n-pentyl group, a tert-pentyl group, a neopentyl group, an isopentyl group, a sec-pentyl group, a 3-pentyl group, a sec-isopentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an isononyl group, a sec-nonyl group, a tert-nonyl group, an n-decyl group, an isodecyl group, a sec-decyl group, a tert-decyl group, and the like, but embodiments of the present disclosure are not limited thereto.

Non-limiting of the "$C_3$-$C_{10}$ cycloalkyl group" include a cyclopentyl group, a cyclohexyl group, a cycloheptyl group, a cyclooctyl group, an adamantanyl group, a norbornanyl group, a bicyclo[1.1.1]pentyl group, a bicyclo[2.1.1]hexyl group, a bicyclo[2.2.1]heptyl group, a bicyclo[2.2.2]octyl group, and the like, but embodiments of the present disclosure are not limited thereto.

For example, $R_{13}$ in Formula 2 may be hydrogen or deuterium.

in an embodiment, $R_{13}$ in Formula 2 may be a $C_1$-$C_{20}$ alkyl group, a deuterium-containing $C_1$-$C_{20}$ alkyl group, a $C_3$-$C_{10}$ cycloalkyl group, or a deuterium-containing $C_3$-$C_{10}$ cycloalkyl group.

In an embodiment, $R_{14}$ and $R_{15}$ in Formula 2 may be different from each other.

In one or more embodiments, in Formula 2, $R_{13}$ may be hydrogen, deuterium, —$CH_3$, —$CDH_2$, —$CD_2H$, or —$CD_3$, and $R_{14}$ and $R_{15}$ may each independently be:

a methyl group, an ethyl group, an n-propyl group, an isopropyl group, an n-butyl group, a sec-butyl group, an isobutyl group, a tert-butyl group, an n-pentyl group, a tert-pentyl group, a neopentyl group, an isopentyl group, a sec-pentyl group, a 3-pentyl group, a sec-isopentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an isononyl group, a sec-nonyl group, a tert-nonyl group, an n-decyl group, an isodecyl group, a sec-decyl group, a tert-decyl group, a cyclopentyl group, a cyclohexyl group, a cycloheptyl group, a cyclooctyl group, a bicyclo[1.1.1]pentyl group, a bicyclo[2.1.1]hexyl group, a bicyclo[2.2.1]heptyl group, or a bicyclo[2.2.2]octyl group; or a methyl group, an ethyl group, an n-propyl group, an isopropyl group, an n-butyl group, a sec-butyl group, an isobutyl group, a tert-butyl group, an n-pentyl group, a tert-pentyl group, a neopentyl group, an isopentyl group, a sec-pentyl group, a 3-pentyl group, a sec-isopentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an isononyl group, a sec-nonyl group, a tert-nonyl group, an n-decyl group, an isodecyl group, a sec-decyl group, a tert-decyl group, a cyclopentyl group, a cyclohexyl group, a cycloheptyl group, a cyclooctyl group, a bicyclo[1.1.1]pentyl group, a bicyclo[2.1.1]hexyl group, a bicyclo[2.2.1]heptyl group, or a bicyclo[2.2.2]octyl group, each substituted with at least one deuterium, but embodiments of the present disclosure are not limited thereto.

In one or more embodiments, in Formula 2, $R_{13}$ may be hydrogen, deuterium, —$CH_3$, —$CDH_2$, —$CD_2H$, or —$CD_3$, $R_{14}$ may be —$CH_3$, —$CDH_2$, —$CD_2H$, or —$CD_3$, and $R_{15}$ may be:

an ethyl group, an n-propyl group, an isopropyl group, an n-butyl group, a sec-butyl group, an isobutyl group, a tert-butyl group, an n-pentyl group, a tert-pentyl group, a neopentyl group, an isopentyl group, a sec-pentyl group, a 3-pentyl group, a sec-isopentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an isononyl group, a sec-nonyl group, a tert-nonyl group, an n-decyl group, an isodecyl group, a sec-decyl group, a tert-decyl group, a cyclopentyl group, a cyclohexyl group, a cycloheptyl group, a cyclooctyl group, a bicyclo[1.1.1]pentyl group, a bicyclo[2.1.1]hexyl group, a bicyclo[2.2.1]heptyl group, or a bicyclo[2.2.2]octyl group; or an ethyl group, an n-propyl group, an isopropyl group, an n-butyl group, a sec-butyl group, an isobutyl group, a tert-butyl group, an n-pentyl group, a tert-pentyl group, a neopentyl group, an isopentyl group, a sec-pentyl group, a 3-pentyl group, a sec-isopentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an isononyl group, a sec-nonyl group, a tert-nonyl group, an n-decyl group, an isodecyl group, a sec-decyl group, a tert-decyl group, a cyclopentyl group, a cyclohexyl group, a cycloheptyl group, a cyclooctyl group, a bicyclo[1.1.1]pentyl group, a bicyclo[2.1.1]hexyl group, a bicyclo[2.2.1]heptyl group, or a bicyclo[2.2.2]octyl group, each substituted with at least one deuterium, but embodiments of the present disclosure are not limited thereto.

In one or more embodiments, $R_{14}$ and $R_{15}$ in Formula 2 may each independently be —$CH_3$, —$CDH_2$, —$CD_2H$, —$CD_3$, a group represented by one of Formulae 9-1 to 9-33, a group represented by one of Formulae 9-1 to 9-33 in which at least one hydrogen is substituted with deuterium, a group represented by one of Formulae 10-1 to 10-10, or a group represented by one of Formulae 10-1 to 10-10 in which at least one hydrogen is substituted with deuterium, but embodiments of the present disclosure are not limited thereto.

In one or more embodiments, a case where $R_{13}$ to $R_{15}$ in Formula 2 are all the same may be excluded.

In one or more embodiments, a case where $R_{13}$ to $R_{15}$ in Formula 2 are all methyl groups may be excluded.

In an embodiment, at least one of $R_1$ to $R_6$ in Formula 1 may each independently be a group represented by Formula 2.

For example, $R_4$ in Formula 1 may be a group represented by Formula 2.

In an embodiment, $R_1$ to $R_3$, $R_5$, and $R_6$ in Formula 1 may each be hydrogen, and $R_4$ may be a group represented by Formula 2.

In an embodiment, at least one of $R_4$, $R_7$, and $R_9$ in Formula 1 may not be each hydrogen.

In one or more embodiments, each of $R_7$ and $R_9$ in Formula 1 may not be hydrogen.

In one or more embodiments, in Formula 1, each of $R_7$ and $R_9$ may not be hydrogen, and each of $R_8$ and $R_{10}$ may not be hydrogen.

In one or more embodiments, none of $R_4$, $R_7$, and $R_9$ in Formula 1 may be hydrogen.

In one or more embodiments, each of $R_7$ and $R_9$ in Formula 1 may not be hydrogen, and $R_7$ and $R_9$ may be identical to each other.

In one or more embodiments, each of $R_7$ and $R_9$ in Formula 1 may not be hydrogen, and $R_7$ and $R_9$ may be different from each other.

In one or more embodiments, in Formula 1, each of $R_7$ and $R_9$ may not be hydrogen, $R_7$ and $R_9$ may be different from each other, and the number of carbon atoms included in $R_7$ may be greater than that of carbon atoms included in $R_9$.

In one or more embodiments, $R_7$ and $R_9$ in Formula 1 may each independently be a substituted or unsubstituted $C_1$-$C_{60}$ alkyl group, a substituted or unsubstituted $C_3$-$C_{10}$ cycloalkyl group, or a substituted or unsubstituted $C_6$-$C_{60}$ aryl group.

In one or more embodiments, at least one of $R_7$ and $R_9$ in Formula 1 may each independently be a substituted or unsubstituted $C_2$-$C_{60}$ alkyl group, a substituted or unsubstituted $C_3$-$C_{10}$ cycloalkyl group, or a substituted or unsubstituted $C_6$-$C_{60}$ aryl group.

In one or more embodiments, at least one of $A_1$ to $A_6$ in Formula 1 may each independently be a substituted or unsubstituted $C_2$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted heterocycloalkyl group, a substituted or unsubstituted $C_3$-$C_{10}$ cycloalkenyl group, a substituted or unsubstituted heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_7$-$C_{60}$ arylalkyl group, a substituted or unsubstituted $C_1$-$C_{60}$ heteroaryl group, a substituted or unsubstituted $C_1$-$C_{60}$ heteroaryloxy group, a substituted or unsubstituted $C_1$-$C_{60}$ heteroarylthio group, a substituted or unsubstituted $C_2$-$C_{60}$ heteroarylalkyl group, a substituted or unsubstituted monovalent non-aromatic condensed polycyclic group, or a substituted or unsubstituted monovalent non-aromatic condensed heteropolycyclic group.

For example, at least one of $A_1$ to $A_6$ in Formula 1 may each independently be:

an ethyl group, an n-propyl group, an isopropyl group, an n-butyl group, a sec-butyl group, an isobutyl group, a tert-butyl group, an n-pentyl group, a tert-pentyl group, a neopentyl group, an isopentyl group, a sec-pentyl group, a 3-pentyl group, a sec-isopentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an isononyl group, a sec-nonyl group, a tert-nonyl group, an n-decyl group, an isodecyl group, a sec-decyl group, a tert-decyl group, a methoxy group, an ethoxy group, a propoxy group, a butoxy group, a pentoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a bicyclo[1.1.1]pentyl group, a bicyclo[2.1.1]hexyl group, a bicyclo[2.2.1]heptyl group, a bicyclo[2.2.2]octyl group, a phenyl group, a biphenyl group, a terphenyl group, a naphthyl group, a pyridinyl group, a pyrimidinyl group, a carbazolyl group, a fluorenyl group, a dibenzosilolyl group, a dibenzofuranyl group, or a dibenzothiophenyl group;

an ethyl group, an n-propyl group, an isopropyl group, an n-butyl group, a sec-butyl group, an isobutyl group, a tert-butyl group, an n-pentyl group, a tert-pentyl group, a neopentyl group, an isopentyl group, a sec-pentyl group, a 3-pentyl group, a sec-isopentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an isononyl group, a sec-nonyl group, a tert-nonyl group, an n-decyl group, an isodecyl group, a sec-decyl group, or a tert-decyl group, each substituted with deuterium, —F, a cyano group, any combination thereof; or a methoxy group, an ethoxy group, a propoxy group, a butoxy group, a pentoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a bicyclo[1.1.1]pentyl group, a bicyclo[2.1.1]hexyl group, a bicyclo[2.2.1]heptyl group, a bicyclo[2.2.2]octyl group, a phenyl group, a biphenyl group, a terphenyl group, a naphthyl group, a pyridinyl group, a pyrimidinyl group, a carbazolyl group, a fluorenyl group, a dibenzosilolyl group, a dibenzofuranyl group, or a dibenzothiophenyl group, each substituted with deuterium, —F, a cyano group, a $C_1$-$C_{10}$ alkyl group, any combination thereof.

$Q_3$ to $Q_5$ are the same as described herein.

In an embodiment, at least one of $A_1$ to $A_6$ in Formula 1 may each independently be a group represented by one of Formulae 9-1 to 9-66, a group represented by one of Formulae 9-1 to 9-66 in which at least one hydrogen is substituted with deuterium, a group represented by one of Formulae 10-1 to 10-249, or a group represented by one of Formulae 10-1 to 10-249 in which at least one hydrogen is substituted with deuterium, but embodiments of the present disclosure are not limited thereto.

In one or more embodiments, $A_7$ may not be hydrogen.

In one or more embodiments, in Formula 1, a group represented by *—C($A_1$)($A_2$)($A_3$) and a group represented by *—C($A_4$)($A_5$)($A_6$) may be identical to each other, and * indicates a binding site to a neighboring atom.

In one or more embodiments, in Formula 1 a group represented by *—C($A_1$)($A_2$)($A_3$) and a group represented by *—C($A_4$)($A_5$)($A_6$) may be different from each other, and * indicates a binding site to a neighboring atom.

In one or more embodiments, in Formula 1, $A_1$ an $A_2$ may be identical to each other, and $A_1$ and $A_3$ may be different from each other; and/or $A_4$ and $A_5$ may be identical to each other, and $A_4$ and $A_6$ may be different from each other.

In Formula 1, two or more of $R_1$ to $R_{10}$ may optionally be linked to form a $C_5$-$C_{60}$ carbocyclic group unsubstituted or substituted with at least one $R_{1a}$ or a $C_1$-$C_{60}$ heterocyclic group unsubstituted or substituted with at least one $R_{1a}$, and two or more of $A_1$ to $A_6$ may optionally be linked to form a $C_5$-$C_{60}$ carbocyclic group unsubstituted or substituted with at least one $R_{1a}$ or a $C_1$-$C_{60}$ heterocyclic group unsubstituted or substituted with at least one $R_{1a}$. Here, $R_{1a}$ is the same as defined in connection with $R_7$.

For example, a $C_5$-$C_{60}$ carbocyclic group unsubstituted or substituted with at least one $R_{1a}$ and a $C_1$-$C_{60}$ heterocyclic group unsubstituted or substituted with at least one $R_{1a}$ may each independently be a cyclopentane group, a cyclohexane group, a cycloheptane group, a cyclooctane group, an adamantane group, a norbornane group, a norbornene group, a cyclopentene group, a cyclohexene group, a cycloheptene group, a bicyclo[1.1.1]pentane group, a bicyclo[2.1.1]hexane group, a bicyclo[2.2.1]heptane group, a bicyclo[2.2.2]octane group, a benzene group, a naphthalene group, a fluorene group, a phenanthrene group, an anthracene group, a fluoranthene group, a triphenylene group, a pyrene group, a chrysene group, a pyrrole group, a thiophene group, a furan group, an imidazole group, a pyrazole group, a thiazole group, an isothiazole group, an oxazole group, an isoxazole group, a pyridine group, a pyrazine group, a pyrimidine group, a pyridazine group, an isoindole group, an indole group, an indazole group, a purine group, a quinoline group, an isoquinoline group, a benzoquinoline group, a quinoxaline group, a quinazoline group, a cinnoline group, a carbazole group, a phenanthroline group, a benzimidazole group, a benzofuran group, a benzothiophene group, an isobenzothiophene group, a benzoxazole group, an isobenzoxazole group, a triazole group, a tetrazole group, an oxadiazole group, a triazine group, a tetrazine group, a dibenzofuran group, a dibenzothiophene group, a benzocarbazole group, a dibenzocarbazole group, an imidazopyridine group, or an imidazopyrimidine group, each unsubstituted or substituted with at least one $R_{1a}$, but embodiments of the present disclosure are not limited thereto.

In an embodiment, two or more of $A_1$ to $A_3$ (for example, all of $A_1$ to $A_3$) in Formula 1 may be linked to form a $C_5$-$C_{60}$ carbocyclic group unsubstituted or substituted with at least one $R_{1a}$ or a $C_1$-$C_{60}$ heterocyclic group unsubstituted or substituted with at least one $R_{1a}$, and/or two or more of $A_4$ to $A_6$ (for example, all of $A_4$ to $A_6$) in Formula 1 may be linked to form a $C_5$-$C_{60}$ carbocyclic group unsubstituted or substituted with at least one $R_{1a}$ or a $C_1$-$C_{60}$ heterocyclic group unsubstituted or substituted with at least one $R_{1a}$.

In one or more embodiments, in Formula 1, at least one of a group represented by *—C($A_1$)($A_2$)($A_3$) and a group represented by *-($A_4$)($A_5$)($A_6$) may each independently be a cyclopentane group, a cyclohexane group, a cycloheptane group, a cyclooctane group, an adamantane group, a norbornane group, a norbornene group, a cyclopentene group, a cyclohexene group, a cycloheptene group, a bicyclo[1.1.1]pentane group, a bicyclo[2.1.1]hexane group, a bicyclo[2.2.1]heptane group, a bicyclo[2.2.2]octane group, a benzene group, a naphthalene group, a fluorene group, a phenanthrene group, an anthracene group, a fluoranthene group, a triphenylene group, a pyrene group, a chrysene group, a pyrrole group, a thiophene group, a furan group, an imidazole group, a pyrazole group, a thiazole group, an isothiazole group, an oxazole group, an isoxazole group, a pyridine group, a pyrazine group, a pyrimidine group, a pyridazine group, an isoindole group, an indole group, an indazole group, a purine group, a quinoline group, an isoquinoline group, a benzoquinoline group, a quinoxaline group, a quinazoline group, a cinnoline group, a carbazole group, a phenanthroline group, a benzimidazole group, a benzofuran group, a benzothiophene group, an isobenzothiophene group, a benzoxazole group, an isobenzoxazole group, a triazole group, a tetrazole group, an oxadiazole group, a triazine group, a tetrazine group, a dibenzofuran group, a dibenzothiophene group, a benzocarbazole group, a dibenzocarbazole group, an imidazopyridine group, or an imidazopyrimidine group, each unsubstituted or substituted with at least one $R_{1a}$, but embodiments of the present disclosure are not limited thereto.

For example, the organometallic compound represented by Formula 1 may be one of Compounds 1 to 6, but embodiments of the present disclosure are not limited thereto:

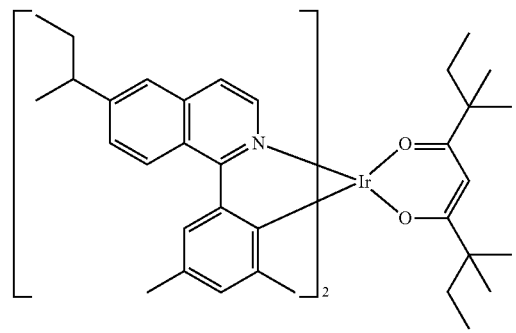

2

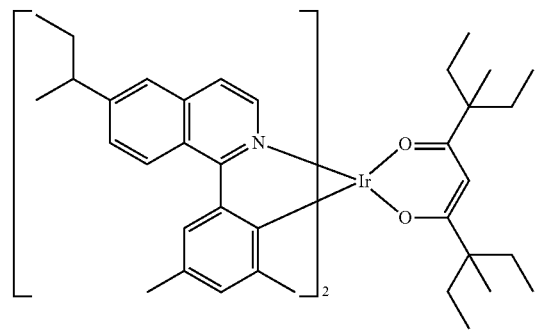

3

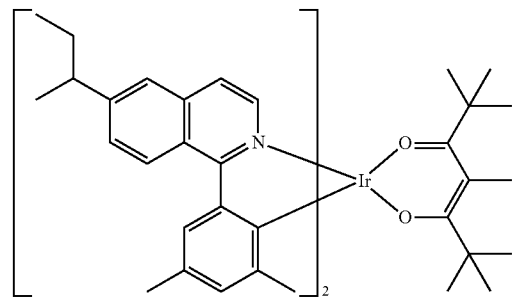

4

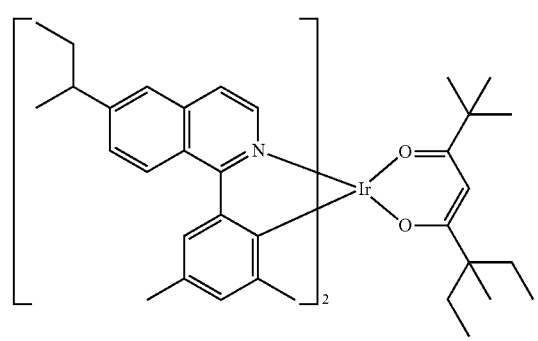

1

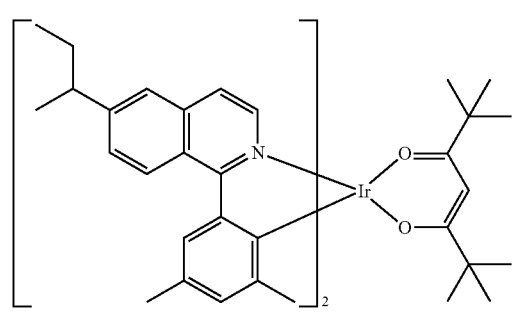

5

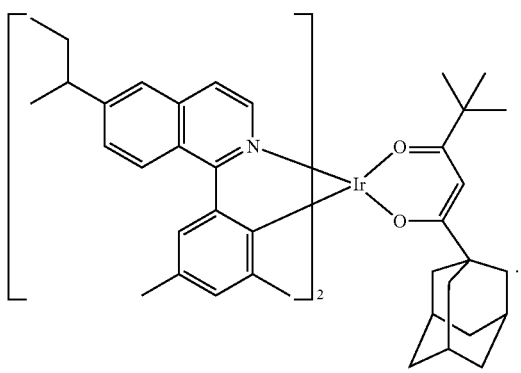

At least one of $R_1$ to $R_{10}$ in Formula 1 may each independently be a substituted or unsubstituted $C_2$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_7$-$C_{60}$ arylalkyl group, a substituted or unsubstituted $C_1$-$C_{60}$ heteroaryl group, a substituted or unsubstituted $C_1$-$C_{60}$ heteroaryloxy group, a substituted or unsubstituted $C_1$-$C_{60}$ heteroarylthio group, a substituted or unsubstituted $C_2$-$C_{60}$ heteroarylalkyl group, a substituted or unsubstituted monovalent non-aromatic condensed polycyclic group, a substituted or unsubstituted monovalent non-aromatic condensed heteropolycyclic group, —N($Q_1$)($Q_2$), —Si($Q_3$)($Q_4$)($Q_5$), —Ge($Q_3$)($Q_4$)($Q_5$), —B($Q_6$)($Q_7$), —P(=O)($Q_8$)($Q_9$), or —P($Q_8$)($Q_9$). For example, at least one of $R_1$ to $R_{10}$ (for example, at least one of $R_1$ to $R_6$) in Formula 1 may not be hydrogen nor a methyl group, but may be a substituent described above. In this regard, the organometallic compound represented by Formula 1 may have an increased electron-donating effect so that a wavelength of the light emitted by the organometallic compound may be shifted to a relatively short wavelength side. Accordingly, the non-radiative transition of the organometallic compound may decrease while the photoluminescence quantum yield (PLQY) of the organometallic compound may increase. As a result, an electronic device, for example, an organic light-emitting device, including the organometallic compound may have increased external quantum efficiency (EQE), and the full width at half maximum (FWHM) of the electroluminescence (EL) spectrum peak of such an organic light-emitting device may be reduced.

In one or more embodiments, $A_1$ to $A_6$ in Formula 1 may each independently be a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted heterocycloalkyl group, a substituted or unsubstituted $C_3$-$C_{10}$ cycloalkenyl group, a substituted or unsubstituted heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_7$-$C_{60}$ arylalkyl group, a substituted or unsubstituted $C_1$-$C_{60}$ heteroaryl group, a substituted or unsubstituted $C_1$-$C_{60}$ heteroaryloxy group, a substituted or unsubstituted $C_1$-$C_{60}$ heteroarylthio group, a substituted or unsubstituted $C_2$-$C_{60}$ heteroarylalkyl group, a substituted or unsubstituted monovalent non-aromatic condensed polycyclic group, or a substituted or unsubstituted monovalent non-aromatic condensed heteropolycyclic group. For example, each of $A_1$ to $A_6$ Formula 1 may not be hydrogen, but may include at least one carbon.

Although not limited to a particular theory, an α-proton has chemical reactivity that is about $10^5$ greater than that of a β-proton. That is, the α-proton may cause a side reaction due to production of intermediates in various forms during synthesis and/or storage of a compound. However, each $A_1$ to $A_6$ in Formula 1 as described above may not include the α-proton, and in this regard, the organometallic compound represented by Formula 1 may have a stable chemical structure with minimal occurrence of a side reaction before/after synthesis, and at the same time, an intermolecular interaction of the organometallic compound may be minimized during the operation of an electronic device (for example, an organic light-emitting device) including the organometallic compound. Thus, an electronic device, for example, an organic light-emitting device, including the organometallic compound represented by Formula 1 may have improved luminescence efficiency and lifespan characteristics.

A highest occupied molecular orbital (HOMO) energy level, a lowest unoccupied molecular orbital (LUMO) energy level, a singlet ($S_1$) energy level, and a triplet ($T_1$) energy level of some compounds of the organometallic compound represented by Formula 1 are evaluated by a density functional theory (DFT) of Gaussian program with molecular structure optimization based on B3LYP, and results are shown in Table 1.

TABLE 1

| Compound No. | HOMO (eV) | LUMO (eV) | $T_1$ (eV) |
|---|---|---|---|
| 1 | −4.554 | −1.672 | 1.974 |
| 2 | −4.542 | −1.659 | 2.008 |
| 3 | −4.543 | −1.660 | 1.975 |
| 4 | −4.504 | −1.644 | 1.978 |
| 5 | −4.543 | −1.658 | 1.977 |
| 6 | −4.567 | −1.672 | 1.990 |

Referring to Table 1, it is confirmed that the organometallic compound represented by Formula 1 has such electrical characteristics that are suitable for use as a dopant for in an electronic device, for example, for an organic light-emitting device.

Synthesis methods of the organometallic compound represented by Formula 1 may be recognizable by one of ordinary skill in the art by referring to Synthesis Examples provided below.

Therefore, the organometallic compound represented by Formula 1 may be suitable for use as a dopant in an organic layer of an organic light-emitting device, for example, in an emission layer of the organic layer. Another aspect of the present disclosure provides an organic light-emitting device including: a first electrode, a second electrode, and an organic layer disposed between the first electrode and the second electrode and including an emission layer, wherein the organic layer includes at least one organometallic compound represented by Formula 1.

The organic light-emitting device may have, due to the inclusion of an organic layer including the organometallic compound represented by Formula 1, an improved driving voltage, an improved external quantum efficiency, an improved low roll-off ratio, and an improved long lifespan.

The organometallic compound represented by Formula 1 may be used between a pair of electrodes of an organic light-emitting device. For example, the organometallic compound represented by Formula 1 may be included in the emission layer. In this regard, the organometallic compound may act as a dopant, and the emission layer may further include a host (that is, an amount of the organometallic compound represented by Formula 1 is smaller than an amount of the host). The emission layer may emit red light having a maximum emission wavelength in a range of, for example, about 550 nanometers (nm) or more (for example, about 550 nm or more and about 900 nm or less).

The expression "(an organic layer) includes at least one organometallic compound" as used herein may include an embodiment in which "(an organic layer) includes identical organometallic compounds represented by Formula 1" and an embodiment in which "(an organic layer) includes two or more different organometallic compounds represented by Formula 1".

For example, the organic layer may include, as the organometallic compound, only Compound 1. In this regard, Compound 1 may be included only in the emission layer of the organic light-emitting device. In one or more embodiments, the organic layer may include, as the organometallic compound, Compound 1 and Compound 2. In this regard, Compound 1 and Compound 2 may be included in an identical layer (for example, Compound 1 and Compound 2 all may exist in an emission layer).

The first electrode may be an anode, which is a hole injection electrode, and the second electrode may be a cathode, which is an electron injection electrode; or the first electrode may be a cathode, which is an electron injection electrode, and the second electrode may be an anode, which is a hole injection electrode.

For example, the organic light-emitting device, the first electrode is an anode, and the second electrode is a cathode, and the organic layer further includes a hole transport region between the first electrode and the emission layer and an electron transport region between the emission layer and the second electrode, and the hole transport region includes a hole injection layer, a hole transport layer, an electron blocking layer, or any combination thereof, and the electron transport region includes a hole blocking layer, an electron transport layer, an electron injection layer, or any combination thereof.

The term "organic layer" as used herein refers to a single layer and/or a plurality of layers disposed between the first electrode and the second electrode of an organic light-emitting device. The "organic layer" may include, in addition to an organic compound, an organometallic complex including metal.

The FIGURE is a schematic cross-sectional view of an organic light-emitting device 10 according to an embodiment. Hereinafter, the structure of an organic light-emitting device according to an embodiment and a method of manufacturing an organic light-emitting device according to an embodiment will be described in connection with the FIGURE. The organic light-emitting device 10 includes a first electrode 11, an organic layer 15, and a second electrode 19, which are sequentially stacked.

A substrate may be additionally disposed under the first electrode 11 or above the second electrode 19. For use as the substrate, any substrate that is used in general organic light-emitting devices may be used, and the substrate may be a glass substrate or a transparent plastic substrate, each having excellent mechanical strength, thermal stability, transparency, surface smoothness, ease of handling, and water resistance.

The first electrode 11 may be formed by depositing or sputtering a material for forming the first electrode 11 on the substrate. The first electrode 11 may be an anode. The material for forming the first electrode 11 may be a material with a high work function to facilitate hole injection. The first electrode 11 may be a reflective electrode, a semi-reflective electrode, or a transmissive electrode. The material for forming the first electrode may be, for example, indium tin oxide (ITO), indium zinc oxide (IZO), tin oxide ($SnO_2$), and zinc oxide (ZnO). In one or more embodiments, the material for forming the first electrode 11 may be metal, such as magnesium (Mg), aluminum (Al), aluminum-lithium (Al—Li), calcium (Ca), magnesium-indium (Mg—In), or magnesium-silver (Mg—Ag).

The first electrode 11 may have a single-layered structure or a multi-layered structure including two or more layers. For example, the first electrode 11 may have a three-layered structure of ITO/Ag/ITO, but the structure of the first electrode 11 is not limited thereto.

The organic layer 15 is disposed on the first electrode 11.

The organic layer 15 may include a hole transport region, an emission layer, and an electron transport region.

The hole transport region may be disposed between the first electrode 11 and the emission layer.

The hole transport region may include a hole injection layer, a hole transport layer, an electron blocking layer, a buffer layer, or any combination thereof.

The hole transport region may include only either a hole injection layer or a hole transport layer. In one or more embodiments, the hole transport region may have a hole injection layer/hole transport layer structure or a hole injection layer/hole transport layer/electron blocking layer structure, which are sequentially stacked in this stated order from the first electrode 11.

When the hole transport region includes a hole injection layer, the hole injection layer may be formed on the first electrode 11 by using one or more suitable methods, for example, vacuum deposition, spin coating, casting, and/or Langmuir-Blodgett (LB) deposition.

When a hole injection layer is formed by vacuum deposition, the deposition conditions may vary according to a material that is used to form the hole injection layer, and the structure and thermal characteristics of the hole injection layer. For example, the deposition conditions may include a deposition temperature of about 100° C. to about 500° C., a vacuum pressure of about $10^{-8}$ to about $10^{-3}$ torr, and a deposition rate of about 0 Angstroms per second (Å/sec) to about 100 Å/sec. However, the deposition conditions are not limited thereto, but embodiments of the present disclosure are not limited thereto.

When the hole injection layer is formed using spin coating, coating conditions may vary according to the material used to form the hole injection layer, and the structure and thermal properties of the hole injection layer. For example, a coating speed may be from about 2,000 revolutions per minute (rpm) to about 5,000 rpm, and a temperature at which a heat treatment is performed to remove a solvent after coating may be from about 80° C. to about 200° C. However, the coating conditions are not limited thereto.

Conditions for forming a hole transport layer and an electron blocking layer may be understood by referring to conditions for forming the hole injection layer.

The hole transport region may include m-MTDATA, TDATA, 2-TNATA, NPB, β-NPB, TPD, spiro-TPD, spiro-NPB, methylated-NPB, TAPC, HMTPD, 4,4',4"-tris(N-carbazolyl)triphenylamine (TCTA), polyaniline/dodecylbenzene sulfonic acid (PANI/DBSA), poly(3,4-ethylenedioxythiophene)/poly(4-styrene sulfonate) (PEDOT/PSS), polyaniline/camphor sulfonic acid (PANI/CSA), polyaniline/poly(4-styrene sulfonate) (PANI/PSS), a compound represented by Formula 201 below, a compound represented by Formula 202 below, or any combination thereof:

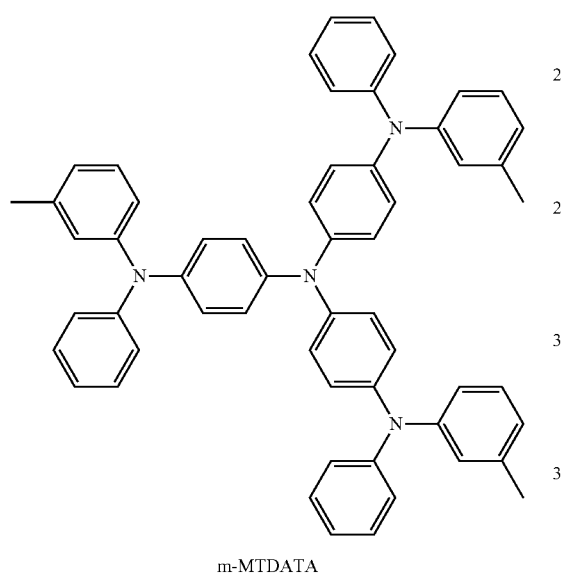

m-MTDATA

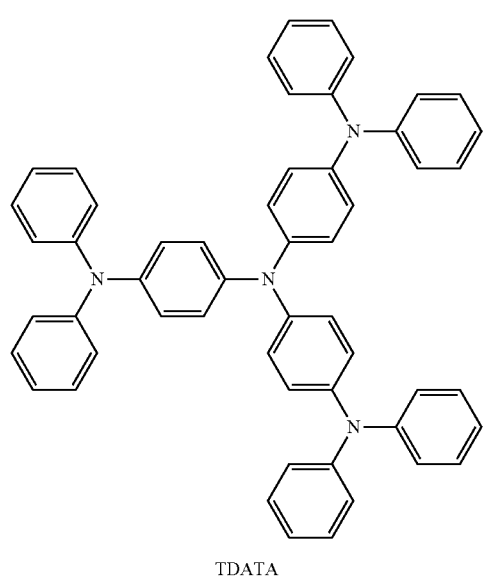

TDATA

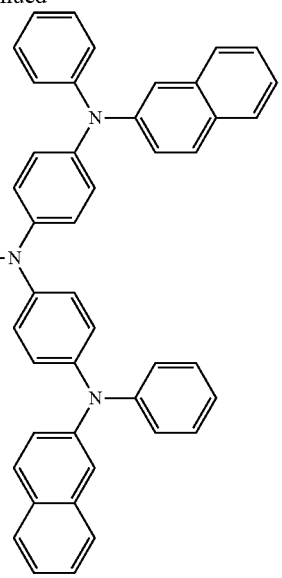

2-TNATA

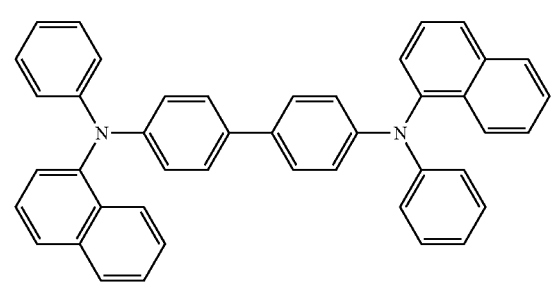

NPB

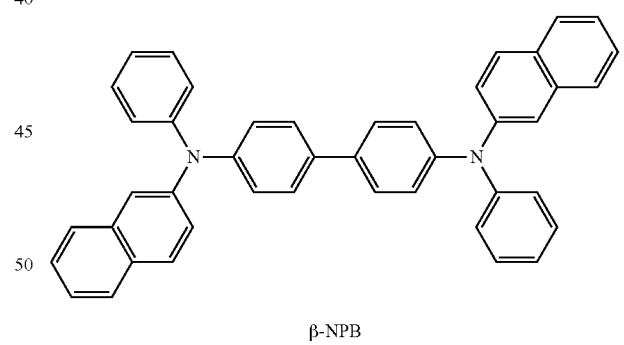

β-NPB

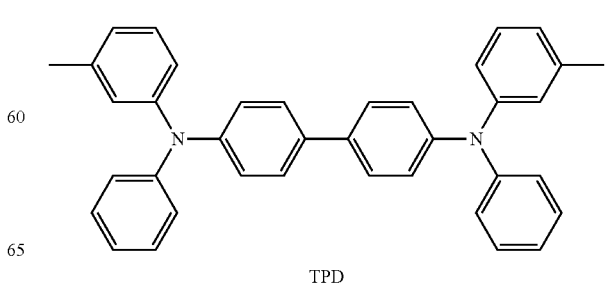

TPD

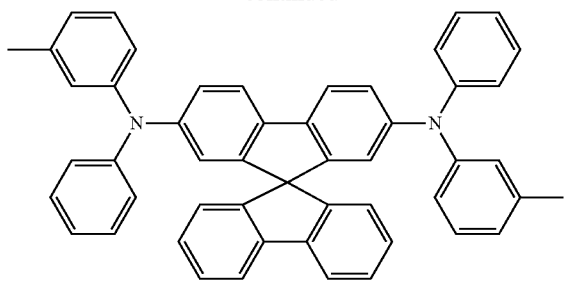

Spiro-TPD

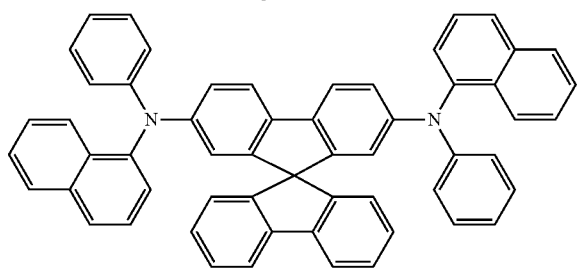

Spiro-NPB

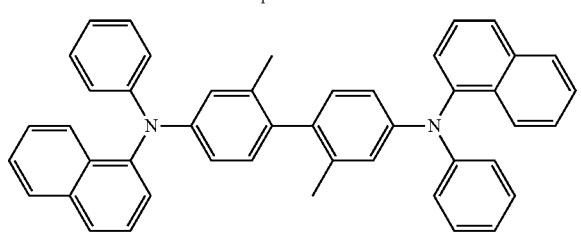

methylated NPB

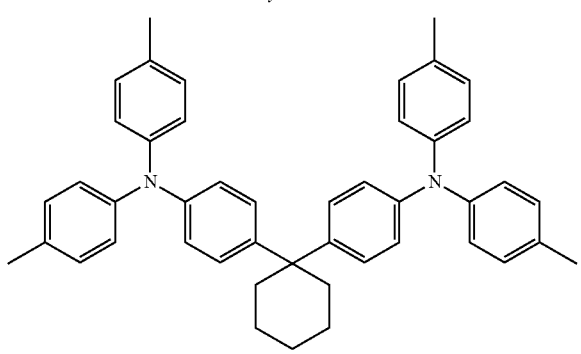

TAPC

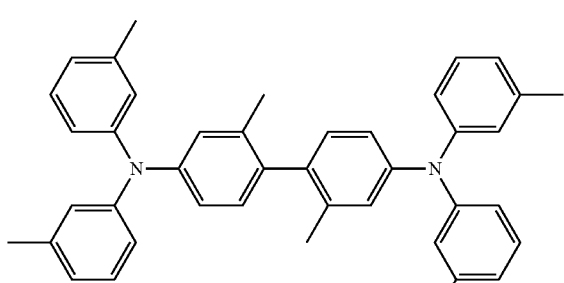

HMTPD

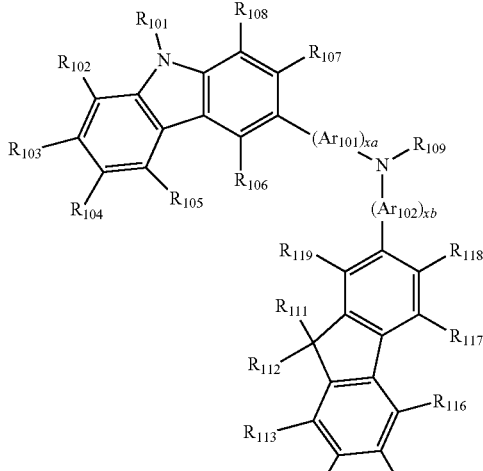

Formula 201

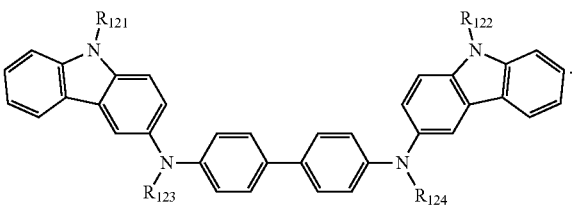

Formula 202

$Ar_{101}$ to $Ar_{102}$ in Formula 201 may each independently be a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylene group, a chrysenylenylene group, a naphthacenylene group, a picenylene group, a perylenylene group, or a pentacenylene group, each unsubstituted or substituted with deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ cycloalkenyl group, a $C_1$-$C_{10}$ heterocycloalkyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ arylalkyl group, a $C_1$-$C_{60}$ heteroaryl group, a $C_1$-$C_{60}$ heteroaryloxy group, a $C_1$-$C_{60}$ heteroarylthio group, a $C_2$-$C_{60}$ heteroarylalkyl group, a monovalent non-aromatic condensed polycyclic group, a monovalent non-aromatic condensed heteropolycyclic group, or any combination thereof.

xa and xb in Formula 201 may each independently be an integer from 0 to 5, or may be 0, 1 or 2. For example, xa may be 1 and xb may be 0, but xa and xb are not limited thereto.

$R_{101}$ to $R_{108}$, $R_{111}$ to $R_{119}$, and $R_{121}$ to $R_{124}$ in Formulae 201 and 202 may each independently be:

hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group (for example, a methyl group, an ethyl group, a propyl group, a butyl group, pentyl group, a hexyl group, and the like), or a $C_1$-$C_{10}$ alkoxy group (for example, a methoxy group, an ethoxy group, a propoxy group, a butoxy group, a pentoxy group, and the like);

a $C_1$-$C_{10}$ alkyl group or a $C_1$-$C_{10}$ alkoxy group, each substituted with deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, or any combination thereof; or a phenyl group, a naphthyl group, an anthracenyl group, a fluorenyl group, or a pyrenyl group, each unsubstituted or substituted with deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, or any combination thereof, but embodiments of the present disclosure are not limited thereto.

$R_{109}$ in Formula 201 may be a phenyl group, a naphthyl group, an anthracenyl group, or a pyridinyl group, each unsubstituted or substituted with deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, an anthracenyl group, a pyridinyl group, or any combination thereof.

In an embodiment, the compound represented by Formula 201 may be represented by Formula 201A, but embodiments of the present disclosure are not limited thereto:

Formula 201A

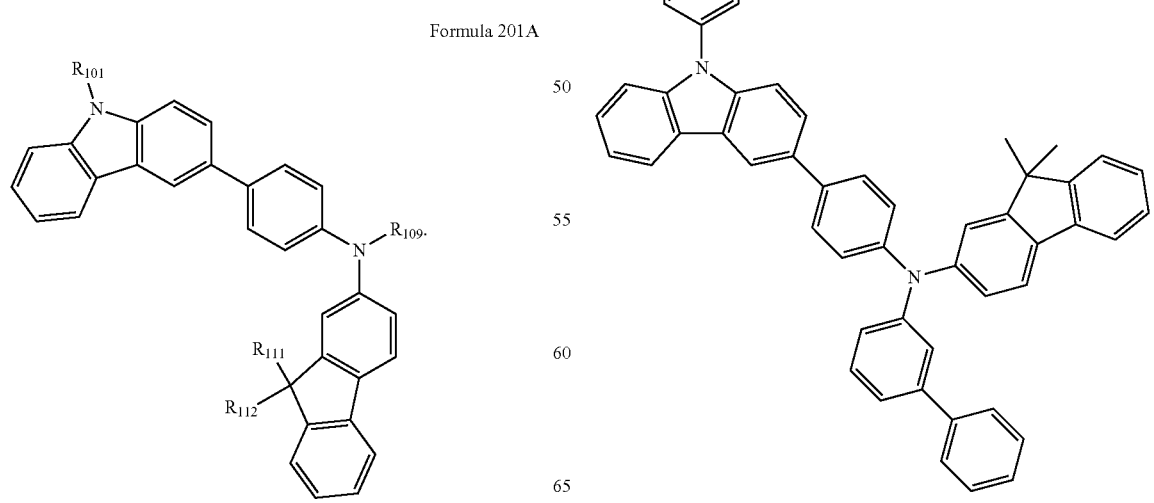

Detailed descriptions of $R_{101}$, $R_{111}$, $R_{112}$, and $R_{109}$ in Formula 201A are the same as described provided herein.

For example, the compound represented by Formula 201 and the compound represented by Formula 202 may each include one of Compounds HT1 to HT20 or any combination thereof, but embodiments of the present disclosure are not limited thereto:

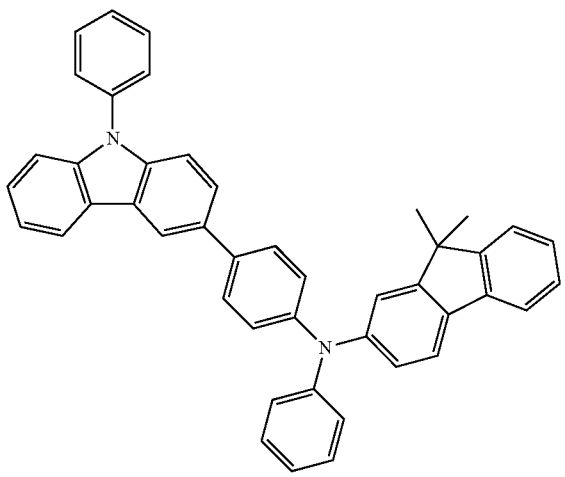

HT3
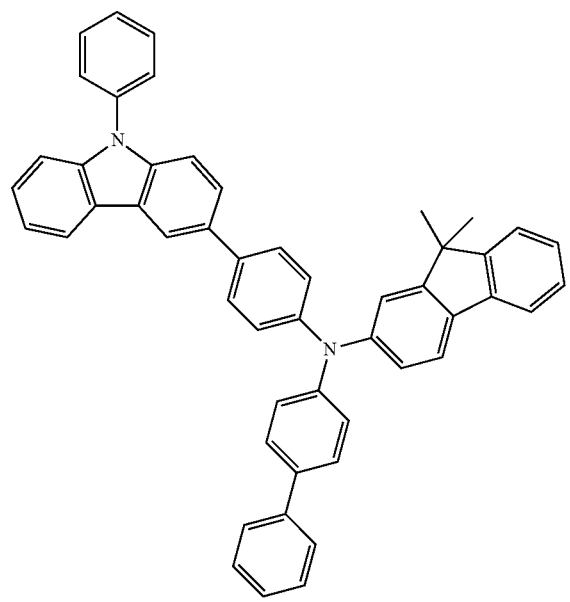
HT5
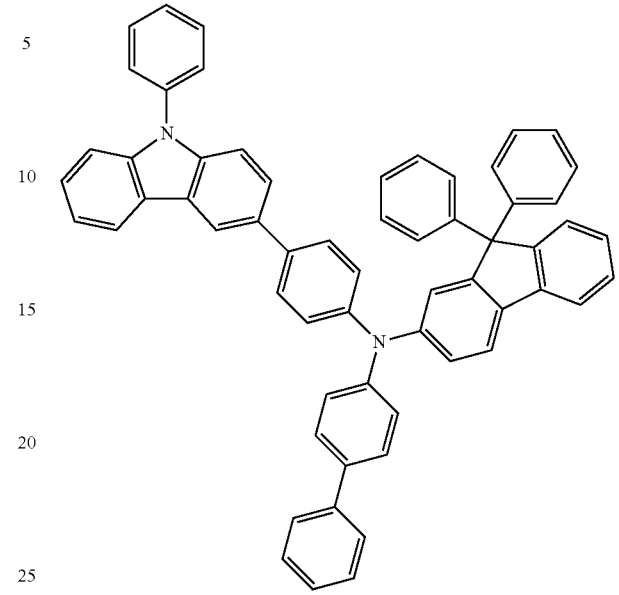
HT4
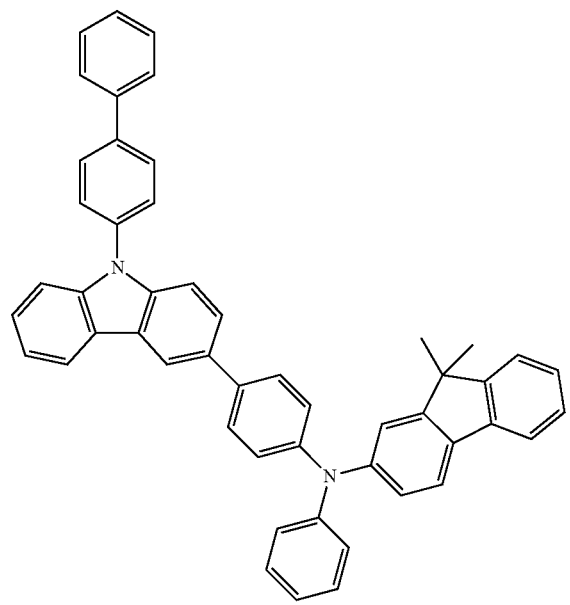
HT6
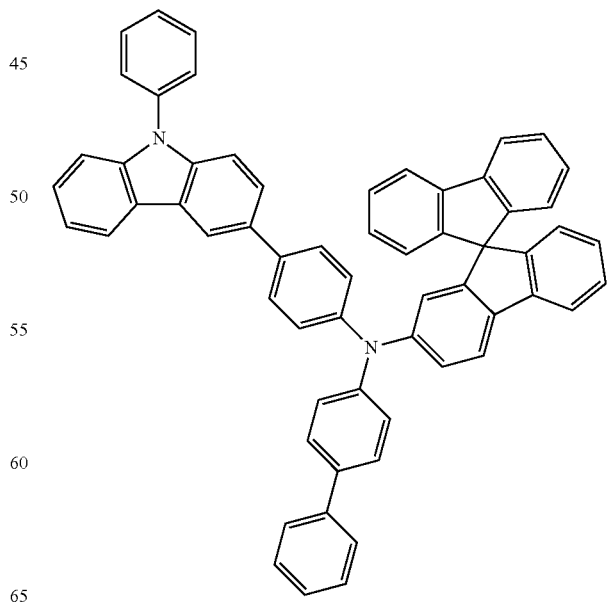

HT7
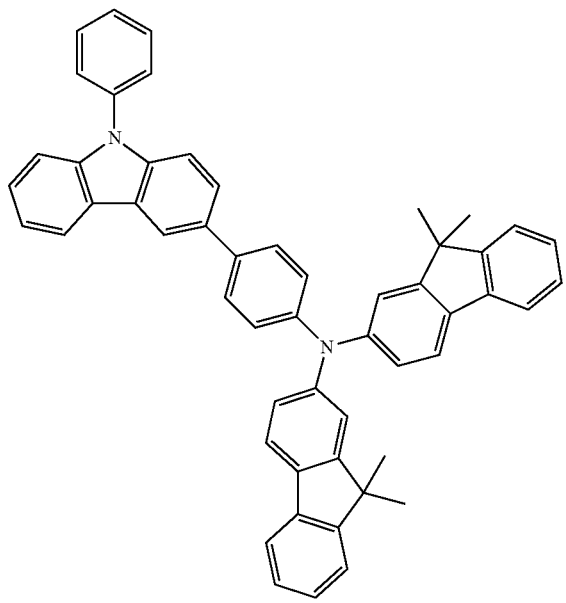
HT8
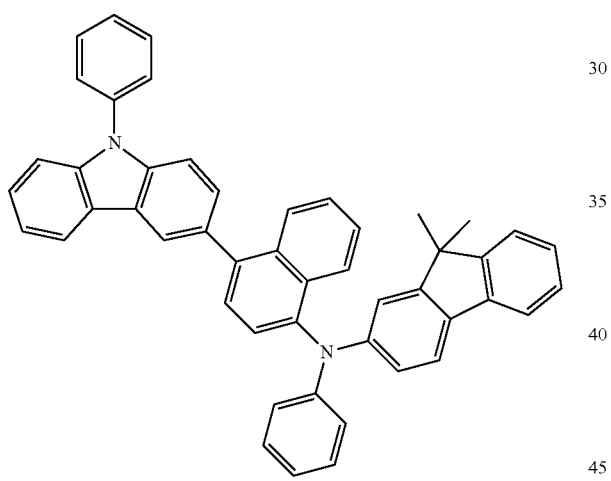
HT9
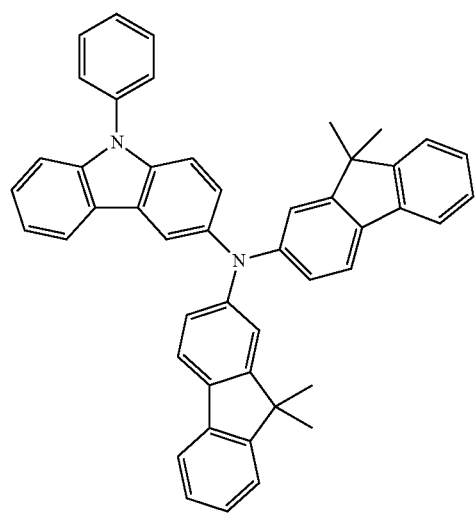
HT10
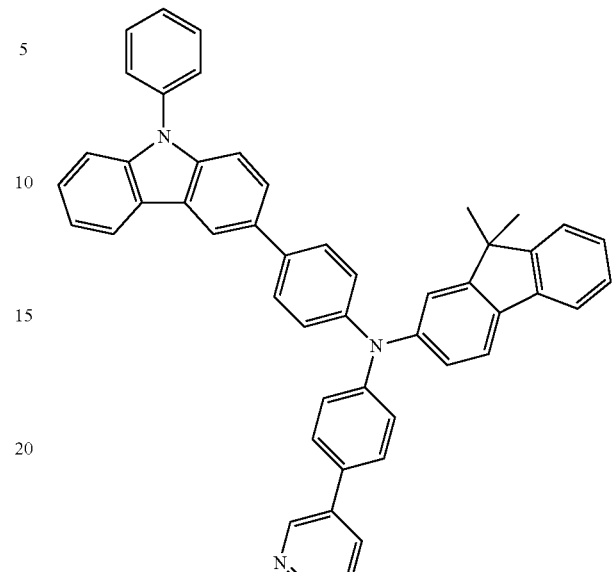
HT11
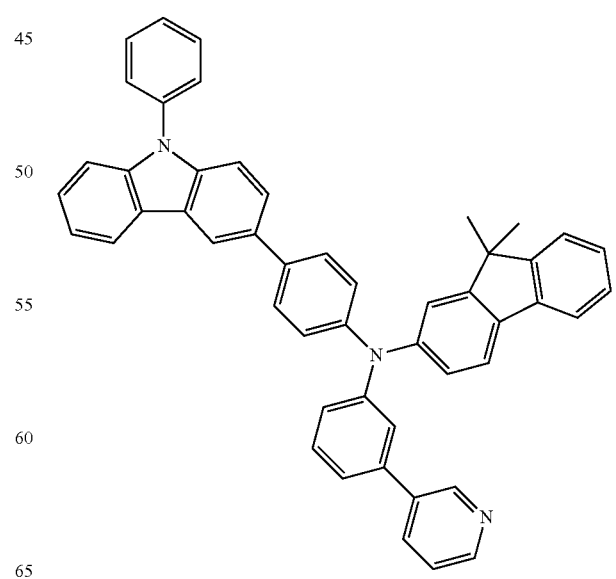

HT12
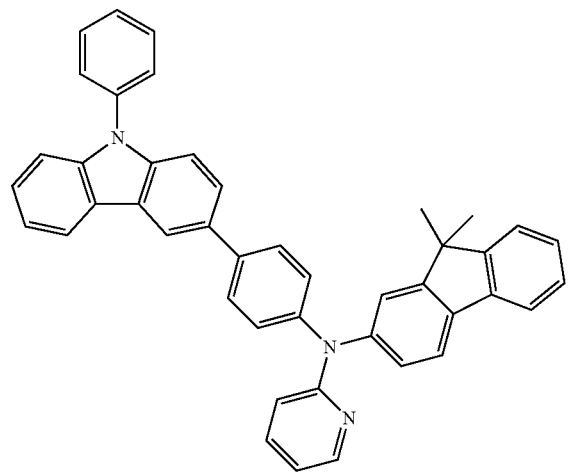
HT13
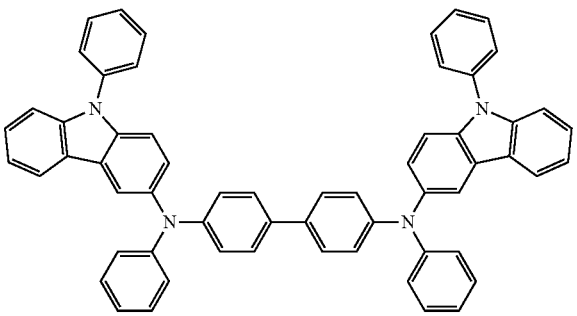
HT14
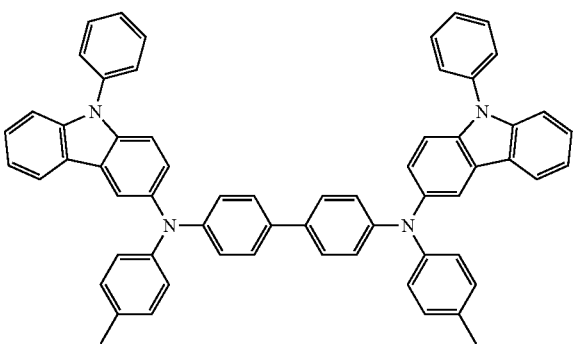
HT15
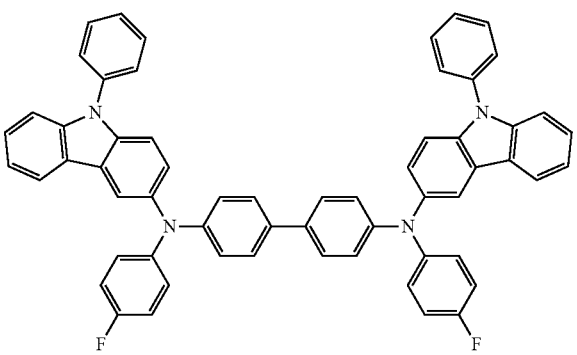
HT16
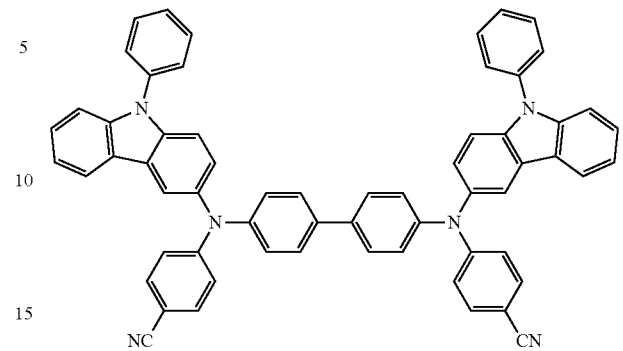
HT17
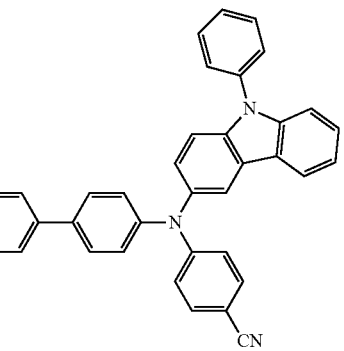
HT18
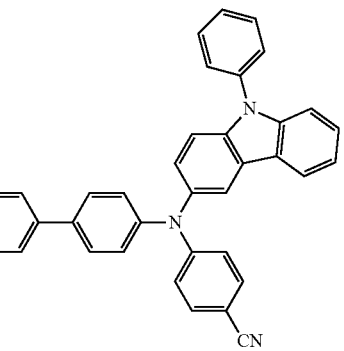
HT19

HT20

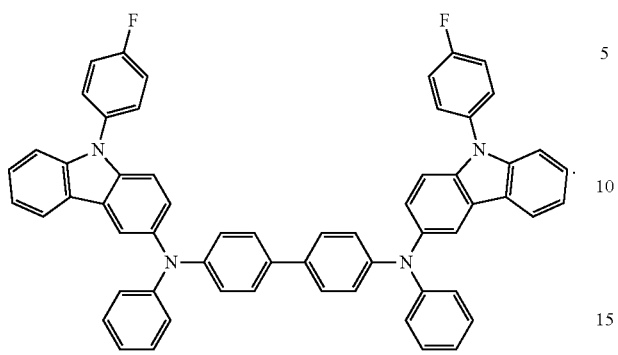

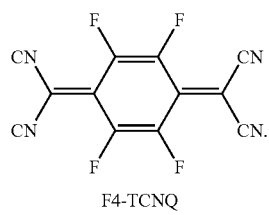

F4-TCNQ

A thickness of the hole transport region may be from about 100 Å to about 10,000 Å, for example, about 100 Å to about 1,000 Å. When the hole transport region includes at least one of a hole injection layer and a hole transport layer, a thickness of the hole injection layer may be in a range of about 100 Å to about 10,000 Å, for example, about 100 Å to about 1,000 Å, and a thickness of the hole transport layer may be in a range of about 50 Å to about 2,000 Å, for example about 100 Å to about 1,500 Å. While not wishing to be bound by theory, it is understood that when the thicknesses of the hole transport region, the hole injection layer, and the hole transport layer are within these ranges, satisfactory hole transporting characteristics may be obtained without a substantial increase in driving voltage.

The hole transport region may further include, in addition to these materials, a charge-generation material for the improvement of conductive properties. The charge-generation material may be homogeneously or non-homogeneously dispersed in the hole transport region.

The charge-generation material may be, for example, a p-dopant. The p-dopant may be a quinone derivative, a metal oxide, a cyano group-containing compound, or any combination thereof, but embodiments of the present disclosure are not limited thereto. Non-limiting examples of the p-dopant are a quinone derivative, such as tetracyanoquinonedimethane (TCNQ) or 2,3,5,6-tetrafluoro-tetracyano-1,4-benzoquinonedimethane (F4-TCNQ); a metal oxide, such as a tungsten oxide or a molybdenum oxide; and a cyano group-containing compound, such as Compound HT-D1 below, but are not limited thereto:

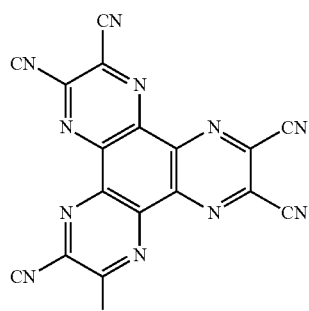

HT-D1

The hole transport region may include a buffer layer.

Also, the buffer layer may compensate for an optical resonance distance according to a wavelength of light emitted from the emission layer, and thus, efficiency of a formed organic light-emitting device may be improved.

Meanwhile, when the hole transport region includes an electron blocking layer, a material for the electron blocking layer may be materials for the hole transport region described above, materials for a host to be explained later, or any combination thereof. However, the material for the electron blocking layer is not limited thereto. For example, when the hole transport region includes an electron blocking layer, a material for the electron blocking layer may be mCP, which will be explained later.

Then, an emission layer may be formed on the hole transport region by vacuum deposition, spin coating, casting, LB deposition, or the like. When the emission layer is formed by vacuum deposition or spin coating, the deposition or coating conditions may be similar to those applied in forming the hole injection layer although the deposition or coating conditions may vary according to a compound that is used to form the emission layer.

The emission layer may include a host and a dopant, and the dopant may include the organometallic compound represented by Formula 1.

The host may include TPBi, TBADN, ADN (also referred to as "DNA"), CBP, CDBP, TCP, mCP, Compounds H50, Compound H51, Compound H52, or any combination thereof:

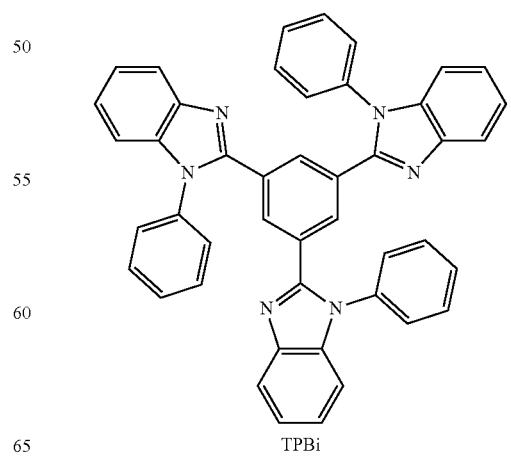

TPBi

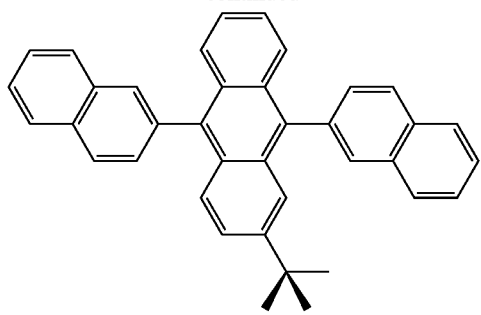

TBADN

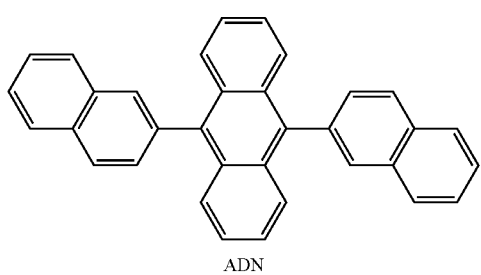

ADN

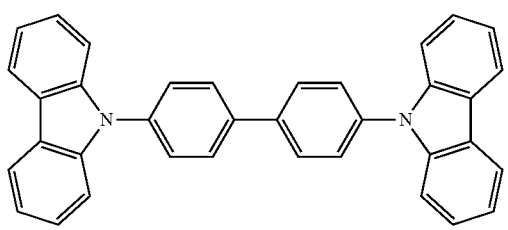

CBP

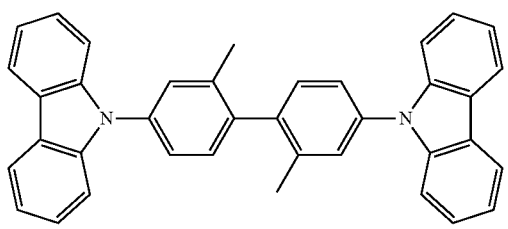

CDBP

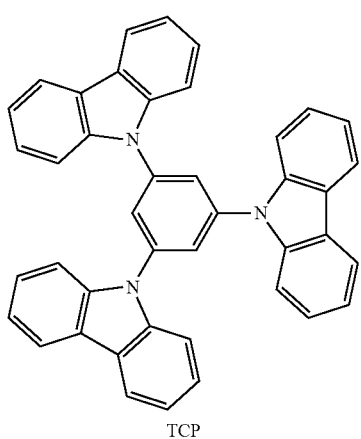

TCP

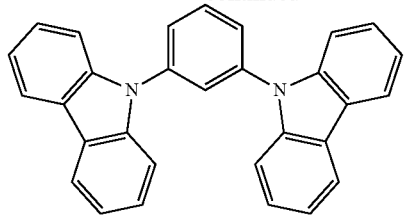

mCP

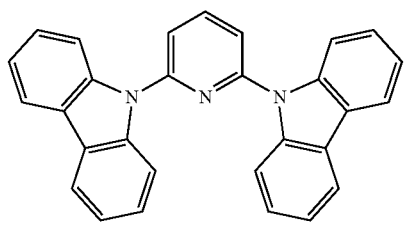

H50

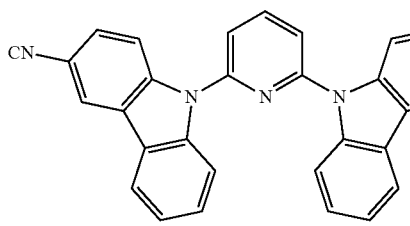

H51

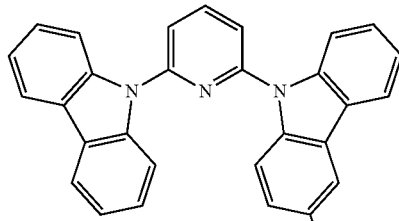

H52

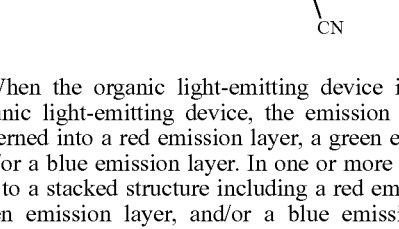

When the organic light-emitting device is a full-color organic light-emitting device, the emission layer may be patterned into a red emission layer, a green emission layer, and/or a blue emission layer. In one or more embodiments, due to a stacked structure including a red emission layer, a green emission layer, and/or a blue emission layer, the emission layer may emit white light.

When the emission layer includes a host and a dopant, an amount of the dopant may be in a range of about 0.01 parts by weight to about 15 parts by weight based on 100 parts by weight of the host, but embodiments of the present disclosure are not limited thereto.

A thickness of the emission layer may be in a range of about 100 Å to about 1,000 Å, for example, about 200 Å to about 600 Å. While not wishing to be bound by theory, it is understood that when the thickness of the emission layer is within this range, excellent light-emission characteristics may be obtained without a substantial increase in driving voltage.

Then, an electron transport region may be disposed on the emission layer.

The electron transport region may include a hole blocking layer, an electron transport layer, an electron injection layer, or any combination thereof.

For example, the electron transport region may have a hole blocking layer/electron transport layer/electron injection layer structure or an electron transport layer/electron injection layer structure, but the structure of the electron transport region is not limited thereto. The electron transport layer may have a single-layered structure or a multi-layered structure including two or more different materials.

Conditions for forming the hole blocking layer, the electron transport layer, and the electron injection layer which constitute the electron transport region may be understood by referring to the conditions for forming the hole injection layer.

When the electron transport region includes a hole blocking layer, the hole blocking layer may include, for example, BCP, BPhen, BAlq, or any combination thereof, but embodiments of the present disclosure are not limited thereto:

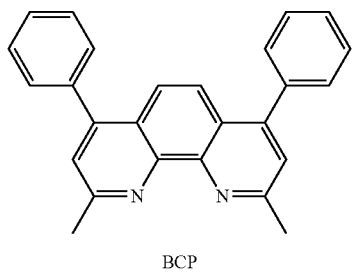

BCP

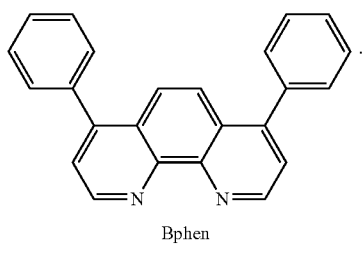

Bphen

A thickness of the hole blocking layer may be from about 20 Å to about 1,000 Å, for example, about 30 Å to about 300 Å. While not wishing to be bound by theory, it is understood that when the thickness of the hole blocking layer is within these ranges, the hole blocking layer may have excellent hole blocking characteristics without a substantial increase in driving voltage.

The electron transport layer may include BOP, BPhen, $Alq_3$, BAlq, TAZ, NTAZ, or any combination thereof:

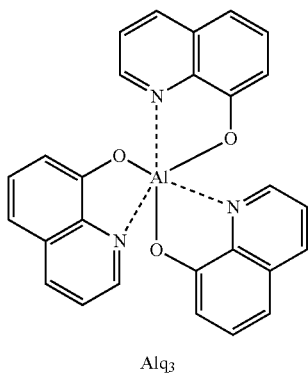

$Alq_3$

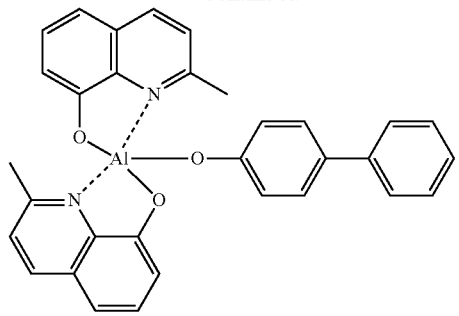

BAlq

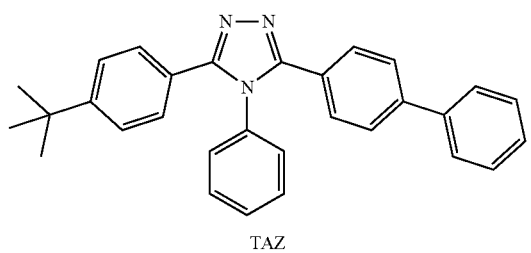

TAZ

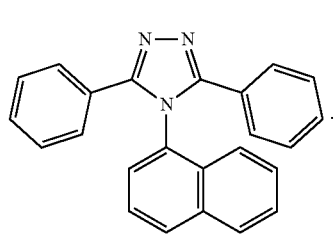

NTAZ

In one or more embodiments, the electron transport layer may include at least one of ET1 to ET25, but are not limited thereto:

ET1

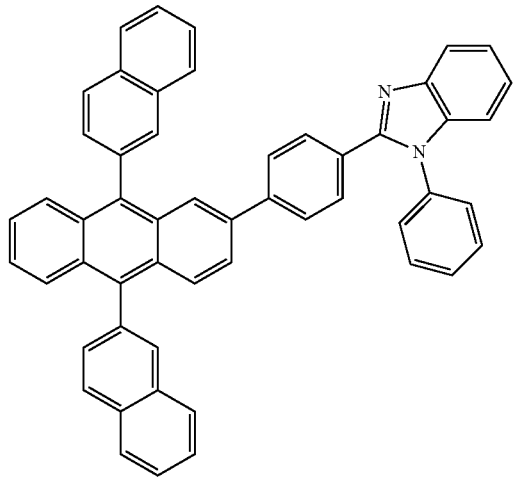

ET2
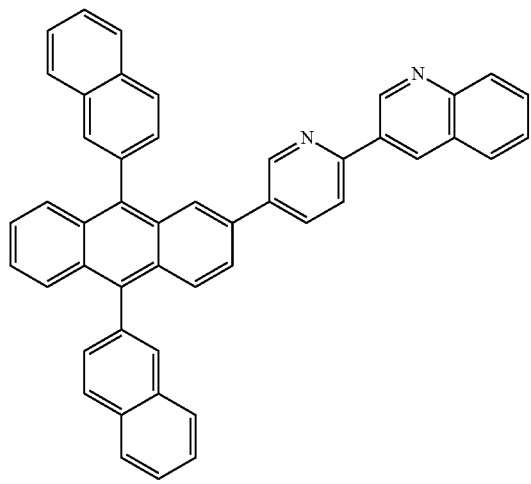
ET3
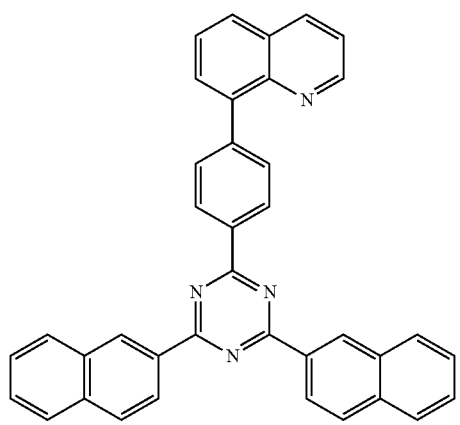
ET4
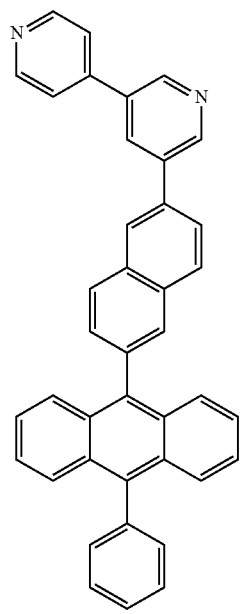
ET5
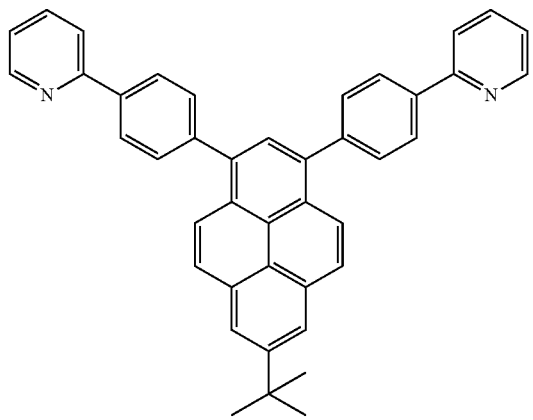
ET6
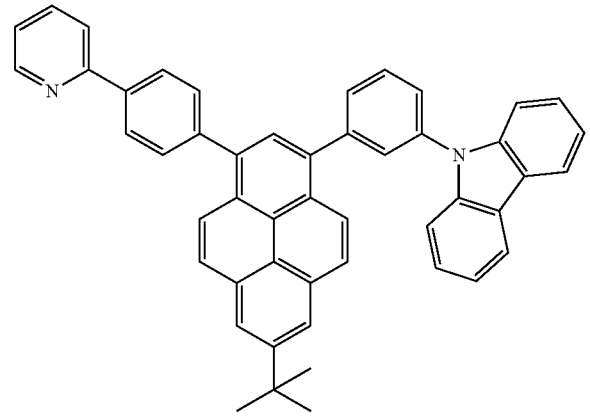
ET7
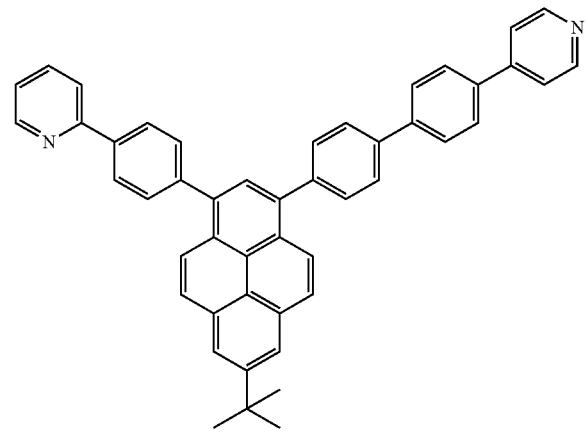

ET8
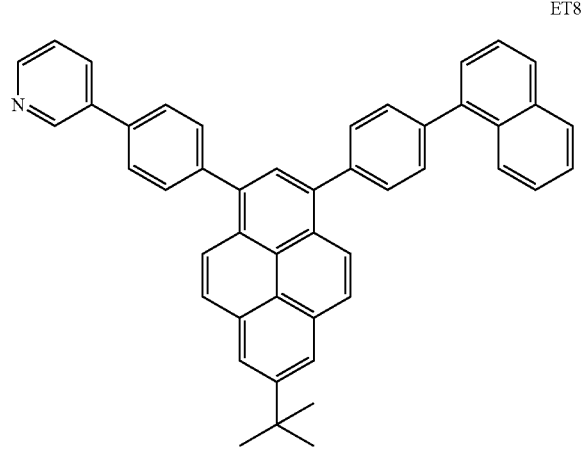
ET9
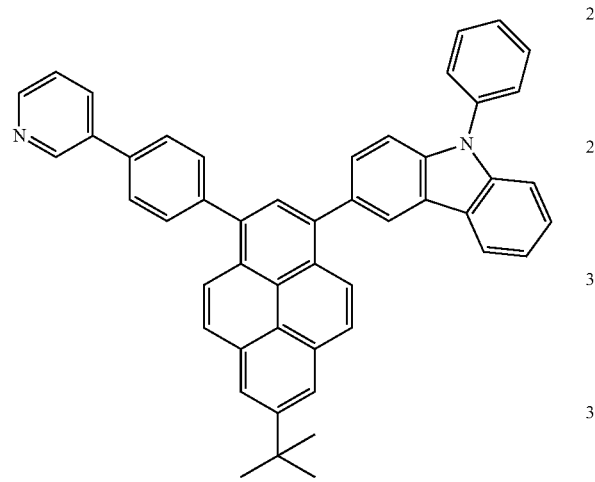
ET10
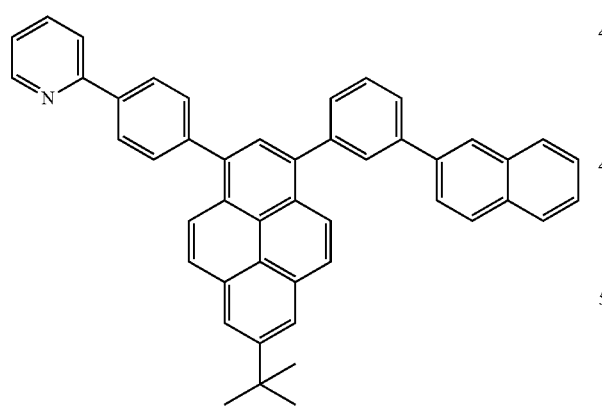
ET11
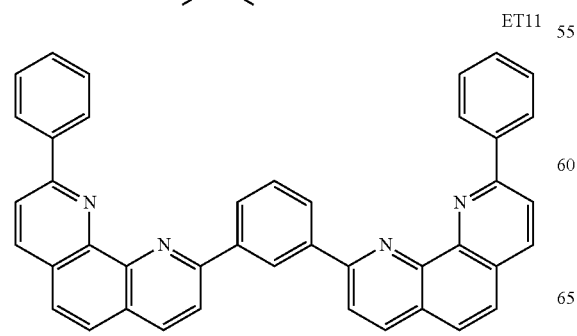
ET12
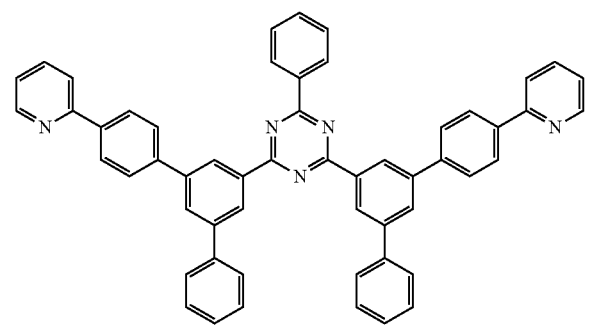
ET13
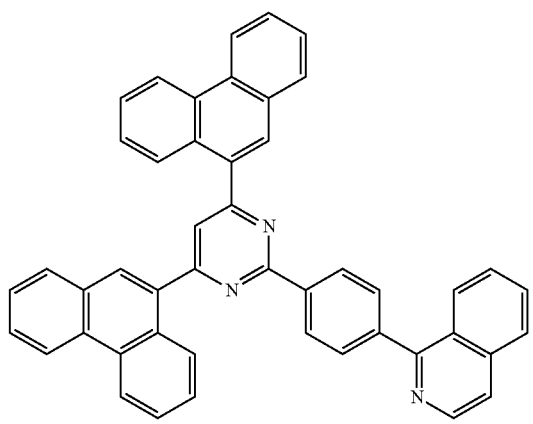
ET14
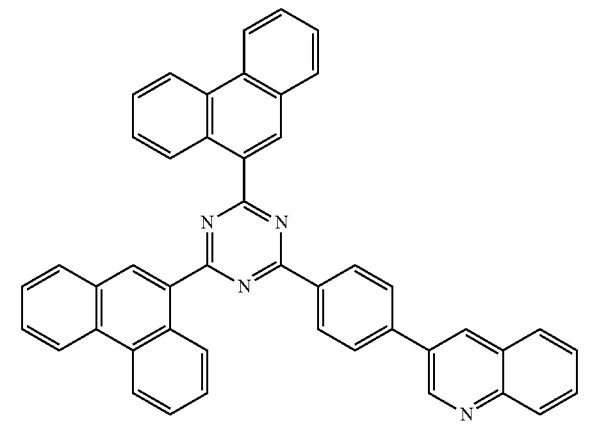
ET15
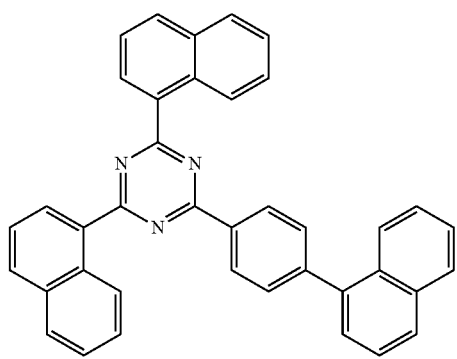

ET16
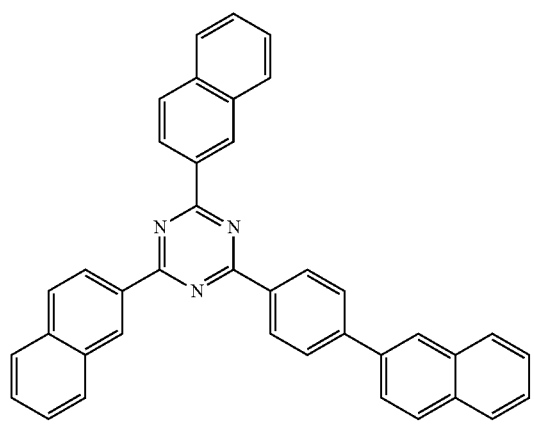
ET17
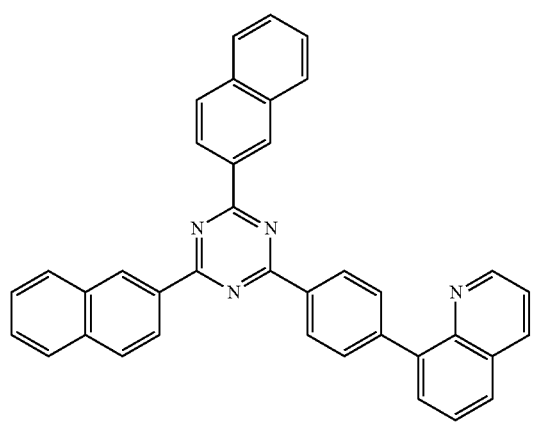
ET18
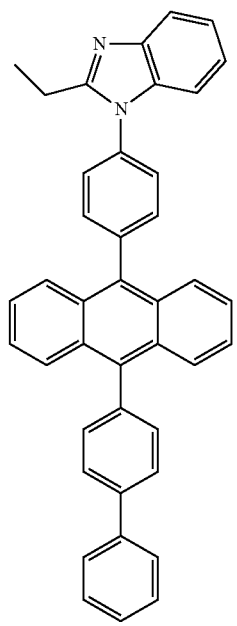
ET19
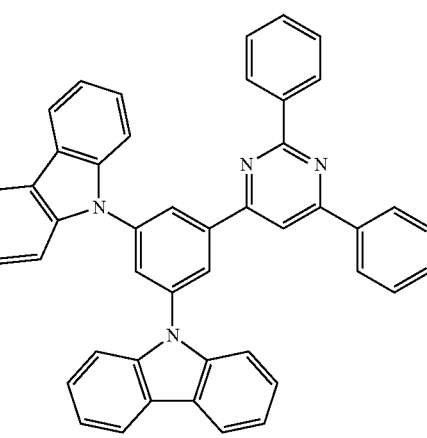
ET20
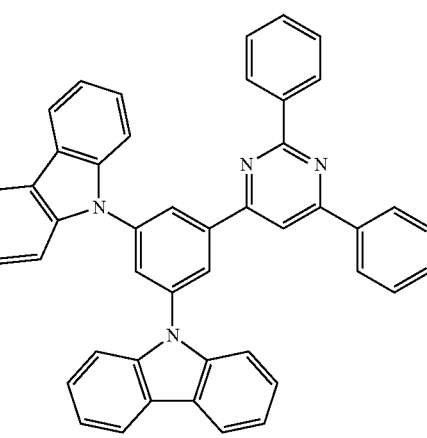
ET21
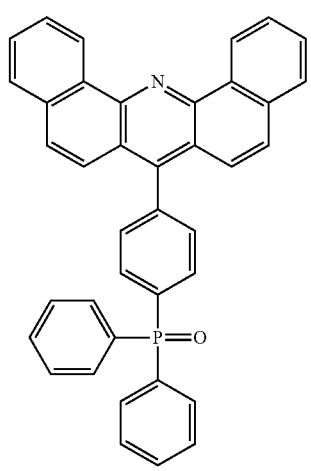

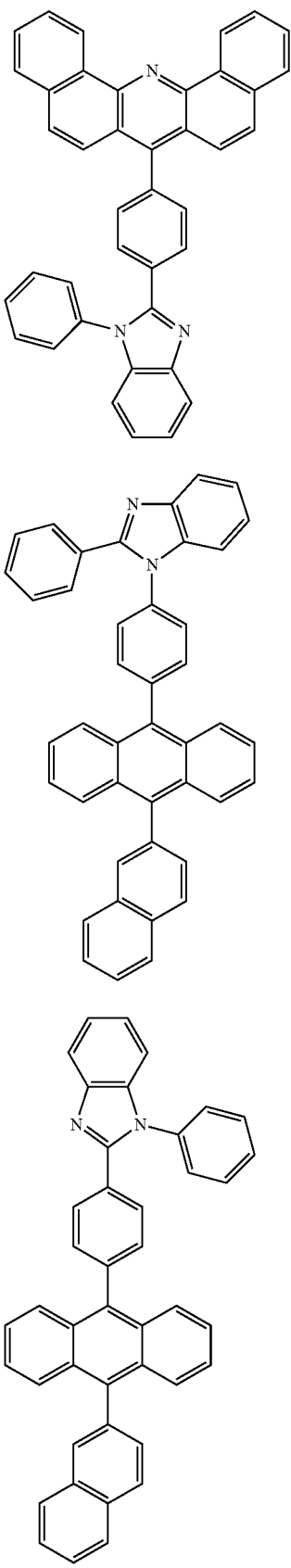

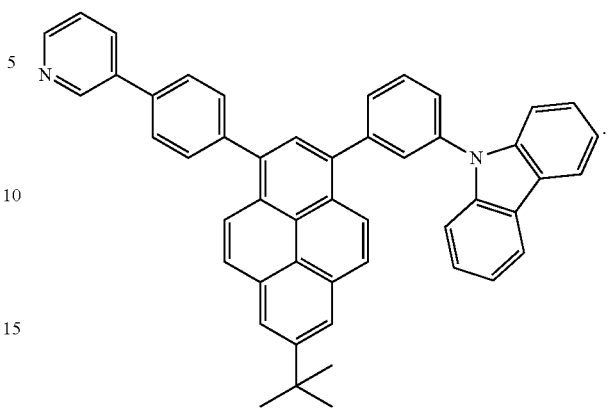

A thickness of the electron transport layer may be from about 100 Å to about 1,000 Å, for example, about 150 Å to about 500 Å. While not wishing to be bound by theory, it is understood that when the thickness of the electron transport layer is within the range described above, the electron transport layer may have satisfactory electron transport characteristics without a substantial increase in driving voltage.

Also, the electron transport layer may further include, in addition to the materials described above, a metal-containing material.

The metal-containing material may include a Li complex. The Li complex may include, for example, Compound ET-D1 (LiQ), Compound ET-D2, or combination thereof:

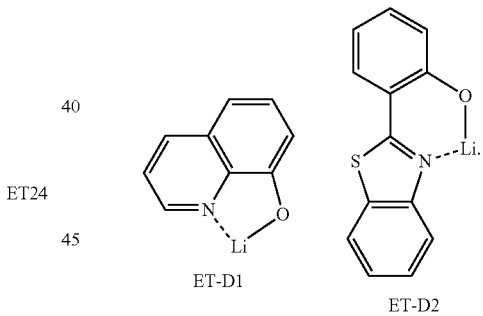

The electron transport region may include an electron injection layer that promotes flow of electrons from the second electrode 19 thereinto.

The electron injection layer may include LiF, NaCl, CsF, Li$_2$O, BaO, or any combination thereof.

A thickness of the electron injection layer may be from about 1 Å to about 100 Å, for example, about 3 Å to about 90 Å. While not wishing to be bound by theory, it is understood that when a thickness of the electron injection layer is within these ranges, satisfactory electron injection characteristics may be obtained without substantial increase in driving voltage.

The second electrode 19 is disposed on the organic layer 15. The second electrode 19 may be a cathode. A material for forming the second electrode 19 may be a metal, an alloy, an electrically conductive compound, or a combination thereof, which have a relatively low work function. For example, lithium (Li), magnesium (Mg), aluminum (Al), aluminum-lithium (Al—Li), calcium (Ca), magnesium-indium (Mg—In), or magnesium-silver (Mg—Ag) may be formed as the material for forming the second electrode 19. To manufacture a top-emission type light-emitting device, a transmissive electrode formed using ITO or IZO may be used as the second electrode 19.

Hereinbefore, the organic light-emitting device according to an embodiment has been described in connection with the FIGURE.

Another aspect of the present disclosure provides a diagnostic composition including at least one of the organometallic compound represented by Formula 1.

The organometallic compound represented by Formula 1 provides high luminescent efficiency. Accordingly, a diagnostic composition including the organometallic compound may have high diagnostic efficiency.

The diagnostic composition may be used in various applications including a diagnosis kit, a diagnosis reagent, a biosensor, and a biomarker.

The term "$C_1$-$C_{60}$ alkyl group" as used herein refers to a linear or branched saturated aliphatic hydrocarbon monovalent group having 1 to 60 carbon atoms, and examples thereof include a methyl group, an ethyl group, a propyl group, an isobutyl group, a sec-butyl group, a tert-butyl group, a pentyl group, an isoamyl group, and a hexyl group. The term "$C_1$-$C_{60}$ alkylene group" as used herein refers to a divalent group having the same structure as the $C_1$-$C_{60}$ alkyl group.

The term "$C_1$-$C_{60}$ alkoxy group" as used herein refers to a monovalent group represented by —$OA_{101}$ (wherein $A_{101}$ is the $C_1$-$C_{60}$ alkyl group), and examples thereof include a methoxy group, an ethoxy group, and an iso-propyloxy group.

The term "$C_2$-$C_{60}$ alkenyl group" as used herein refers to a hydrocarbon group having at least one carbon-carbon double bond in the middle or at the terminus of the $C_2$-$C_{60}$ alkyl group, and examples thereof include an ethenyl group, a propenyl group, and a butenyl group. The term "$C_2$-$C_{60}$ alkenylene group" as used herein refers to a divalent group having the same structure as the $C_2$-$C_{60}$ alkenyl group.

The term "$C_2$-$C_{60}$ alkynyl group" as used herein refers to a hydrocarbon group having at least one carbon-carbon triple bond in the middle or at the terminus of the $C_2$-$C_{60}$ alkyl group, and examples thereof include an ethynyl group, and a propynyl group. The term "$C_2$-$C_{60}$ alkynylene group" as used herein refers to a divalent group having the same structure as the $C_2$-$C_{60}$ alkynyl group.

The term "$C_3$-$C_{10}$ cycloalkyl group" as used herein refers to a monovalent saturated hydrocarbon monocyclic group having 3 to 10 carbon atoms, and non-limiting examples thereof include a cyclopentyl group, a cyclohexyl group, a cycloheptyl group, a cyclooctyl group, an adamantanyl group, a norbornanyl group, a bicyclo[1.1.1]pentyl group, a bicyclo[2.1.1]hexyl group, a bicyclo[2.2.1]heptyl group, and a bicyclo[2.2.2]octyl group. The term "$C_3$-$C_{10}$ cycloalkylene group" as used herein refers to a divalent group having the same structure as the $C_3$-$C_{10}$ cycloalkyl group.

The term "$C_1$-$C_{10}$ heterocycloalkyl group" as used herein refers to a monovalent saturated monocyclic group having at least one heteroatom selected from N, O, P, Si and S as a ring-forming atom and 1 to 10 carbon atoms, and non-limiting examples thereof include a tetrahydrofuranyl group and a tetrahydrothiophenyl group. The term "$C_1$-$C_{10}$ heterocycloalkylene group" as used herein refers to a divalent group having the same structure as the $C_1$-$C_{10}$ heterocycloalkyl group.

The term "$C_3$-$C_{10}$ cycloalkenyl group" as used herein refers to a monovalent monocyclic group that has 3 to 10 carbon atom, at least one carbon-carbon double bond in its ring, and no aromaticity, and a non-limiting example thereof includes a cycloheptenyl group. The term "$C_3$-$C_{10}$ cycloalkenylene group" as used herein refers to a divalent group having the same structure as the $C_3$-$C_{10}$ cycloalkenyl group.

The term "$C_1$-$C_{10}$ heterocycloalkenyl group" as used herein refers to a monovalent monocyclic group that has at least one heteroatom selected from N, O, P, Si, and S as a ring-forming atom, 1 to 10 carbon atoms, and at least one double bond in its ring. Non-limiting examples of the $C_1$-$C_{10}$ heterocycloalkenyl group include a 2,3-dihydrofuranyl group and a 2,3-dihydrothiophenyl group. The term "$C_1$-$C_{10}$ heterocycloalkenylene group" as used herein refers to a divalent group having the same structure as the $C_1$-$C_{10}$ heterocycloalkenyl group.

The term "$C_6$-$C_{60}$ aryl group" as used herein refers to a monovalent group having a monovalent carbocyclic aromatic system having 6 to 60 carbon atoms, and the term "$C_6$-$C_{60}$ arylene group" as used herein refers to a divalent group having a carbocyclic aromatic system having 6 to 60 carbon atoms. Non-limiting examples of the $C_6$-$C_{60}$ aryl group include a phenyl group, a naphthyl group, an anthracenyl group, a phenanthrenyl group, a pyrenyl group, and a chrysenyl group. When the $C_6$-$C_{60}$ aryl group and the $C_6$-$C_{60}$ arylene group each include two or more rings, the rings may be fused to each other.

The term "$C_1$-$C_{60}$ heteroaryl group" as used herein refers to a monovalent group having a heterocyclic aromatic system that has at least one heteroatom selected from N, O, P, Si, and S as a ring-forming atom, in addition to 1 to 60 carbon atoms. The term "$C_1$-$C_{60}$ heteroarylene group" as used herein refers to a divalent group having a heterocyclic aromatic system that has at least one heteroatom selected from N, O, P, Si, and S as a ring-forming atom, in addition to 1 to 60 carbon atoms. Non-limiting examples of the $C_1$-$C_{60}$ heteroaryl group include a pyridinyl group, a pyrimidinyl group, a pyrazinyl group, a pyridazinyl group, a triazinyl group, a quinolinyl group, and an isoquinolinyl group. When the $C_1$-$C_{60}$ heteroaryl group and the $C_1$-$C_{60}$ heteroarylene group each include two or more rings, the rings may be fused to each other.

The term "$C_6$-$C_{60}$ aryloxy group" as used herein indicates —$OA_{102}$ (wherein $A_{102}$ is the $C_6$-$C_{60}$ aryl group), the term "$C_6$-$C_{60}$ arylthio group" as used herein indicates —$SA_{103}$ (wherein $A_{103}$ is the $C_6$-$C_{60}$ aryl group), and the term "$C_7$-$C_{60}$ arylalkyl group" as used herein indicates -$A_{104}A_{105}$ (wherein $A_{105}$ is the $C_6$-$C_{59}$ aryl group and $A_{104}$ is the $C_1$-$C_{53}$ alkylene group).

The term "$C_1$-$C_{60}$ heteroaryloxy group" as used herein refers to —$OA_{106}$ (wherein $A_{106}$ is the $C_2$-$C_{60}$ heteroaryl group), the term "$C_1$-$C_{60}$ heteroarylthio group" as used herein indicates —$SA_{107}$ (wherein $A_{107}$ is the $C_1$-$C_{60}$ heteroaryl group), and the term "$C_2$-$C_{60}$ heteroarylalkyl group" as used herein refers to -$A_{108}A_{109}$ ($A_{109}$ is a $C_1$-$C_{59}$ heteroaryl group, and $A_{108}$ is a $C_1$-$C_{59}$ alkylene group).

The term "monovalent non-aromatic condensed polycyclic group" as used herein refers to a monovalent group (for example, having 8 to 60 carbon atoms) having two or more rings condensed to each other, only carbon atoms as ring-forming atoms, and no aromaticity in its entire molecular structure. A non-limiting example of the monovalent non-aromatic condensed polycyclic group includes a fluorenyl group. The term "divalent non-aromatic condensed polycyclic group" as used herein refers to a divalent group having the same structure as the monovalent non-aromatic condensed polycyclic group.

The term "monovalent non-aromatic condensed heteropolycyclic group" as used herein refers to a monovalent group (for example, having 2 to 60 carbon atoms) having two or more rings condensed to each other, a heteroatom selected from N, O, P, Si, and S, other than carbon atoms, as a ring-forming atom, and no aromaticity in its entire molecular structure. A non-limiting example of the monovalent non-aromatic condensed heteropolycyclic group includes a carbazolyl group. The term "divalent non-aromatic condensed heteropolycyclic group" as used herein refers to a divalent group having the same structure as the monovalent non-aromatic condensed heteropolycyclic group.

The term "$C_5$-$C_{60}$ carbocyclic group" as used herein refers to a saturated or unsaturated cyclic group having, as a ring-forming atom, 5 to 60 carbon atoms only. The $C_5$-$C_{60}$ carbocyclic group may be a monocyclic group or a polycyclic group.

The term "$C_1$-$C_{60}$ heterocyclic group" as used herein refers to a saturated or unsaturated cyclic group having, as a ring-forming atom, at least one heteroatom selected from N, O, Si, P, and S other than 1 to 60 carbon atoms. The $C_1$-$C_{60}$ heterocyclic group may be a monocyclic group or a polycyclic group.

A substituent(s) of the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_7$-$C_{60}$ arylalkyl group, the substituted $C_1$-$C_{60}$ heteroaryl group, the substituted $C_1$-$C_{60}$ heteroaryloxy group, the substituted $C_1$-$C_{60}$ heteroarylthio group, the substituted $C_2$-$C_{60}$ heteroarylalkyl group, the substituted monovalent non-aromatic condensed polycyclic group, and the substituted monovalent non-aromatic condensed heteropolycyclic group may each independently be:

deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, or a $C_1$-$C_{60}$ alkoxy group;

a $C_1$-$C_{60}$ alkyl group, a $C_2$-$C_{60}$ alkenyl group, a $C_2$-$C_{60}$ alkynyl group, or a $C_1$-$C_{60}$ alkoxy group, each substituted with deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ arylalkyl group, a $C_1$-$C_{60}$ heteroaryl group, a $C_1$-$C_{60}$ heteroaryloxy group, a $C_1$-$C_{60}$ heteroarylthio group, a $C_2$-$C_{60}$ heteroarylalkyl group, a monovalent non-aromatic condensed polycyclic group, —N($Q_{11}$)($Q_{12}$), —Si($Q_{13}$)($Q_{14}$)($Q_{15}$), —Ge($Q_{13}$)($Q_{14}$)($Q_{15}$), —B($Q_{16}$)($Q_{17}$), —P(=O)($Q_{18}$)($Q_{19}$), —P($Q_{18}$)($Q_{19}$), or any combination thereof;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ arylalkyl group, a $C_1$-$C_{60}$ heteroaryl group, a $C_1$-$C_{60}$ heteroaryloxy group, a $C_1$-$C_{60}$ heteroarylthio group, a $C_2$-$C_{60}$ heteroarylalkyl group, a monovalent non-aromatic condensed polycyclic group, or a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ arylalkyl group, a $C_1$-$C_{60}$ heteroaryl group, a $C_1$-$C_{60}$ heteroaryloxy group, a $C_1$-$C_{60}$ heteroarylthio group, a $C_2$-$C_{60}$ heteroarylalkyl group, a monovalent non-aromatic condensed polycyclic group, or a monovalent non-aromatic condensed heteropolycyclic group, each substituted with deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ arylalkyl group, a $C_1$-$C_{60}$ heteroaryl group, a $C_1$-$C_{60}$ heteroaryloxy group, a $C_1$-$C_{60}$ heteroarylthio group, a $C_2$-$C_{60}$ heteroarylalkyl group, a monovalent non-aromatic condensed polycyclic group, a monovalent non-aromatic condensed heteropolycyclic group, —N($Q_{21}$)($Q_{22}$), —Si($Q_{23}$)($Q_{24}$)($Q_{25}$), —Ge($Q_{23}$)($Q_{24}$)($Q_{25}$), —B($Q_{26}$)($Q_{27}$), —P(=O)($Q_{28}$)($Q_{29}$), —P($Q_{28}$)($Q_{29}$), or any combination thereof;

—N($Q_{31}$)($Q_{32}$), —Si($Q_{33}$)($Q_{34}$)($Q_{35}$), —Ge($Q_{33}$)($Q_{34}$)($Q_{35}$), —B($Q_{36}$)($Q_{37}$), —P(=O)($Q_{38}$)($Q_{39}$), or —P($Q_{38}$)($Q_{39}$), or any combination thereof.

In the present specification, $Q_1$ to $Q_9$, $Q_{11}$ to $Q_{19}$, $Q_{21}$ to $Q_{29}$, and $Q_{31}$ to $Q_{39}$ may each independently be hydrogen; deuterium; —F; —Cl; —Br; —I; a hydroxyl group; a cyano group; a nitro group; an amino group; an amidino group; a hydrazine group; a hydrazone group; a carboxylic acid group or a salt thereof; a sulfonic acid group or a salt thereof; a phosphoric acid group or a salt thereof; a $C_1$-$C_{60}$ alkyl group; a $C_2$-$C_{60}$ alkenyl group; a $C_2$-$C_{69}$ alkynyl group; a $C_1$-$C_{60}$ alkoxy group; a $C_3$-$C_{10}$ cycloalkyl group; a $C_1$-$C_{10}$ heterocycloalkyl group; a $C_3$-$C_{10}$ cycloalkenyl group; a $C_1$-$C_{10}$ heterocycloalkenyl group; a $C_6$-$C_{69}$ aryl group; a $C_6$-$C_{69}$ aryl group substituted with a $C_1$-$C_{60}$ alkyl group, a $C_6$-$C_{69}$ aryl group, or any combination thereof; a $C_6$-$C_{69}$ aryloxy group; a $C_6$-$C_{69}$ arylthio group; a $C_7$-$C_{69}$ arylalkyl group; a $C_1$-$C_{60}$ heteroaryl group; a $C_1$-$C_{60}$ heteroaryloxy group; a $C_1$-$C_{60}$ heteroarylthio group; a $C_2$-$C_{60}$ heteroarylalkyl group; a monovalent non-aromatic condensed polycyclic group, or a monovalent non-aromatic condensed heteropolycyclic group.

Hereinafter, a compound and an organic light-emitting device according to embodiments are described in detail with reference to Synthesis Example and Examples. However, the organic light-emitting device is not limited thereto.

The wording "B was used instead of A" used in describing Synthesis Examples means that an amount of A used was identical to an amount of B used, in terms of a molar equivalent.

EXAMPLES

Synthesis Example 1: Synthesis of Compound 2

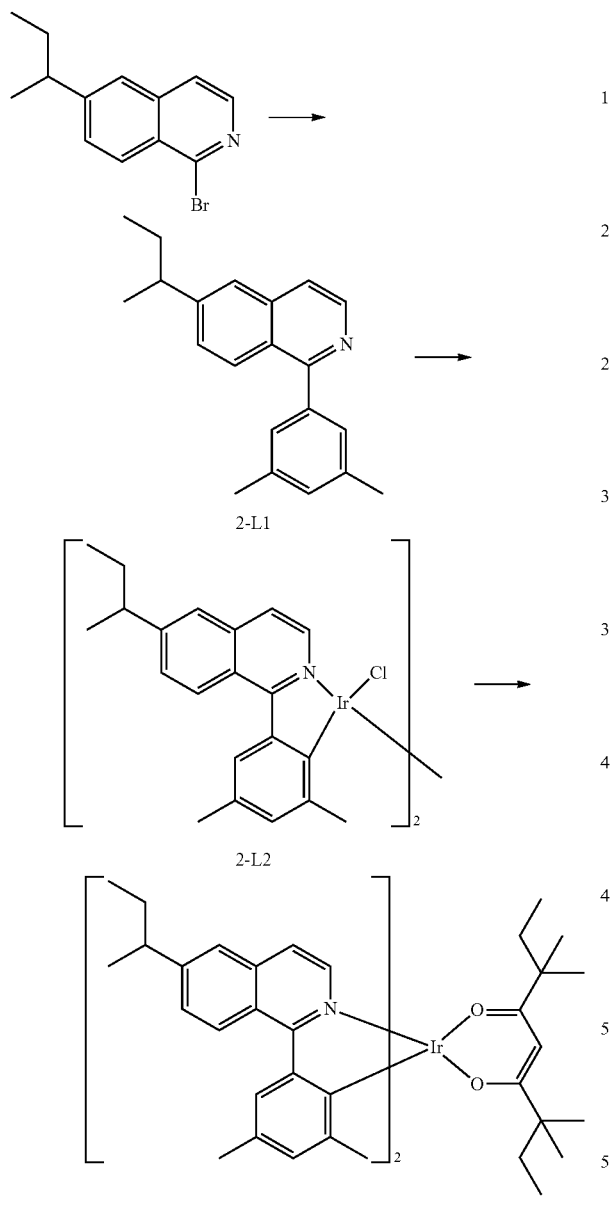

Synthesis of Intermediate 2-L1

1-bromo-6-(sec-butyl)isoquinoline (5.48 grams (g), 20.76 millimoles, mmol), (3,5-dimethylphenyl)boronic acid (4.67 g, 31.14 mmol), Pd(PPh$_3$)$_4$ (1.92 g, 1.66 mmol), and K$_2$CO$_3$ (7.17 g, 51.90 mmol), tetrahydrofuran (THF) (60 milliliters, mL), and distilled water (30 mL) were mixed together, and the mixed solution was stirred under reflux for 18 hours. Then, the reaction temperature was lowered to room temperature, and the reaction mixture was extracted by using methylene chloride (MC). The organic layer was dried by using anhydrous magnesium sulfate (MgSO$_4$) to remove moisture, and filtered. The filtrate was decompressed, and the residue was purified by using column chromatography under conditions of EA:Hexane=1:10, thereby obtaining 5.60 g (93%) of Intermediate 2-L1.

MALDI-TOFMS (m/z): C$_{21}$H$_{23}$N (M+) 289.

Synthesis of Intermediate 2-L2

Intermediate 2-L1 (5.58 g, 19.3 mmol), iridium chloride (3.02 g, 8.58 mmol), ethoxyethanol (45 mL), and distilled water (15 mL) were mixed together, and the mixed solution was stirred under reflux for 24 hours. The reaction temperature was lowered to room temperature, and a solid produced therefrom was separated by filtration. A filtrate was thoroughly washed by using water/methanol/hexane in the stated order, and a solid obtained therefrom was dried in a vacuum oven, thereby obtaining 3.9 g (57%) of Intermediate 2-L2.

Synthesis of Compound 2

Intermediate 2-L2 (1.56 g, 0.97 mmol), 3,3,7,7-tetramethylnonane-4,6-dione (2.06 g, 9.69 mmol), Na$_2$CO$_3$ (1.02 g, 9.69 mmol), and ethoxyethanol (20 mL) were mixed together, and the mixed solution was stirred for 24 hours. The mixture obtained therefrom was filtered, and the filtered solid was thoroughly washed by using ethanol and hexane, and purified by using column chromatography under conditions of dichloromethane:n-hexane=1:1 (v/v), thereby obtaining 1.40 g (74%) of Compound 2.

HRMS(MALDI) calcd for C$_{55}$H$_{67}$IrN$_2$O$_2$: m/z 980.37. Found: 980.39.

Synthesis Example 2: Synthesis of Compound 1

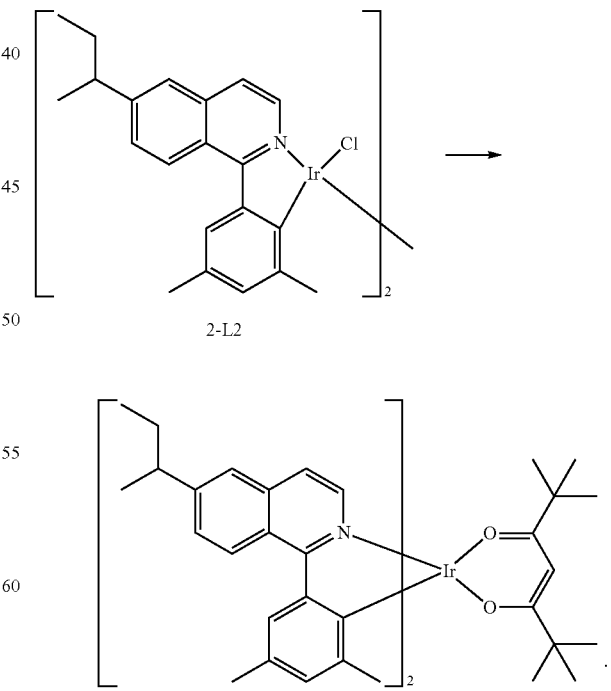

Compound 1 (74%) was obtained in the same manner as in the synthesis of Compound 2 of Synthesis Example 1, except that 2,2,6,6-tetramethylheptane-3,5-dione (9.69 mmol) was used instead of 3,3,7,7-tetramethylnonane-4,6-dione.

HRMS(MALDI) calcd for $C_{53}H_{63}IrN_2O_2$: m/z 952.37. Found: 952.39.

Synthesis Example 3: Synthesis of Compound 3

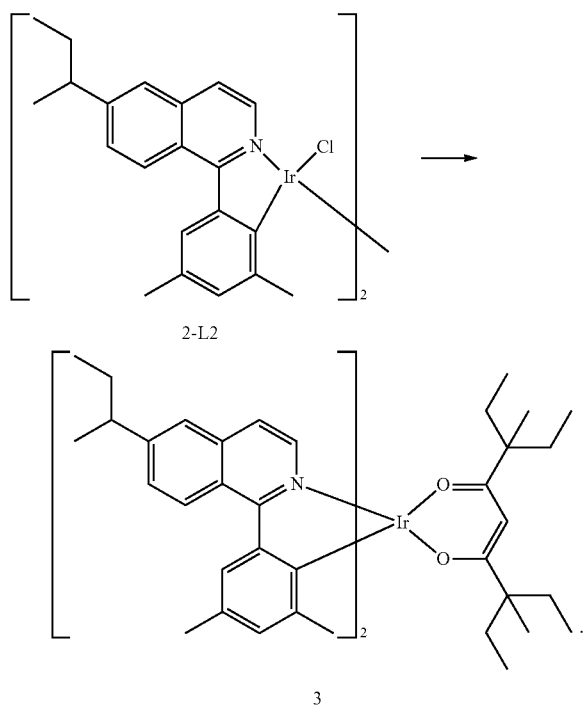

Compound 3 (74%) was obtained in the same manner as in the synthesis of Compound 2 of Synthesis Example 1, except that 3,7-diethyl-3,7-dimethylnonane-4,6-dione (9.69 mmol) was used instead of 3,3,7,7-tetramethylnonane-4,6-dione.

HRMS(MALDI) calcd for $C_{57}H_{71}IrN_2O_2$: m/z 1008.37. Found: 1008.39.

Evaluation Example 1: Evaluation of HOMO and LUMO Energy Levels

According to the methods shown in Table 2, HOMO and LUMO energy levels of Compounds 1 to 3 were evaluated. The results are shown in Table 3.

TABLE 2

| | |
|---|---|
| HOMO energy level evaluation method | Cyclic voltammetry (CV) (electrolyte: 0.1M Bu$_4$NClO$_4$/solvent: CH$_2$Cl$_2$/electrode: 3-electrode system (working electrode: GC, reference electrode: Ag/AgCl, auxiliary electrode: Pt)) was used to obtain a voltage (V)-current (A) graph for each compound. Then, a HOMO energy level of each compound was calculated from a reduction onset of the graph. |
| LUMO energy level evaluation method | Each compound was diluted in CHCl$_3$ at a concentration of $1 \times 10^{-5}$M, and a Shimadzu UV-350 spectrometer was used to measure UB absorption spectra at room temperature. Then, a LUMO energy level was calculated by using an optical band gap (E$_g$) from the edge of the UV absorption spectrum. |

TABLE 3

| Compound No. | HOMO (eV) | LUMO (eV) |
|---|---|---|
| 1 | −5.071 | −2.410 |
| 2 | −5.060 | −2.401 |
| 3 | −5.060 | −2.401 |

Referring to Table 3, it was confirmed that Compounds 1 to 3 had suitable electrical characteristics for use as materials for organic light-emitting devices.

Evaluation Example 2: Evaluation of Photoluminescence Quantum Yield (PLQY)

PMMA solution in $CH_2Cl_2$ was mixed with 5 percent by weight (weight %) of a mixture including CBP and Compound 2 (wherein an amount of Compound 2 was 10 parts by weight of 100 parts by weight of the mixture). The resulting product was spin-coated on a quartz substrate, and the substrate was heat-treated in an oven at a temperature of 80° C., and then, cooled to room temperature, thereby preparing a film.

A PLQY in film of Compound 2 was evaluated by using a Hamamatsu Photonics absolute PL quantum yield measurement system using a xenon light source, equipped with a monochromator, a photonic multichannel analyzer, and an integrating sphere, and utilizing a PLQY measurement software (Hamamatsu Photonics, Ltd., Shizuoka, Japan). The same process was repeated with respect to Compounds 1, 3, and C, and the results are shown in Table 4.

TABLE 4

| Compound No. | Compound 1 | Compound 2 | Compound 3 | Compound C |
|---|---|---|---|---|
| PLQY | 0.837 | 0.905 | 0.917 | 0.734 |

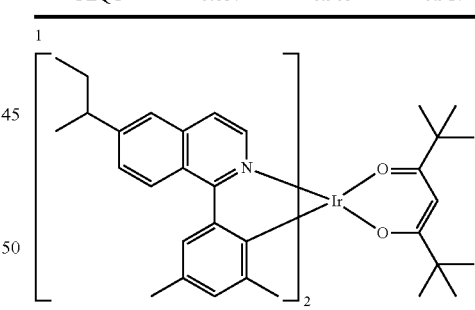

TABLE 4-continued

| Compound No. | Compound 1 | Compound 2 | Compound 3 | Compound C |

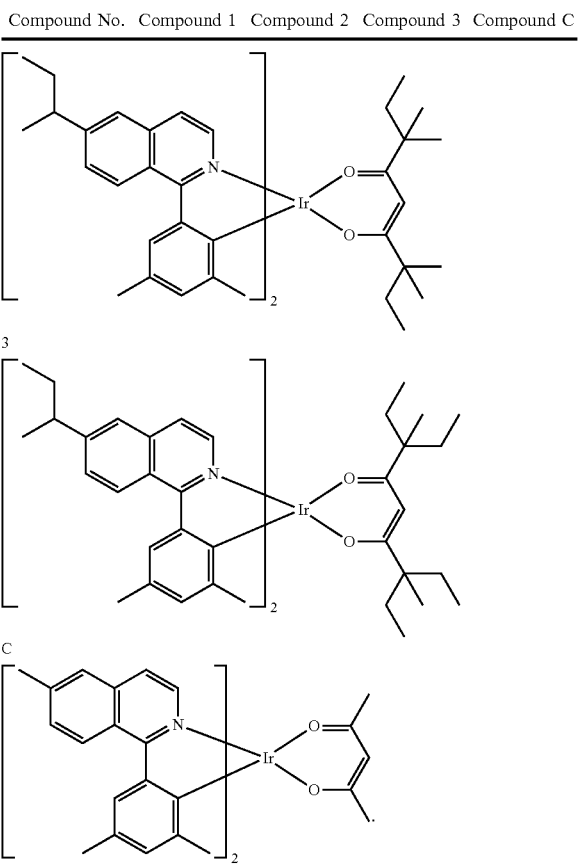

Referring to Table 4, it was confirmed that Compounds 1 to 3 each had a greater PLQY in film than Compound C.

Evaluation Example 3: Measurement of Decay Time

A quarts substrate washed with chloroform and pure water was prepared first, and predetermined materials shown in Table 5 were vacuum-(co)-deposited on the quarts substrate at a vacuum degree of $10^{-7}$ torr, thereby preparing Films 1 to 3, each having a thickness of 50 nm.

TABLE 5

| Film No. | Compound used in film preparation |
|---|---|
| Film 1 | CBP:Compound 1 (at a weight ratio of 9:1) |
| Film 2 | CBP:Compound 2 (at a weight ratio of 9:1) |
| Film 3 | CBP:Compound 3 (at a weight ratio of 9:1) |

Subsequently, a PL spectrum of Film 1 prepared as described above was evaluated at room temperature by using FluoTime 300 which is a TRPL measurement system manufactured by PicoQuant Company and a PLS340 (excitation wavelength=340 nm, spectral width=20 nm) which is a pumping source manufactured by PicoQuant Company. Then, a wavelength of the main peak of the spectrum was determined, and the number of photons emitted at the wavelength of the main film upon a photon pulse (pulse width=500 picoseconds) applied on each film by the PLS340 was measured based on the Time-Correlated Single Photon Counting (TCSPC). This measurement was repeated to obtain a TRPL curve with sufficient fitting. Two or more exponential decay functions were fitted to the obtained results to obtain $T_{decay}(E_x)$, i.e., decay time, of Film 1, and the results are shown in Table 6. The functions used for the fitting is shown in Equation 1 below, and the greatest value among $T_{decay}$ values obtained from each exponential decay function used in the fitting was indicates as $T_{decay}(E_x)$. Here, during the measurement time equal to the measurement time used to obtain the TRPL curve, the same measurement was repeated one more time in a dark state (i.e., a state where a pumping signal incident on the predetermined film was blocked) to obtain a baseline curve or a background signal curve to be used as a baseline for the fitting. The same process was repeated for Films 2 and 3, and the results are shown in Table 6.

$$f(t) = \sum_{i=1}^{n} A_i \exp(-t/T_{decay,i})$$ Equation 1

TABLE 6

| Film No. | Decay time (μs) |
|---|---|
| Film 1 (Compound 1) | 0.950 |
| Film 2 (Compound 2) | 0.995 |
| Film 3 (Compound 3) | 0.993 |

Referring to Table 6, it was confirmed that Compounds 1 to 3 each had excellent decay time.

Example 1

As an anode, a glass substrate on which ITO/Ag/ITO was formed to a thickness of 70 Å/1,000 Å/70 Å was cut to a size of 50 mm×50 mm×0.5 mm, sonicated with isopropyl alcohol and pure water each for 5 minutes, and then, cleaned by exposure to ultraviolet rays and ozone for 30 minutes. Then, the anode was provided to a vacuum deposition apparatus.

2-TNATA was vacuum-deposited on the anode to form a hole injection layer having a thickness of 600 Å, and 4,4'-bis[N-(1-naphthyl)-N-phenylamino]biphenyl (hereinafter, referred to as NPB) was vacuum-deposited on the hole injection layer to form a hole transport layer having a thickness of 1,350 Å.

Next, CBP (as a host) and Compound 1 (as a dopant) were co-deposited at a weight ratio of 98:2 on the hole transport layer to form an emission layer having a thickness of 400 Å.

Then, BCP was vacuum-deposited on the emission layer to form a hole blocking layer having a thickness of 50 Å, and $Alq_3$ was vacuum-deposited on the hole blocking layer to form an electron transport layer having a thickness of 350 Å. LiF was vacuum-deposited on the electron transport layer to form an electron injection layer having a thickness of 10 Å, and Mg and Ag were co-deposited at a weight ratio of 90:10 on the electron injection layer to form a cathode having a thickness of 120 Å, thereby completing the manufacture of an organic light-emitting device:

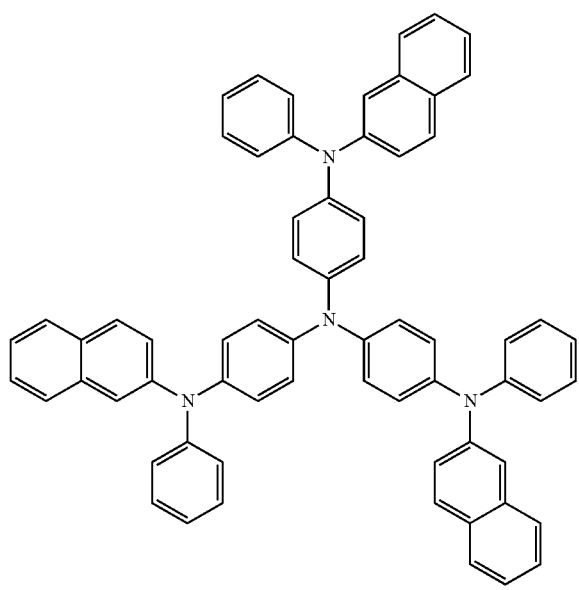

2-TNATA

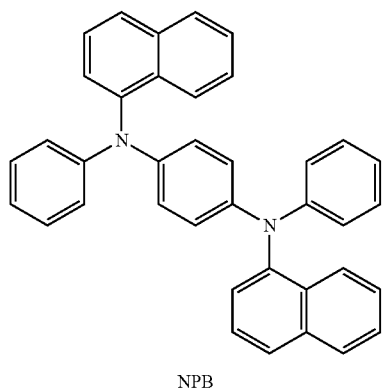

NPB

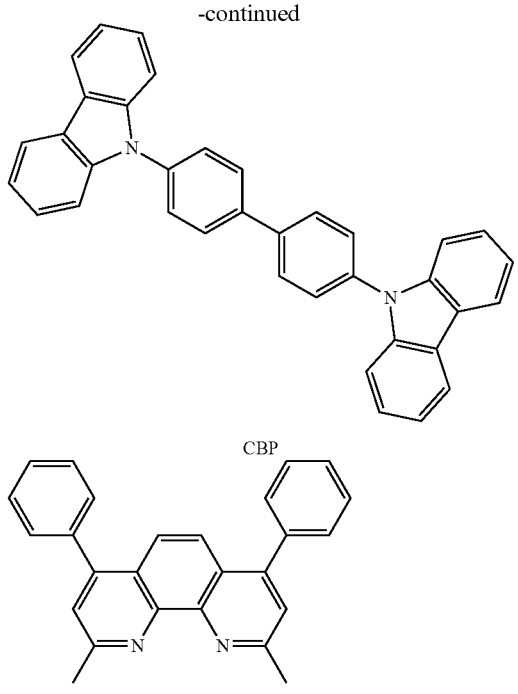

CBP

BCP

Examples 2 and 3 and Comparative Examples A to C

Organic light-emitting devices were manufactured in the same manner as in Example 1, except that compounds listed in Table 7 below were each used as a dopant instead of Compound 1 in forming an emission layer.

Evaluation Example 4: Evaluation of Characteristics of Organic Light-Emitting Device The driving voltage, current density, maximum external quantum efficiency (Max EQE), roll-off ratio, emission peak wavelength of EL spectrum, FWHM of EL spectrum, emission color, color coordinates ($CIE_x$), and/or lifespan ($T_{97}$) of the organic light-emitting devices manufactured according to Examples 1 to 3 and Comparative Examples A to C were evaluated, and the results are shown in Table 7. Here, as a device used for the evaluation, a current-voltage meter (Keithley 2400) and a luminance meter (Minolta Cs-1000A) were used. The lifespan ($T_{97}$) (at 3,500 nit) was obtained by evaluating time (hours, hr) that lapsed when luminance was 97% of initial luminance (100%). The roll-off ratio was calculated according to Equation 20 below:

$$\text{Roll off ratio} = \{1-(\text{efficiency (at 3,500 nit)}/\text{maximum luminance efficiency})\} \times 100\% \quad \text{Equation 20}$$

TABLE 7

| | Compound No. of dopant in emission layer | Driving voltage (V) | Current density (mA/cm$^2$) | Max EQE (%) | Roll-off Ratio (%) | Emission peak wavelength (nm) | FWHM (nm) | Emission color | Color coordinate ($CIE_x$) | $LT_{97}$ (hr) |
|---|---|---|---|---|---|---|---|---|---|---|
| Example 1 | 1 | 5.20 | 5.71 | 28.0 | 15 | 626 | 54 | Red | 0.684 | 252 |
| Example 2 | 2 | 5.16 | 6.40 | 28.2 | 15 | 625 | 51 | Red | 0.677 | 280 |
| Example 3 | 3 | 5.11 | 6.46 | 28.6 | 14 | 624 | 49 | Red | 0.674 | 306 |
| Comparative Example A | A | 5.22 | 8.01 | 24.1 | 19 | — | 60 | Red | 0.683 | 200 |

TABLE 7-continued
| | Compound No. of dopant in emission layer | Driving voltage (V) | Current density (mA/cm²) | Max EQE (%) | Roll-off Ratio (%) | Emission peak wavelength (nm) | FWHM (nm) | Emission color | Color coordinate (CIE$_x$) | LT$_{97}$ (hr) |
|---|---|---|---|---|---|---|---|---|---|---|
| Comparative Example B | B | 5.32 | 6.98 | 25.6 | 16 | 624 | 55 | Red | 0.675 | 210 |
| Comparative Example C | C | 5.42 | 7.11 | 24.1 | 19 | 634 | 60 | Red | 0.683 | 210 |
1
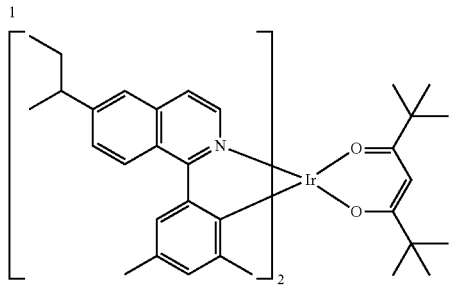
2
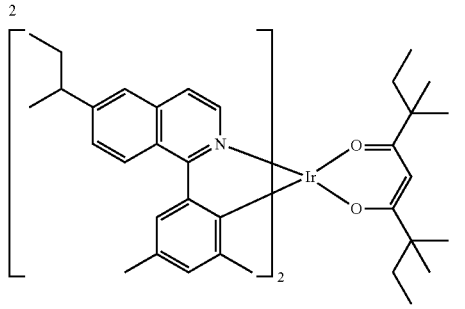
3
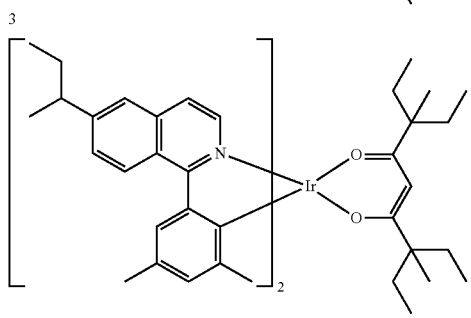
A
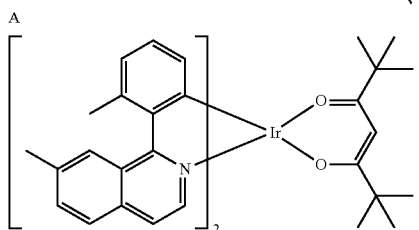
B
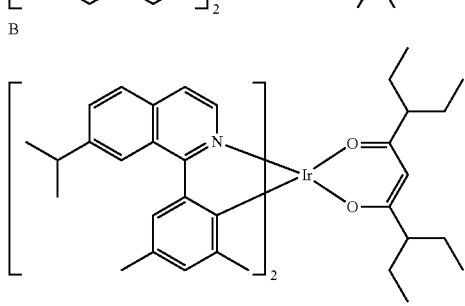
C TABLE 7-continued

| Compound No. of dopant in emission layer | Driving voltage (V) | Current density (mA/cm²) | Max EQE (%) | Roll-off Ratio (%) | Emission peak wavelength (nm) | FWHM (nm) | Emission color | Color coordinate (CIEx) | LT97 (hr) |
|---|---|---|---|---|---|---|---|---|---|

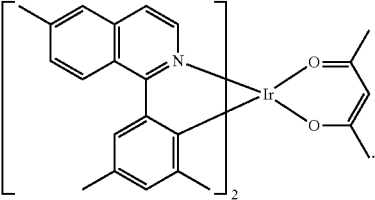

Referring to Table 7, it was confirmed that the organic light-emitting devices manufactured according to Examples 1 to 3 emitted red light having excellent color purity, and also had an improved driving voltage, an improved external quantum efficiency, an improved roll-off ratio, and an improved lifespan, as compared with the organic light-emitting devices manufactured according to Comparative Examples A to C.

According to the one or more embodiments, the organometallic compound has excellent electric characteristics and stability, and thus, an electronic device, for example, an organic light-emitting device, including the organometallic compound may have a low driving voltage, good external quantum efficiency, a low roll-off ratio, and a long lifespan. In addition, since the organometallic compound has excellent phosphorescence characteristics, a diagnostic composition including the organometallic compound may be provided with a high diagnosis efficiency.

It should be understood that embodiments described herein should be considered in a descriptive sense only and not for purposes of limitation. Descriptions of features or aspects within each embodiment should typically be considered as available for other similar features or aspects in other embodiments.

While one or more embodiments have been described with reference to the FIGURES, it will be understood by those of ordinary skill in the art that various changes in form and details may be made therein without departing from the spirit and scope of the present disclosure as defined by the following claims.

What is claimed is:
1. An organometallic compound represented by Formula 1:

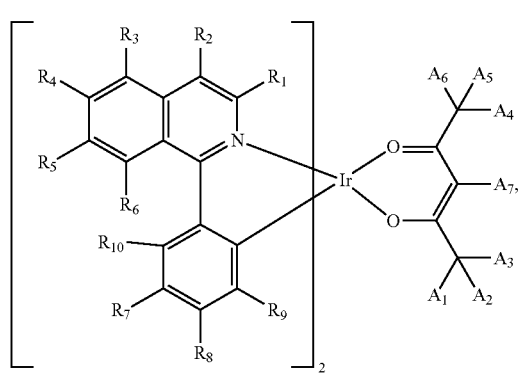

Formula 1 wherein, in Formula 1,
$R_1$ to $R_3$ and $R_5$ to $R_{10}$ are each independently hydrogen, deuterium, —F, —Cl, —Br, —I, —SF$_5$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_7$-$C_{60}$ arylalkyl group, a substituted or unsubstituted $C_1$-$C_{60}$ heteroaryl group, a substituted or unsubstituted $C_1$-$C_{60}$ heteroaryloxy group, a substituted or unsubstituted $C_1$-$C_{60}$ heteroarylthio group, a substituted or unsubstituted $C_2$-$C_{60}$ heteroarylalkyl group, a substituted or unsubstituted monovalent non-aromatic condensed polycyclic group, a substituted or unsubstituted monovalent non-aromatic condensed heteropolycyclic group, —N(Q$_1$)(Q$_2$), —Si(Q$_3$)(Q$_4$)(Q$_5$), —Ge(Q$_3$)(Q$_4$)(Q$_5$), —B(Q$_6$)(Q$_7$), —P(=O)(Q$_8$)(Q$_9$), or —P(Q$_8$)(Q$_9$),
is a substituted or unsubstituted $C_2$-$C_{60}$ alkyl group, or a substituted or unsubstituted $C_3$-$C_{10}$ cycloalkyl group,
$A_1$ to $A_6$ are each independently a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_3$-$C_{10}$ cycloalkyl group, a substituted or unsubstituted $C_3$-$C_{10}$ cycloalkenyl group, a substituted or unsubstituted $C_6$-$C_{60}$ aryl group, a substituted or unsubstituted $C_7$-$C_{60}$ arylalkyl group, or a substituted or unsubstituted monovalent non-aromatic condensed polycyclic group, provided that at least one of $A_1$ to $A_6$ is a $C_2$-$C_{60}$ alkyl group,
A7 is hydrogen or deuterium,
two or more of $R_1$ to $R_3$ and $R_5$ to $R_{10}$ are optionally linked to form a $C_5$-$C_{60}$ carbocyclic group unsubstituted or substituted with at least one $R_{1a}$ or a $C_1$-$C_{60}$ heterocyclic group unsubstituted or substituted with at least one $R_{1a}$, two or more of $A_1$ to $A_6$ are optionally linked to form a $C_5$-$C_{60}$ carbocyclic group unsubstituted or substituted with at least one $R_{1a}$;

$R_{1a}$ is the same as defined in connection with $R_7$, a substituent(s) of the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_7$-$C_{60}$ arylalkyl group, the substituted $C_1$-$C_{60}$ heteroaryl group, the substituted $C_1$-$C_{60}$ heteroaryloxy group, the substituted $C_1$-$C_{60}$ heteroarylthio group, the substituted $C_2$-$C_{60}$ heteroarylalkyl group, the substituted monovalent non-aromatic condensed polycyclic group, and the substituted monovalent non-aromatic condensed heteropolycyclic group is each independently:

deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, or a $C_1$-$C_{60}$ alkoxy group;

a $C_1$-$C_{60}$ alkyl group, a $C_2$-$C_{60}$ alkenyl group, a $C_2$-$C_{60}$ alkynyl group, or $C_1$-$C_{60}$ alkoxy group, each substituted with deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ arylalkyl group, a $C_1$-$C_{60}$ heteroaryl group, a $C_1$-$C_{60}$ heteroaryloxy group, a $C_1$-$C_{60}$ heteroarylthio group, a $C_2$-$C_{60}$ heteroarylalkyl group, a monovalent non-aromatic condensed polycyclic group, a monovalent non-aromatic condensed heteropolycyclic group, —N($Q_{11}$)($Q_{12}$), —Si($Q_{13}$)($Q_{14}$)($Q_{15}$), —Ge($Q_{13}$)($Q_{14}$)($Q_{15}$), —B($Q_{16}$)($Q_{17}$), —P(=O)($Q_{18}$)($Q_{19}$), —P($Q_{18}$)($Q_{19}$), or any combination thereof;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ arylalkyl group, a $C_1$-$C_{60}$ heteroaryl group, a $C_1$-$C_{60}$ heteroaryloxy group, a $C_1$-$C_{60}$ heteroarylthio group, a $C_2$-$C_{60}$ heteroarylalkyl group, a monovalent non-aromatic condensed polycyclic group, or a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ arylalkyl group, a $C_1$-$C_{60}$ heteroaryl group, a $C_1$-$C_{60}$ heteroaryloxy group, a $C_1$-$C_{60}$ heteroarylthio group, a $C_2$-$C_{60}$ heteroarylalkyl group, a monovalent non-aromatic condensed polycyclic group, or a monovalent non-aromatic condensed heteropolycyclic group, each substituted with deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ arylalkyl group, a $C_1$-$C_{60}$ heteroaryl group, a $C_1$-$C_{60}$ heteroaryloxy group, a $C_1$-$C_{60}$ heteroarylthio group, a $C_2$-$C_{60}$ heteroarylalkyl group, a monovalent non-aromatic condensed polycyclic group, a monovalent non-aromatic condensed heteropolycyclic group, —N($Q_{21}$)($Q_{22}$), —Si($Q_{23}$)($Q_{24}$)($Q_{25}$), —Ge($Q_{23}$)($Q_{24}$)($Q_{25}$), —B($Q_{26}$)($Q_{27}$), —P(=O)($Q_{28}$)($Q_{29}$), —P($Q_{28}$)($Q_{29}$), or any combination thereof;

—N($Q_{31}$)($Q_{32}$), —Si($Q_{33}$)($Q_{34}$)($Q_{35}$), —Ge($Q_{33}$)($Q_{34}$)($Q_{35}$), —B($Q_{36}$)($Q_{37}$), —P(=O)($Q_{38}$)($Q_{39}$), —P($Q_{38}$)($Q_{39}$), or any combination thereof; or any combination thereof, and $Q_1$ to $Q_9$, $Q_{11}$ to $Q_{19}$, $Q_{21}$ to $Q_{29}$, and $Q_{31}$ to $Q_{39}$ are each independently hydrogen; deuterium; —F; —Cl; —Br; —I; a hydroxyl group; a cyano group; a nitro group; an amino group; an amidino group; a hydrazine group; a hydrazone group; a carboxylic acid group or a salt thereof, a sulfonic acid group or a salt thereof, a phosphoric acid group or a salt thereof; a $C_1$-$C_{60}$ alkyl group; a $C_2$-$C_{60}$ alkenyl group; a $C_2$-$C_{60}$ alkynyl group; a $C_1$-$C_{60}$ alkoxy group; a $C_3$-$C_{10}$ cycloalkyl group; a $C_1$-$C_{10}$ heterocycloalkyl group; a $C_3$-$C_{10}$ cycloalkenyl group; a $C_1$-$C_{10}$ heterocycloalkenyl group; a $C_6$-$C_{60}$ aryl group; a $C_6$-$C_{60}$ aryl group substituted with a $C_1$-$C_{60}$ alkyl group, a $C_6$-$C_{60}$ aryl group or any combination thereof, a $C_6$-$C_{60}$ aryloxy group; a $C_6$-$C_{60}$ arylthio group; a $C_7$-$C_{60}$ arylalkyl group; a $C_1$-$C_{60}$ heteroaryl group; a $C_1$-$C_{60}$ heteroaryloxy group; a $C_1$-$C_{60}$ heteroarylthio group; a $C_2$-$C_{60}$ heteroarylalkyl group; a monovalent non-aromatic condensed polycyclic group; or a monovalent non-aromatic condensed heteropolycyclic group.

2. The organometallic compound of claim 1, wherein $R_1$ to $R_3$ and $R_5$ to $R_{10}$ are each independently:

hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, —SF$_5$, a $C_1$-$C_{20}$ alkyl group, or a $C_1$-$C_{20}$ alkoxy group;

a $C_1$-$C_{20}$ alkyl group or a $C_1$-$C_{20}$ alkoxy group, each substituted with deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{20}$ alkoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a bicyclo[1.1.1]pentyl group, a bicyclo[2.1.1]hexyl group, a bicyclo

[2.2.1]heptyl group, a bicyclo[2.2.2]octyl group, a phenyl group, a ($C_1$-$C_{20}$ alkyl)phenyl group, a biphenyl group, a terphenyl group, a naphthyl group, a pyridinyl group, a pyrimidinyl group, or a combination thereof;

a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a bicyclo[1.1.1]pentyl group, a bicyclo[2.1.1]hexyl group, a bicyclo[2.2.1]heptyl group, a bicyclo[2.2.2]octyl group, a phenyl group, a ($C_1$-$C_{20}$ alkyl)phenyl group, a biphenyl group, a terphenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, or an imidazopyrimidinyl group, each unsubstituted or substituted with deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{20}$ alkoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a bicyclo[1.1.1]pentyl group, a bicyclo[2.1.1]hexyl group, a bicyclo[2.2.1]heptyl group, a bicyclo[2.2.2]octyl group, a phenyl group, a ($C_1$-$C_{20}$ alkyl)phenyl group, a biphenyl group, a terphenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, an imidazopyrimidinyl group, or any combination thereof;

—$N(Q_1)(Q_2)$, —$Si(Q_3)(Q_4)(Q_5)$, —$B(Q_6)(Q_7)$, or —$P(=O)(Q_8)(Q_9)$; or any combination thereof, is:

a $C_2$-$C_{20}$ alkyl group unsubstituted or substituted with deuterium, —F, —Cl, —Br, —I, —$CD_3$, —$CD_2H$, —$CDH_2$, —$CF_3$, —$CF_2H$, —$CFH_2$, a cyano group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a bicyclo[1.1.1]pentyl group, a bicyclo[2.1.1]hexyl group, a bicyclo[2.2.1]heptyl group, a bicyclo[2.2.2]octyl group, or any combination thereof; or a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a bicyclo[1.1.1]pentyl group, a bicyclo[2.1.1]hexyl group, a bicyclo[2.2.1]heptyl group, a bicyclo[2.2.2]octyl group, each unsubstituted or substituted with deuterium, —F, —Cl, —Br, —$CD_3$, —$CD_2H$, —$CDH_2$, —$CF_3$, —$CF_2H$, —$CFH_2$, a cyano group, a $C_1$-$C_{10}$ alkyl group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a bicyclo[1.1.1]pentyl group, a bicyclo[2.1.1]hexyl group, a bicyclo[2.2.1]heptyl group, a bicyclo[2.2.2]octyl group, or any combination thereof;

and $Q_1$ to $Q_9$ are each independently:

—$CH_3$, —$CD_3$, —$CD_2H$, —$CDH_2$, —$CH_2CH_3$, —$CH_2CD_3$, —$CH_2CD_2H$, —$CH_2CDH_2$, —$CHDCH_3$, —$CHDCD_2H$, —$CHDCDH_2$, —$CHDCD_3$, —$CD_2CD_3$, —$CD_2CD_2H$, or —$CD_2CDH_2$; or an n-propyl group, an isopropyl group, an n-butyl group, a sec-butyl group, an isobutyl group, a tert-butyl group, an n-pentyl group, a tert-pentyl group, a neopentyl group, an isopentyl group, a sec-pentyl group, a 3-pentyl group, a sec-isopentyl group, a phenyl group, a biphenyl group, or a naphthyl group, each unsubstituted or substituted with deuterium, a $C_1$-$C_{10}$ alkyl group, a phenyl group, or any combination thereof.

3. The organometallic compound of claim 1, wherein $A_1$ to $A_6$ are each independently:

a $C_1$-$C_{20}$ alkyl unsubstituted or substituted with deuterium, —F, —Cl, —Br, —I, —$CD_3$, —$CD_2H$, —$CDH_2$, —$CF_3$, —$CF_2H$, —$CFH_2$, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a bicyclo[1.1.1]pentyl group, a bicyclo[2.1.1]hexyl group, a bicyclo[2.2.1]heptyl group, a bicyclo[2.2.2]octyl group, a phenyl group, a ($C_1$-$C_{20}$alkyl)phenyl group, a biphenyl group, a terphenyl group, a naphthyl group, or any combination thereof; or a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a bicyclo[1.1.1]pentyl group, a bicyclo[2.1.1]

hexyl group, a bicyclo[2.2.1]heptyl group, a bicyclo[2.2.2]octyl group, a phenyl group, a (C$_1$-C$_{20}$ alkyl)phenyl group, a biphenyl group, a terphenyl group, a naphthyl group, a fluorenyl group, a phenanthrenyl group, an anthracenyl group, a fluoranthenyl group, a triphenylenyl group, a pyrenyl group, a chrysenyl group, each unsubstituted or substituted with deuterium, —F, —Cl, —Br, —I, —CD$_3$, —CD$_2$H, —CDH$_2$, —CF$_3$, —CF$_2$H, —CFH$_2$, a cyano group, a C$_1$-C$_{10}$ alkyl group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a bicyclo[1.1.1]pentyl group, a bicyclo[2.1.1]hexyl group, a bicyclo[2.2.1]heptyl group, a bicyclo[2.2.2]octyl group, a phenyl group, a (C$_1$-C$_{20}$ alkyl)phenyl group, a biphenyl group, a terphenyl group, a naphthyl group, a fluorenyl group, a phenanthrenyl group, an anthracenyl group, a fluoranthenyl group, a triphenylenyl group, a pyrenyl group, a chrysenyl group, or any combination thereof.

4. The organometallic compound of claim 1, wherein R$_4$ is a group represented by Formula 2:

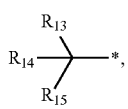

Formula 2 wherein, the number of carbon atoms in Formula 2 is 4 or more,

R$_{13}$ in Formula 2 is hydrogen, deuterium, a C$_1$-C$_{20}$ alkyl group, deuterium-containing C$_1$-C$_{20}$ alkyl group, a C$_3$-C$_{10}$ cycloalkyl group, or a deuterium-containing C$_3$-C$_{10}$ cycloalkyl group, R$_{14}$ and R$_{15}$ in Formula 2 are each independently a C$_1$-C$_{20}$ alkyl group, a deuterium-containing C$_1$-C$_{20}$ alkyl group, a C$_3$-C$_{10}$ cycloalkyl group, or a deuterium-containing C$_3$-C$_{10}$ cycloalkyl group, and

* indicates a binding site to a neighboring atom.

5. The organometallic compound of claim 4, wherein R$_{13}$ in Formula 2 is hydrogen or deuterium.

6. The organometallic compound of claim 4, wherein R$_{14}$ and R$_{15}$ in Formula 2 are different from each other.

7. The organometallic compound of claim 4, wherein in Formula 2,

R$_{13}$ is hydrogen, deuterium, —CH$_3$, —CDH$_2$, —CD$_2$H, or —CD$_3$,

R$_{14}$ and R$_{15}$ are each independently:

a methyl group, an ethyl group, an n-propyl group, an isopropyl group, an n-butyl group, a sec-butyl group, an isobutyl group, a tert-butyl group, an n-pentyl group, a tert-pentyl group, a neopentyl group, an isopentyl group, a sec-pentyl group, a 3-pentyl group, a sec-isopentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an isononyl group, a sec-nonyl group, a tert-nonyl group, an n-decyl group, an isodecyl group, a sec-decyl group, a tert-decyl group, a cyclopentyl group, a cyclohexyl group, a cycloheptyl group, a cyclooctyl group, a bicyclo[1.1.1]pentyl group, a bicyclo[2.1.1]hexyl group, a bicyclo[2.2.1]heptyl group, or a bicyclo[2.2.2]octyl group; or a methyl group, an ethyl group, an n-propyl group, an isopropyl group, an n-butyl group, a sec-butyl group, an isobutyl group, a tert-butyl group, an n-pentyl group, a tert-pentyl group, a neopentyl group, an isopentyl group, a sec-pentyl group, a 3-pentyl group, a sec-isopentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an isononyl group, a sec-nonyl group, a tert-nonyl group, an n-decyl group, an isodecyl group, a sec-decyl group, a tert-decyl group, a cyclopentyl group, a cyclohexyl group, a cycloheptyl group, a cyclooctyl group, a bicyclo[1.1.1]pentyl group, a bicyclo[2.1.1]hexyl group, a bicyclo[2.2.1]heptyl group, or a bicyclo[2.2.2]octyl group, each substituted with at least one deuterium.

8. The organometallic compound of claim 1, wherein R$_7$, and R$_9$ in Formula 1 are each not hydrogen.

9. The organometallic compound of claim 1, wherein R$_7$ and R$_9$ in Formula 1 are each not hydrogen and identical to each other.

10. The organometallic compound of claim 1, wherein at least one of A$_1$ to A$_6$ is a substituted or unsubstituted C$_2$-C$_{60}$ alkyl group, a substituted or unsubstituted C$_2$-C$_{60}$ alkenyl group, a substituted or unsubstituted C$_2$-C$_{60}$ alkynyl group, a substituted or unsubstituted C$_3$-C$_{10}$ cycloalkyl group, a substituted or unsubstituted C$_3$-C$_{10}$ cycloalkenyl group, a substituted or unsubstituted C$_1$-C$_{10}$ heterocycloalkenyl group, a substituted or unsubstituted C$_6$-C$_{60}$ aryl group, a substituted or unsubstituted C$_7$-C$_{60}$ arylalkyl group, or a substituted or unsubstituted monovalent non-aromatic condensed polycyclic group.

11. The organometallic compound of claim 1, wherein in Formula 1, at least one of a group represented by *—C(A$_1$)(A$_2$)(A$_3$), a group represented by *—C(A$_4$)(A$_5$)(A$_6$), or a combination thereof is an adamantane group, a norbornane group, a norbornene group, a bicyclo[1.1.1]pentane group, a bicyclo[2.1.1]hexane group, a bicyclo[2.2.1]heptane group, a bicyclo[2.2.2]octane group, each unsubstituted or substituted with at least one R$_{1a}$.

12. The organometallic compound of claim 1, wherein the organometallic compound is one of Compounds 2, 3, 5, and 6:

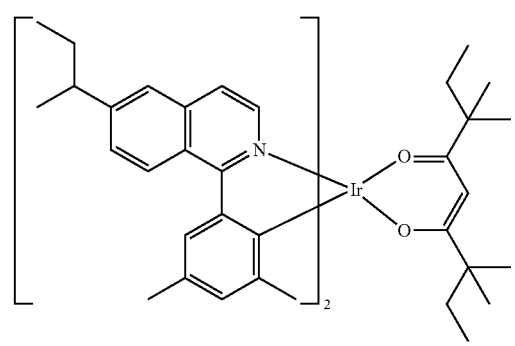

2

-continued

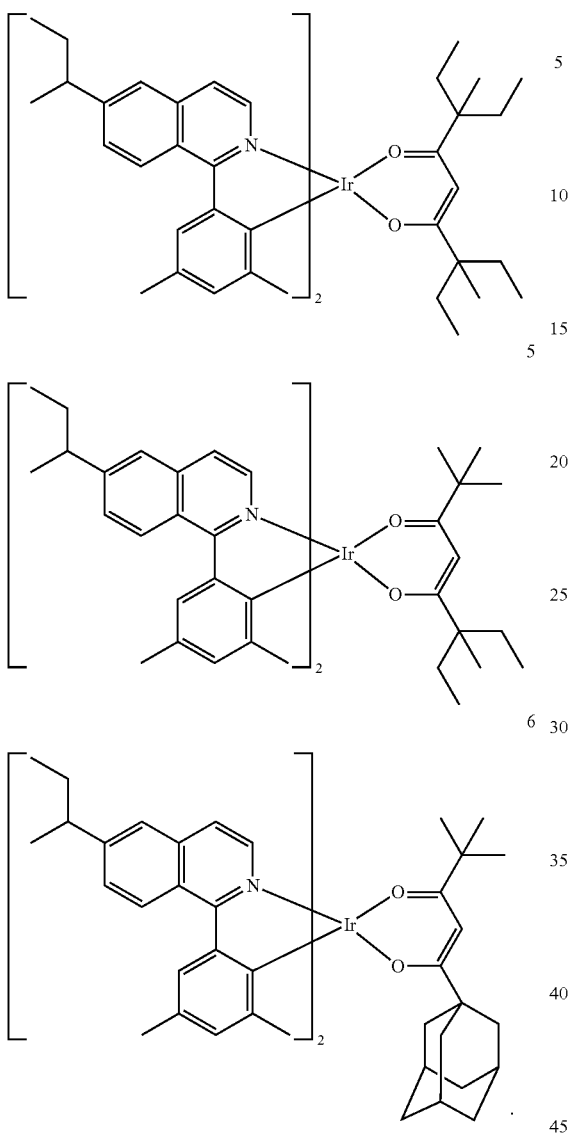

13. An organic light-emitting device comprising:
a first electrode;
a second electrode; and
an organic layer disposed between the first electrode and the second electrode and comprising an emission layer,
wherein the organic layer comprises at least one organometallic compound of claim 1.

14. The organic light-emitting device of claim 13, wherein
the first electrode is an anode,
the second electrode is a cathode,
the organic layer further comprises a hole transport disposed between the first electrode and the emission layer and an electron transport region disposed between the emission layer and the second electrode,
the hole transport region comprises a hole injection layer, a hole transport layer, an electron blocking layer, a buffer layer, or any combination thereof, and
the electron transport region comprises a hole blocking layer, an electron transport layer, an electron injection layer, or any combination thereof.

15. The organic light-emitting device of claim 13, wherein
the emission layer comprises the at least one organometallic compound.

16. The organic light-emitting device of claim 15, wherein the emission layer emits red light.

17. The organic light-emitting device of claim 15, wherein
the emission layer further comprises a host, and
an amount of the host in the emission layer is greater than that of the organometallic compound in the emission layer.

18. A diagnostic composition comprising at least one organometallic compound of claim 1.

* * * * *